(12) United States Patent
Ding et al.

(10) Patent No.: US 6,645,724 B1
(45) Date of Patent: Nov. 11, 2003

(54) ASSAYS FOR ENDOTOXIN

(75) Inventors: Jeak Ling Ding, Singapore (SG); Bow Ho, Singapore (SG)

(73) Assignee: National University of Singapore, Singapore (SG)

( * ) Notice: Subject to any disclaimer, the term of this patent is extended or adjusted under 35 U.S.C. 154(b) by 0 days.

(21) Appl. No.: 09/287,368

(22) Filed: Apr. 7, 1999

Related U.S. Application Data

(63) Continuation-in-part of application No. 09/201,786, filed on Dec. 1, 1998, now abandoned, which is a continuation-in-part of application No. 09/081,767, filed on May 21, 1998, now abandoned.
(60) Provisional application No. 60/058,816, filed on Sep. 19, 1997.

(51) Int. Cl.$^7$ .............. A61K 39/02; G01N 33/53; C12P 21/06; C12N 15/09; C12N 15/64
(52) U.S. Cl. .............. 435/7.1; 424/236.1; 435/91.4; 435/219; 435/252.3; 435/320.1; 435/348; 435/69.1; 435/69.3; 436/546; 530/384; 530/390.1; 530/391.5; 530/391.7; 936/14; 936/16; 936/22; 936/31
(58) Field of Search .............. 424/236.1, 7.1, 424/69.3; 435/91.4, 219, 252.3, 320.1, 348; 436/546; 530/384, 390.1, 391.5, 391.7; 936/14, 16, 22, 31

(56) References Cited

U.S. PATENT DOCUMENTS

| | | | |
|---|---|---|---|
| 5,336,610 A | * 8/1994 | Esmon et al. | 435/212 |
| 5,712,144 A | 1/1998 | Ding et al. | 435/219 |
| 5,716,834 A | 2/1998 | Ding et al. | 435/219 |

FOREIGN PATENT DOCUMENTS

| | | | | |
|---|---|---|---|---|
| EP | 588303 | * | 9/1993 | G01N/33/52 |
| EP | 613004 | * | 2/1994 | G01N/33/579 |
| EP | 649021 | * | 9/1994 | G01N/33/579 |

OTHER PUBLICATIONS

Carbonell et al. 1985. J. of Virology. vol. 56 (1): 153–160.*
Ding et al. 1993. Biochimica et Biophysica Acta. 1202:149–156.*
Ding et al. 1995. Mol. Mar. Bio. Biotech. 4(1): 90–103.*
Ho et al. 1993. Biochem and Mol. Biol. Intl. 29(4): 687–694.*
Muta et al. 1991. J. of Biol. Chem. 266(10): 6554–6561.*
Nakamura et al. 1986. Eur. J. Biochem. 154:511–521.*
Navas et al. 1990. Biochem Intl. 21(5): 805–813.*
Zhang et al. 1994. J. of Clin. Micro. 32(6): 1537–1541.*
T. Muta et al., *J. Biol. Chem.*, vol. 266, pp. 6554–6559 (1991).
M. A. A. Navas et al., *Biochem. Int.*, vol. 21, No. 5, pp. 805–813 (1990).
J. L. Ding et al., *Biochem. Biophys. Acta*, vol. 1202, pp. 149–156 (1993).
B. Ho et al., *Biochem. Mol. Biol. Intl.*, vol. 29, No. 4, 687–694 (1993).
S. Iwanaga, *Current Opinion in Immunol.*, Vol 5, pp. 74–82 (1993).
B. Ho., *Microbios Letters*, vol. 24, pp. 81–84 (1983).
T. J. Novitsky, *Oceanus*, vol. 27, pp. 13–18 (1991).
K. Sekiguchi et al., *Biomedical Applications of the Horseshoe Crabs*, Eds., Cohen et al., Allan R. Liss, New York, pp. 37–49 (1979).
J. L. Ding et al., *Mol. Marine Biol. Biotechnol.*, vol. 4, pp. 90–103 (1995).
S. D. Roopashree et al., *Biochem. Mol. Biol. Intl.*, vol. 35, pp. 841–849 (1995).
S. D. Roospashree et al., *Mol. Marine Biol. Biotechnol.*, vol. 5, No. 4, pp. 334–343 (1996).
J. L. Ding et al., *J. Endotoxin Res.*, vol. 4, No. 1, pp. 1–11 (1997).
A. W. M. Pui et al., *J. Endotoxin Research*, vol. 4, No. 6, pp. 383–392 (1997).
Sambrook et al., *Molecular Cloning: A Laboratory Manual*, $2^{nd}$ ed., c. 1989, Coldspring Harbor Laboratory, pp. 9.49–9.51 (1989).
M. Grunstein et al., *Proc. Natl. Acad. Sci. USA*, Vo. 72, No. 10, pp. 3961–3965 (1975).
M. Bradford, *Anal. Biochem.*, vol. 72, pp. 248–254 (1976).
U.K. Laemmli, *Nature*, vol. 227, pp. 680–685 (1970).
S. Iwanaga et al., Endotoxin–sensitive Substance. Japan Patent Agency Official Bulletin; S57–108018.
T. Nakamura et al., *Eur. J. Biochem.*, vol. 154, pp. 511–521 (1986).
J. F. Cooper, *Bull. Parent. Drug Ass.*, Vo. 29, No. 3, pp. 122–130 (1975).
Wang, et al., "Modular Arrangement and Secretion of a Multidomain Serine Protease", *The Journal of Biological Chemistry*, 277:36363–36372 (2002).

* cited by examiner

Primary Examiner—Lynette R. F. Smith
Assistant Examiner—Ja-Na Hines
(74) Attorney, Agent, or Firm—Birch, Stewart, Kolasch & Birch, LLP

(57) ABSTRACT

The horseshoe crab, *Carcinoscorpius rotundicauda* Factor C cDNA (CrFC21) has been cloned into a shuttle baculoviral vector and another vector suitable for expression in insect cells. The recombinant baculoviral DNA was then transfected into the insect cells for expression of recombinant Factor C. Recombinant Factor C was found to be immunoreactive and is capable of binding both free and bound/immobilized lipid A. It is enzymatically active when triggered by LPS. The rFC is probably of the two-chain form, being cleaved into the heavy and light chains after activation by Gram negative bacterial endotoxin. As low as 0.01 pg (0.001 ng/ml) of LPS was detectable by the rFC, thus, indicating its potentials as a novel generation of "limulus amoebocyte lysate."

25 Claims, 25 Drawing Sheets

```
5'
GTG GAA TTC TGC AGA TGC TAC CGG ACT CAG ATC AAT TCA CAT CCA CCA GCC
ATG AGG GTG CTT GTA CTA GCT CTT GCT GTG GCT CTC GCA GTG GGG GAC CAG
 M   R   V   L   V   L   A   L   A   V   A   L   A   V   G   D   Q
    ──────▶                                                    ↑
    OaVtgss                                               Cleavage site TCC AAC TTG GGG GAT CTA GGC TTG TGT GAT GAA ACG AGG TTC GAG TGT AAG
 S   N   L   G   D   L   G   L   C   D   E   T   R   F   E   C   K
                ─────────▶
                 Factor C TGT GGC GAT CCA GGC TAT GTG TTC AAC ATT CCA GTG AAA CAA TGT ACA TAC 3'
 C   G   D   P   G   Y   V   F   N   I   P   V   K   Q   C   Y   F
                                                    pAC5/VtgCrFCES-V5-His
```

FIG.14A

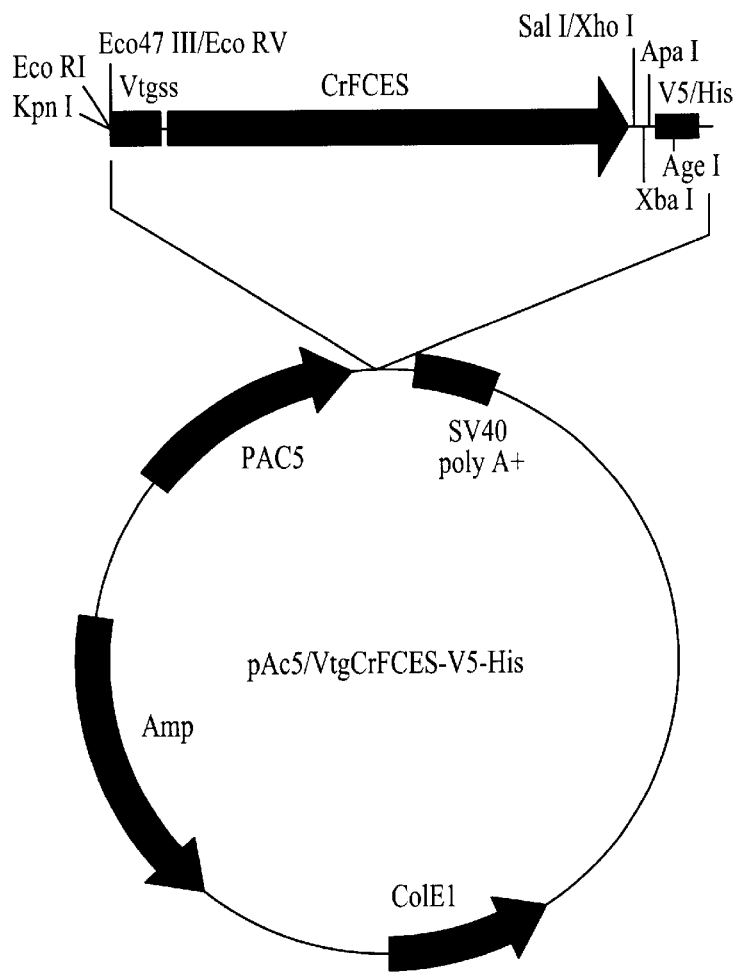

FIG.14B

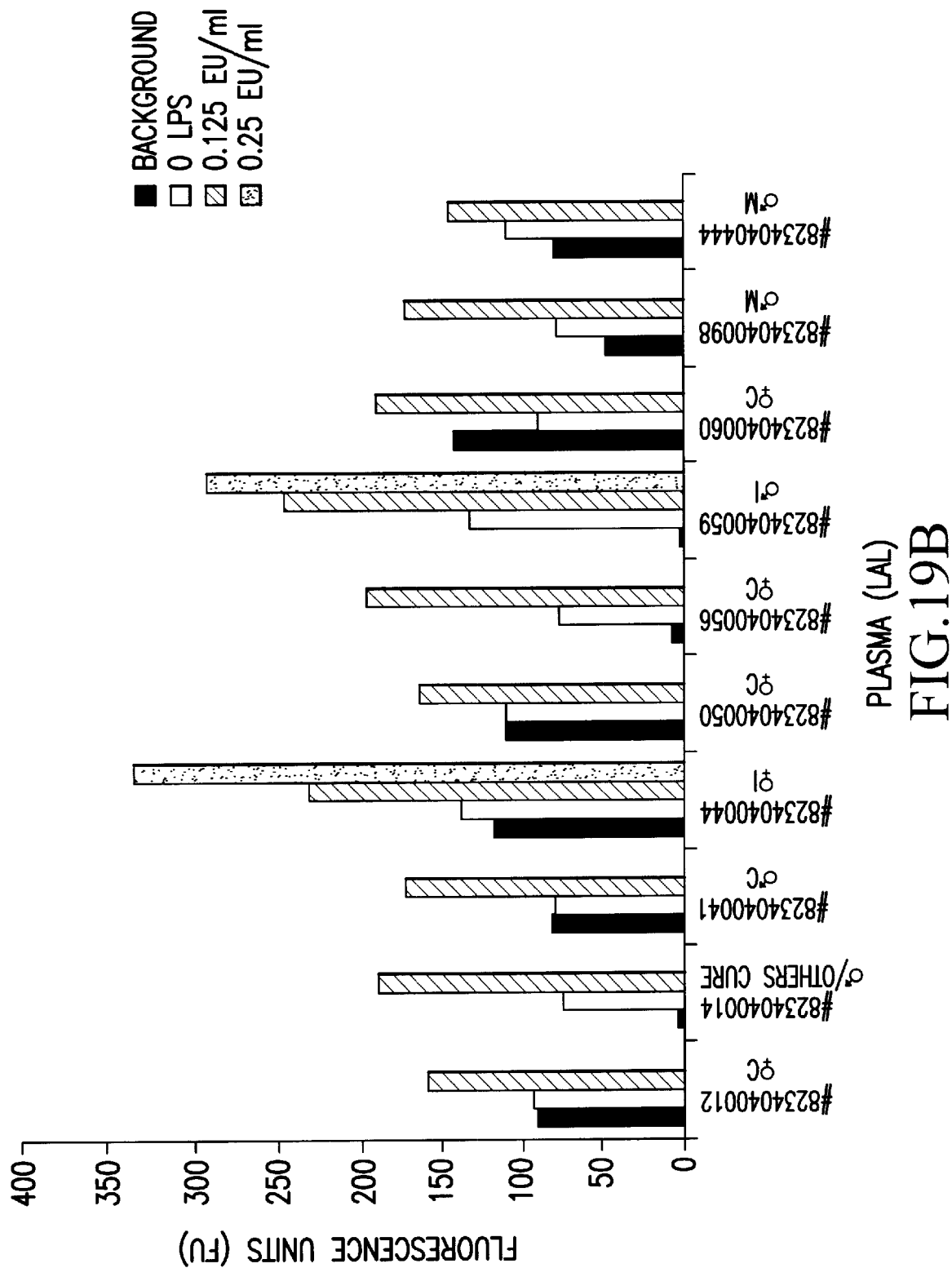

ASSAYS FOR ENDOTOXIN

RELATED APPLICATIONS

The present application is a Continuation-In-Part of Ser. No. 09/201,786, filed Dec. 1, 1998 now abandoned, which in turn is a Continuation-In-Part of Ser. No. 09/081,767, filed May 21, 1998 now abandoned which in turn relies upon Provisional Application No. 60/058,816, filed Sep. 19, 1997. Each of these applications is hereby incorporated in their entirety by reference.

FIELD OF THE INVENTION

The present invention relates to recombinant Factor C (rFC) of a horseshoe crab, produced in an insect cell system. The invention also relates to vectors for producing the protein by recombinant DNA methods and to methods for using the recombinant Factor C to detect endotoxins in a sample or for removal of endotoxins from a sample by affinity methods.

THE RELATED ART

The amoebocytes of horseshoe crabs contain an efficient coagulation cascade system which is activated by endotoxin, also known as lipopolysaccharide (LPS) from Gram negative bacteria. The enzymatic components of the coagulation cascade and the molecular events responsible for the subsequent gelation of the amoebocyte lysate have been characterized in *Tachypleus tridentatus*[1] and *Carcinoscorpius rotundicauda*[2,3,4]. Factor C has been shown to be the intracellular endotoxin-sensitive serine protease that initiates the coagulation cascade system[5].

By spiking, the Limulus amoebocyte lysate (LAL) test detects femtogram levels of LPS[6]. Owing to its extreme sensitivity, the amoebocyte lysate, in particular, the LAL has been developed into a commercial assay for widespread use in the detection of pyrogenic LPS in drugs and other pharmaceutical products[7,8]. This assay is based on the LPS-induced coagulation reaction of the lysate, culminating in formation of a gel clot. However, (a) the possible lack of specificity due to 1–3 β-D glucan and (b) the batch-to-batch variation in the sensitivity of commercial lysate to LPS, due to seasonal and geographical differences in the starting material[9] has prompted our laboratory to employ recombinant DNA technology to genetically-engineer Factor C as an alternative source of novel "limulus lysate" for endotoxin detection.

cDNAs encoding Factor C have been cloned[1,10,15]. There are six potential glycosylation sites in the amino acid sequence of the Factor C from *Carcinoscorpius rotundicauda* (CrFC)[10,15]. Cloned cDNA encoding CrFC has been expressed in *E. coli*[11] and also in yeast expression systems[12,24]. The rFC obtained from yeast was found to be immunoreactive and capable of binding LPS, although only limited amounts of rFC produced in yeast were soluble[13,14]. Also, it was found that LPS could not activate the enzymatic activity of yeast rFC, thus, a direct enzyme-based LPS detection is not possible using rFC produced in yeast[14].

Since the early 1970s, the diagnostic potential of LAL for endotoxemia has been recognized to be extremely important for timely and effective treatment. Thus, many studies have been conducted to improve the sensitivity of endotoxin assays by changing the formulation of the LAL and assay methodology[25]. Since blood (plasma) components interfere with the test, various methods to remove inhibition and/or enhancement have been developed. Furthermore, the LAL gelation clot method had been criticized as being subjective, semiquantitative and prone to variations in interpretations by different workers. Thus, advent of an improved fluorimetric assay for using LAL in LPS detection of plasma would be desirable. Even more desirable would be the compatibility of this assay for both LAL and a recombinant Factor C (rFC) in their sensitivity to LPS. Furthermore, this demonstrates the possible diagnostic utility of rFC for endotoxemia.

SUMMARY OF THE INVENTION

The present inventors believed that expression in insect cells rather than in a prokaryotic or simple eukaryotic expression system is suitable for producing rFC with full biological activity. Furthermore, horseshoe crabs and insects belong to the same phylum, Arthropoda, and so insect cells might more closely resemble the cells of the horseshoe crab than yeast cells in their physiology and biochemistry. Thus, rFC produced in insect cells might more closely resemble the protein as purified from the horseshoe crab and retain the bioactivity of having a serine protease activity activated by LPS.

The present invention relates to genetic engineering of a bioactive rFC, which unequivocally exhibits full biological functionality. It is capable of specifically recognizing and binding LPS and lipid A in both free and immobilized forms. Interference from 1–3 β-D-glucan, which switches on the alternate pathway in the coagulation cascade in conventional LAL, is not anticipated in assays of the present invention that use only Factor C as the LPS-binding, serine protease enzyme. Both the LPS-activated enzymatic assays of rFC and the enzyme linked immunosorbent assay (ELISA) lipid A binding assay could be formulated into a rapid high throughput mass screening test for LPS. Thus, a novel generation of "limulus amoebocyte lysate" has been invented, being capable of rapid and sensitive diagnosis and removal of subpicogram levels of endotoxin. The invention provides a standardized and convenient source of enzyme-based diagnostic reagent for detection of the ubiquitously contaminating endotoxin in pharmaceutical products. This inexhaustible supply of genetically-engineered Factor C can be easily standardized to circumvent batch-to-batch variations in sensitivity to LPS, a problem faced by the conventional LAL industry. Furthermore, the ability of the rFC of the invention to protect mice from endotoxemia, as well as its bacteriostatic activity, adds to its value in in vivo applications. Furthermore, the availability of rFC obviates the need for routine harvesting of the horseshoe crab for procurement of their amoebocyte lysate, and therefore, conserves this endangered "living fossil".

The present inventors have succeeded in expressing biologically active rFC using recombinant baculoviruses and other vectors appropriate for expression of heterologous DNA in insect host cells. The rFC obtained is enzymatically active. Thus, expression of rFC in insect cells is a convenient and economical source of rFC protein for use in rapid, sensitive, specific and quantitative determination of LPS in pharmaceutical products and other biological fluids.

Thus, the present invention comprises purified rFC that is enzymatically active. The phrase "enzymatically active" means that the Factor C protein has the biological activity of binding LPS or lipid A, being activated as to its serine protease activity upon LPS or lipid A binding. Enzymatically active rFC will induce coagulation of an amoebocyte lysate and will also cleave synthetic substrates such as, but not limited to, Boc-Val-Pro-Arg-MCA, Mu-Val-Pro-Arg-AFC and Boc-Val-Pro-Arg-pNA.

The present invention is also embodied in a method for producing substantially purified, enzymatically active rFC. The method comprises expressing DNA encoding a Factor C protein having the enzymatic activity described above in a culture of insect cells, then isolating the enzymatically active Factor C protein. The isolation preferably includes an ultrafiltration step. The purification preferably also includes a step of gel-filtration chromatography on a matrix having an exclusion limit of 100 kilodaltons. The gel filtration is preferably applied after the ultrafiltration. The exclusion limit of the gel filtration matrix can vary substantially; an effective matrix will provide at least about a 4-fold increase in the serine protease activity of an ultrafiltered crude preparation as measured by the fluorometric assay described herein.

The present invention also encompasses host-vector systems for expressing enzymatically active rFC. The host cells in these embodiments of the invention are insect cells, preferably leptidopteran cells. The vectors in these embodiments support replication of inserted DNA in insect cells and expression of heterologous DNA in insect cells. The vectors are preferably baculovirus or plasmid vectors. The heterologous DNA is sufficient to encode a Factor C enzyme of a horseshoe crab, preferably of the genus Carcinoscorpius, Tachypleus or Limulus. The recombinant Factor C will preferably at least have the LPS binding activity of Factor C and more preferably will have both LPS binding activity and serine protease activity. Preferred heterologous DNA is a polynucleotide having the sequence shown in SEQ ID NO:1 or SEQ ID NO:3.

The present invention is also embodied in assays for endotoxin comprising contacting a sample to be assayed for the presence of endotoxin or LPS or Lipid A with enzymatically active rFC according to the invention and measuring the serine protease activity of the rFC. The amount of serine protease activity of the rFC will reflect its activation due to binding of LPS or Lipid A or of another endotoxin known in the art to bind to Factor C of a horseshoe crab. The serine protease activity is conveniently measured by any method known in the art but is preferably measured by a chromogenic or fluorogenic method. In such a method formation of a product from a substrate by cleavage of the substrate by the serine protease activity of the rFC, resulting in a change in color or in fluorescence emission, is measured. Preferred substrates for such a chromogenic or fluorogenic assay are N-t-BOC-Val-Pro-Arg-MCA, Mu-Val-Pro-Arg-AFC and Boc-Val-Pro-Arg-pNA.

Additional embodiments of the invention include immunologic methods for assaying the presence of Lipid A or LPS or endotoxin in a sample. These methods of the invention rely upon binding of antibody that specifically binds to Factor C and subsequent detection or quantitation of the amount of the Factor C-antibody complex. In a preferred embodiment, the sample to be assayed is contacted with immobilized antibody that specifically binds to Lipid A or LPS or endotoxin as the ligand to form immobilized ligand. The immobilized ligand is then contacted with rFC according to the present invention to form immobilized rFC. Then the immobilized rFC is contacted with a second antibody that specifically binds the rFC. Finally, the presence or preferably the amount of the rFC-second antibody complex is determined. This determination can be performed by any method typical in the art such as a third antibody that binds the second antibody, perhaps through its Fc portion, or the like. In an alternate embodiment of this aspect of the invention, the second antibody is omitted and the enzymatic activity of the immobilized rFC is measured.

In another embodiment of the invention, the specific binding of LPS or lipid A to rFC is employed in a BIA-CORE™ assay (Pharmacia Biotech). By immobilizing the rFC on the substrate plate of the BIACORE™ apparatus, the presence of LPS or lipid A in a sample can be detected. Optimization of the amount of the rFC to be immobilized for a given load of LPS in a sample is considered within the skill of the ordinary practitioner. The BIACORE™ apparatus is operated in accord with the manufacturer's instructions.

Also, the present invention is embodied in methods for removal of endotoxin from a sample, wherein immobilized rFC is contacted with the sample, under conditions such that endotoxin in the sample binds the immobilized rFC, then the bound endotoxin is separated from the sample.

(1B) The pFastBac I™ vector and an intermediate CrFC subcdone of pGem11Zf(+)/CrFCEN were digested with Eco RI and Hind III. The liberated CrFCEN insert was ligated directionally into the linearized pFastBac I™ vector to yield pFastBac/CrFCEN. pFastBac/CrFCEN was then digested with Eco RI, as was another vector comprising DNA encoding Factor C, pGEM11Zf(+)/CrFCEE. The insert released from pGEM11Zf(+)/CrFCEE was ligated into the linearized pFastBac/CrFCEN. The clone having the proper orientation was selected by restriction analysis and designated pFastBac/CrFC21'.

FIGS. 2A–2D: Immunoblot analysis of Sf9 rFC. (2A) Reducing SDS PAGE of 5 μg total protein of cell lysate and culture supernatant harvested at 24 and 48 h post-induction (p.i.). (2B) Comparison of reducing and non-reducing SDS PAGE analyses of rFC from 72 h p.i. The results indicate that rFC is probably a double-chain form of Factor C as further proven by the LPS-treated (lane 2) and -untreated (lane 1) rFC under reducing (2C) and non-reducing (2D) conditions. Western Blots (FIGS. 2C and 2D) were developed sing a horseradish peroxidase system.

Figure 2:
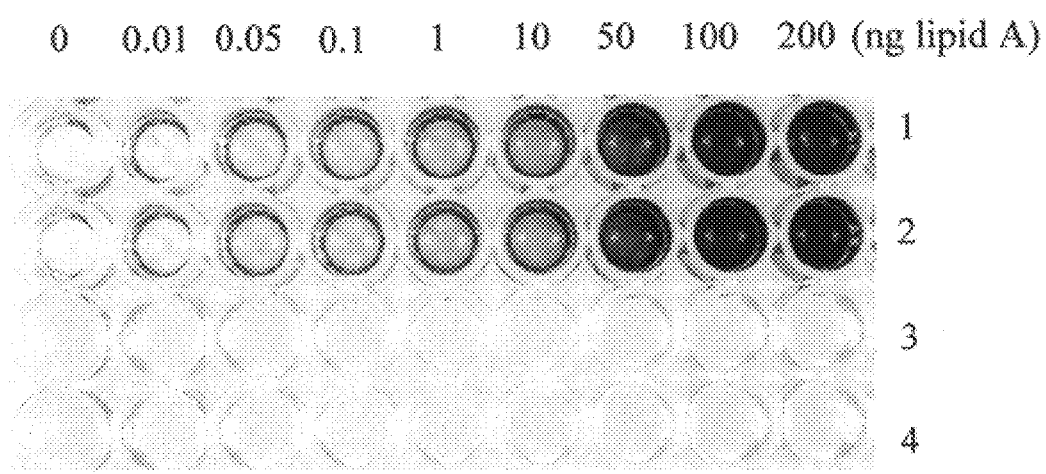

FIG. 2: ELISA lipid A-binding assay of rFC. A gradation of increasing intensity of color development of the enzymatically-hydrolyzed product is seen from 0.01 to 200 ng lipid A. Rows 1 & 2 contain 10 μg total protein per well of culture supernatant from pFastBac/CrFC21 infected Sf9 cells after 72 h p.i. Rows 3 & 4 are controls containing 10 μg total protein per well of culture supernatant from wild-type ACMNPV-infected Sf9 cells after 72 h p.i.

Figure 3A:
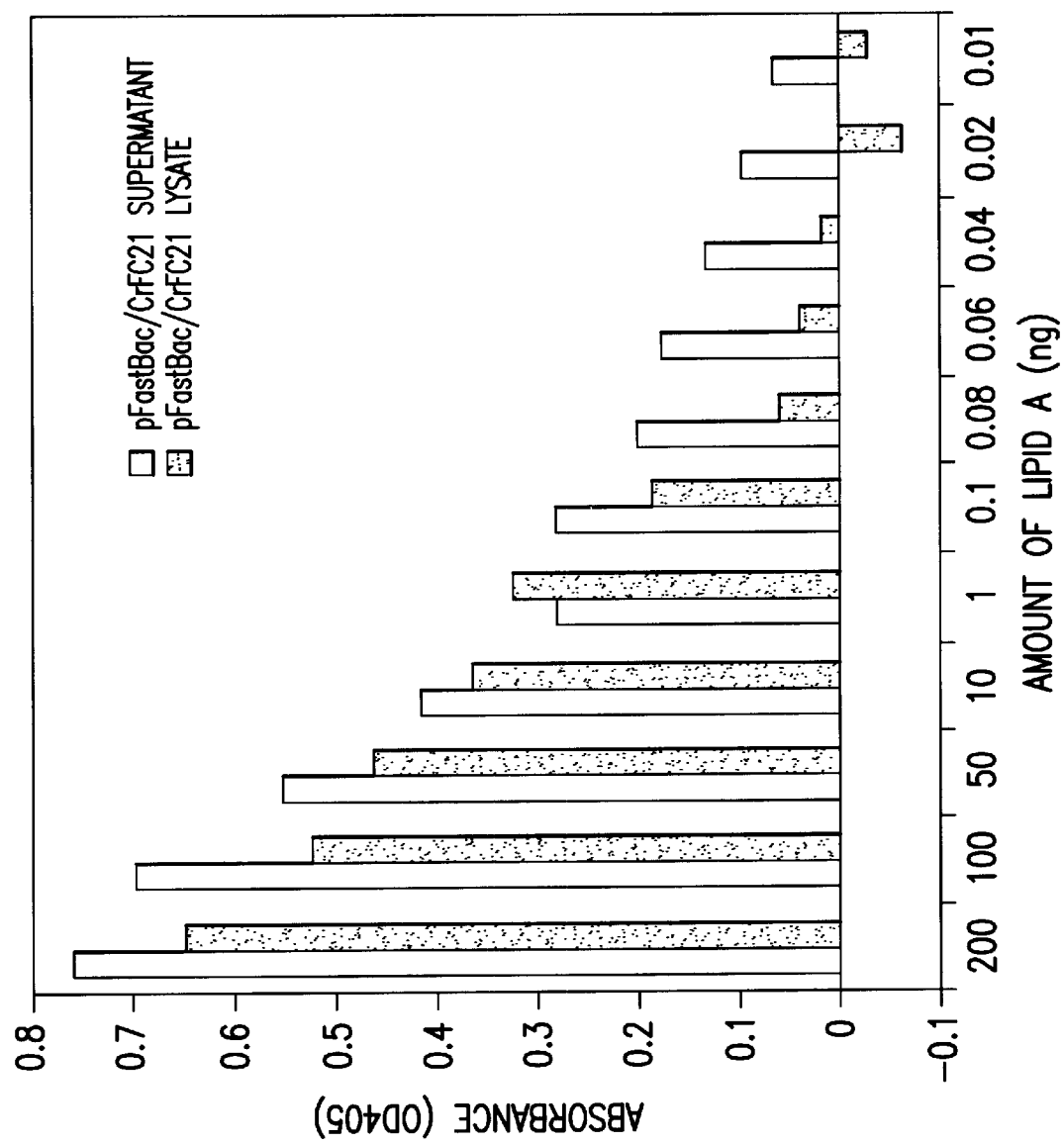
Figure 3B:
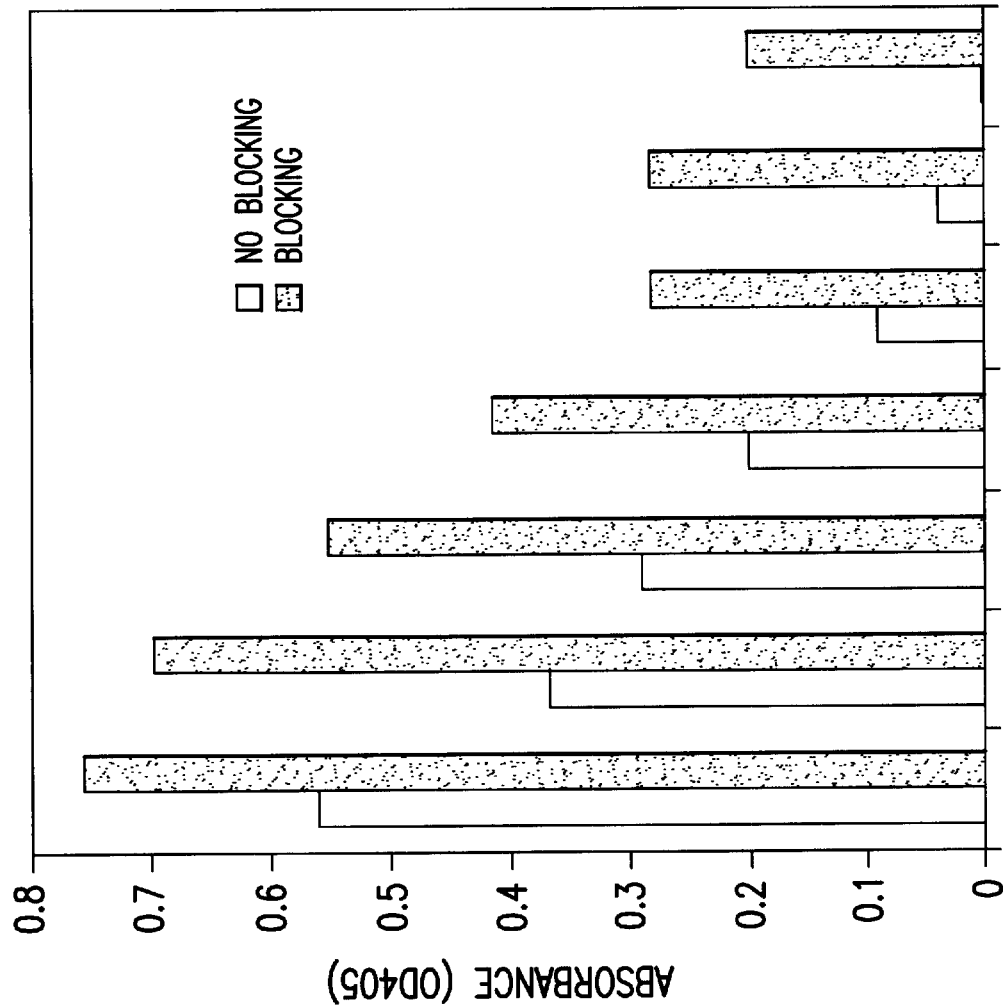

FIGS. 3A–3B: ELISA lipid A-binding assay of rFC. (3A), The histogram illustrates a quantification of the lipid A based on the absorbance at $OD_{405nm}$ of 72 h, culture supernatant (10 μg) and cell lysate (20 μg) after their reaction with 0.01 to 200 ng of lipid A. The results were normalized with wild type baculovirus infected samples. The culture supernatant consistently showed higher efficacy of binding lipid A even though a lower total amount of protein (10 μg) was used. (3B) Blocking of excess sites with 0.2% BSA effectively removed the non-specific background binding and results, in higher net absorbance readings.

Figure 4:
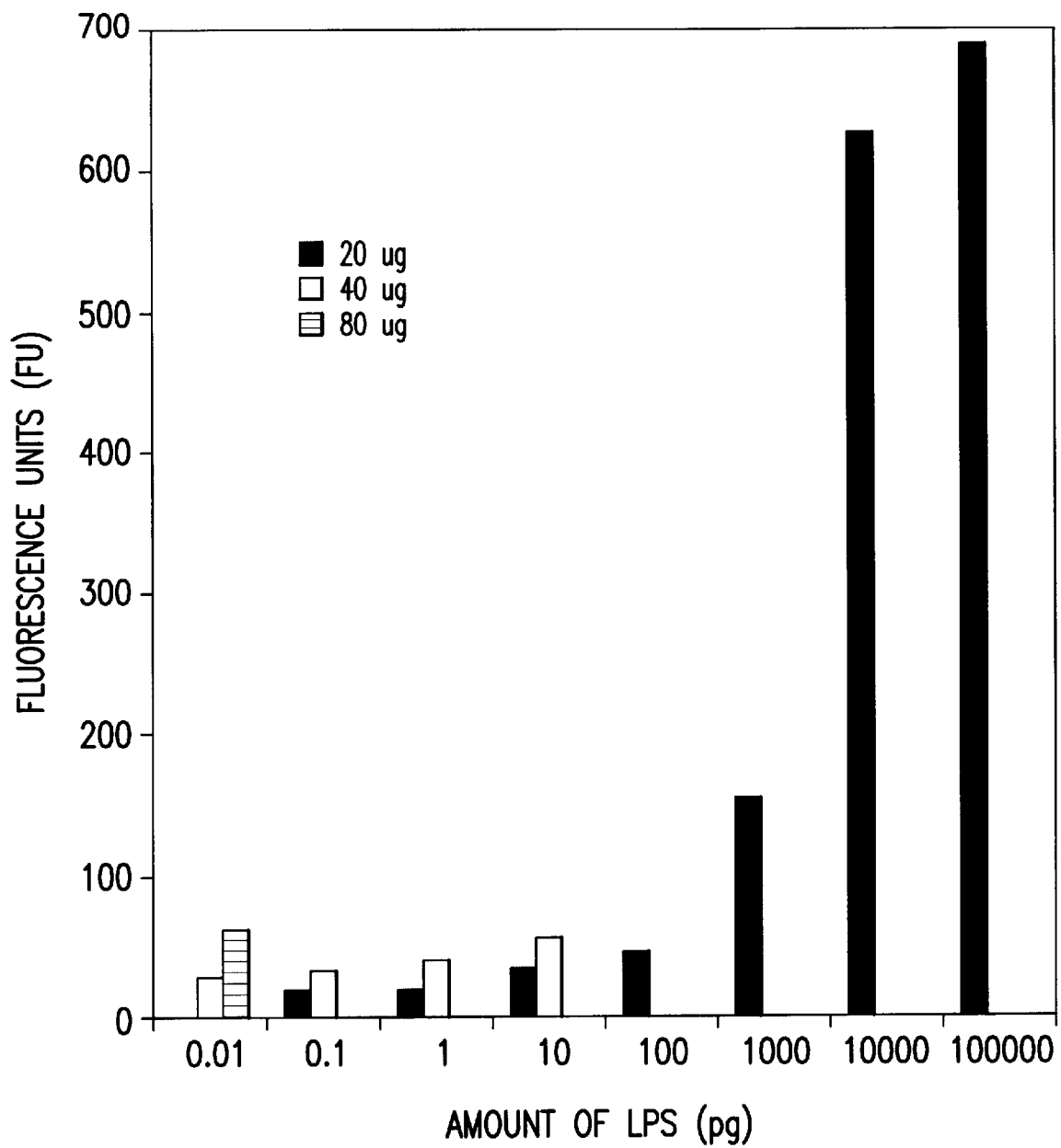

FIG. 4 : Biological Activity of BIOMAX™ purified rFC. The rFC was enriched by BIOMAX™-50 ultrafiltration and this protein sample was reacted with a range of absolute amounts of LPS (0.01–10 000 pg). Both 40 and 80 μg amounts of rFC showed enzymatic activity with 0.01 pg LPS.

Figure 5:
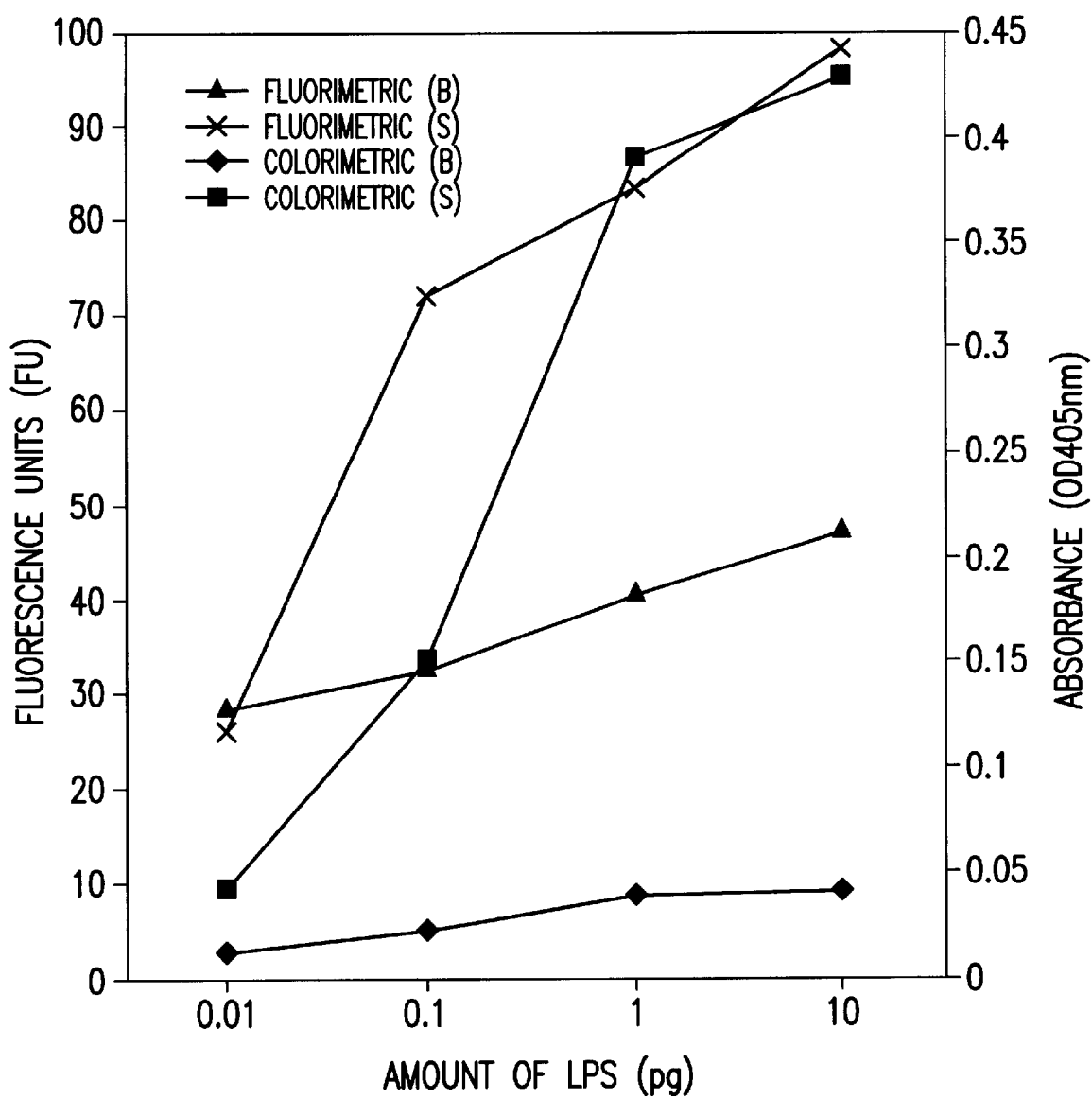

FIG. 5: Fluorimetric and calorimetric assays of LPS using purified rFC. In both the fluorimetric and calorimetric assays, further purification of BIOMAX™-purified rFC by SEPHADEX™ G-100 dramatically improved the sensitivity of rFC to LPS. The conventional tube method of fluorimetric assay was compared with the microcolorimetric assay for both the BIOMAX™ sample (B) and SEPHADEX™ G-100 purified sample (S). Amounts of rFC used were 40 μg and 100 μg for the fluorimetric and calorimetric assays, respectively.

Figure 6:
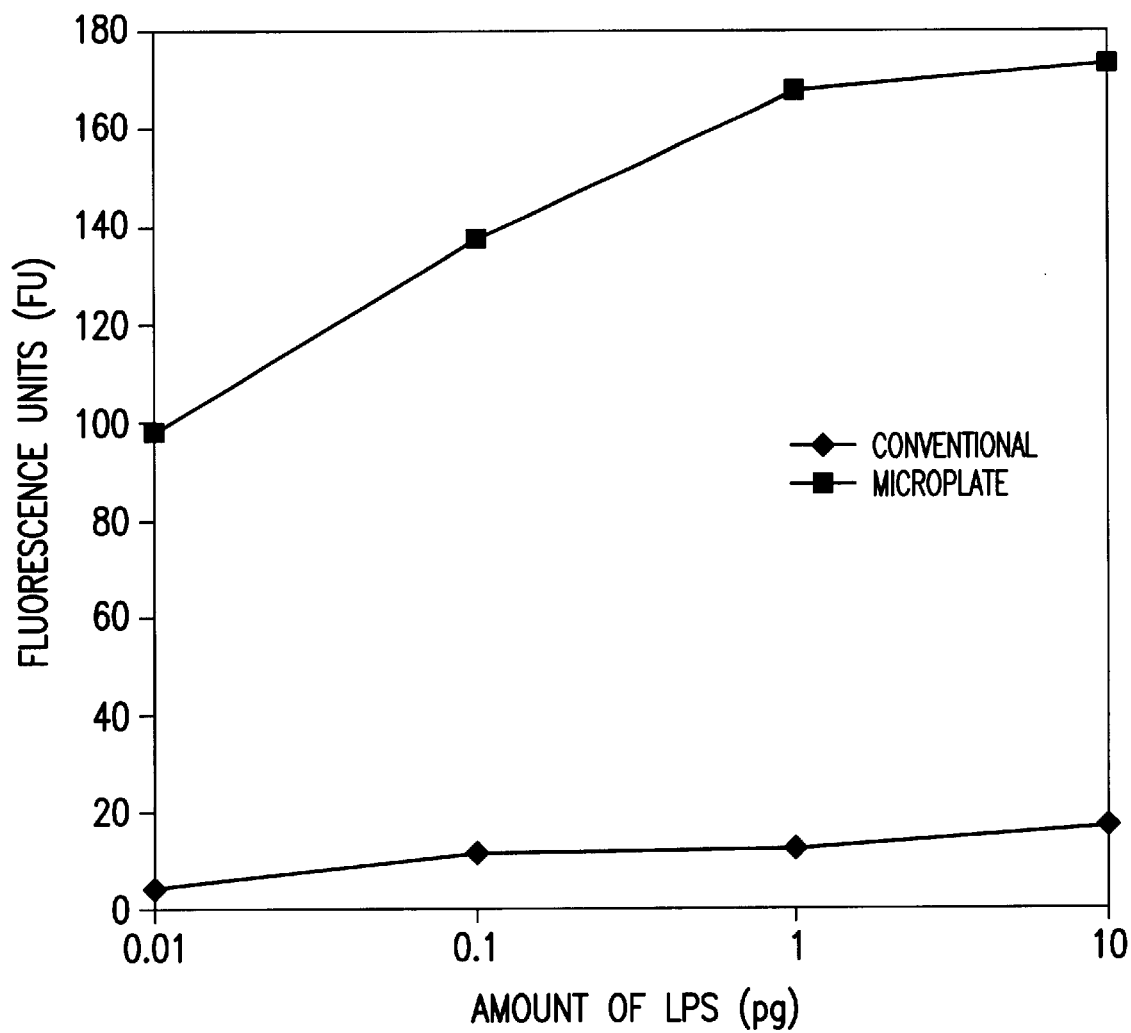

FIG. 6: Comparison of tube and plate fluorimetric assays. A comparison of the fluorescence readings was made between the conventional tube method and the microtiter plate method using 40 μg of the SEPHADEX™ G-100 purified rFC.

Figure 7:
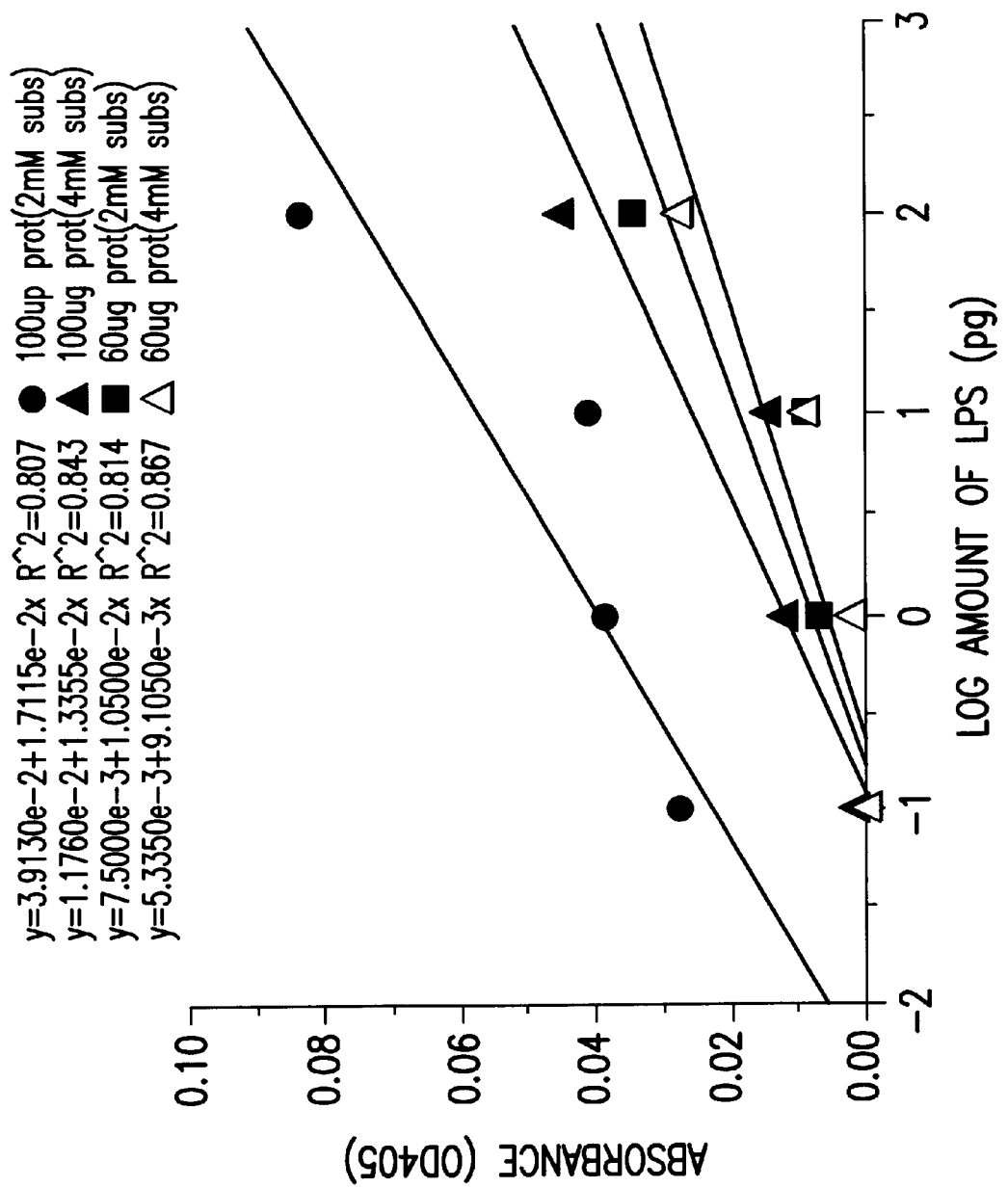

FIG. 7: Colorimetric assay for LPS-induced Factor C enzyme activity of rFC. A comparison is made of the amounts of culture supernatant proteins (60 and 100 μg) containing rFC, and the concentrations (2 and 4 mM) of the calorimetric substrate, Boc-Val-Pro-Arg-pNA. It is observed that as low as 0.01 pg endotoxin was optimally detected with 100 μg culture supernatant at 2 mM pNA substrate.

Figure 8:
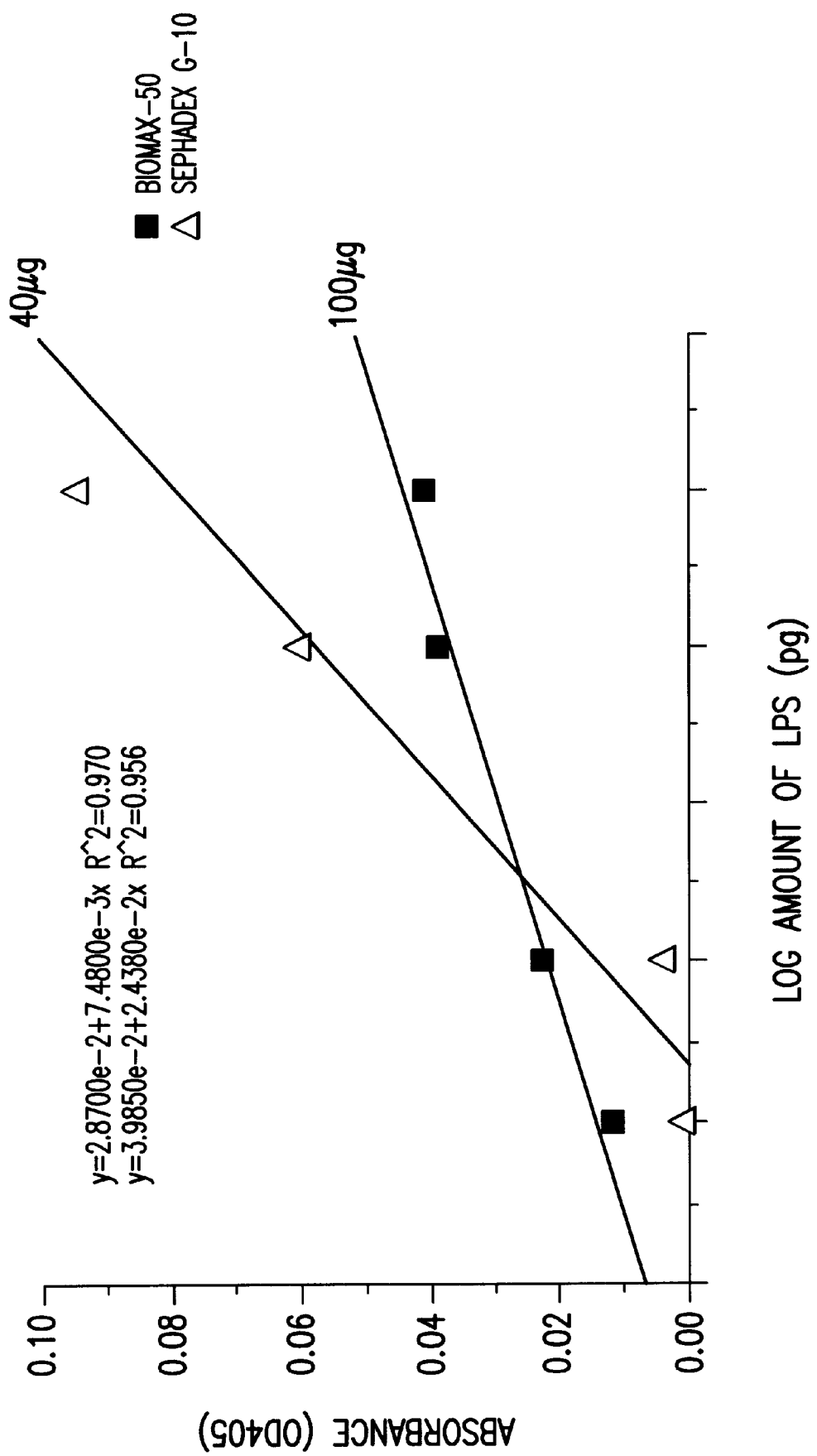

FIG. 8: Colorimetric assay of LPS using purified rFC. Similar to the fluorimetric assay, the calorimetric test also showed that the SEPHADEX™ G-100 purified rFC exhibited improved sensitivity to LPS, where 40 μg of purified rFC (instead of 100 μg of BIOMAX™-purified rFC) was sufficient to detect subpicogram levels of LPS.

Figure 9:
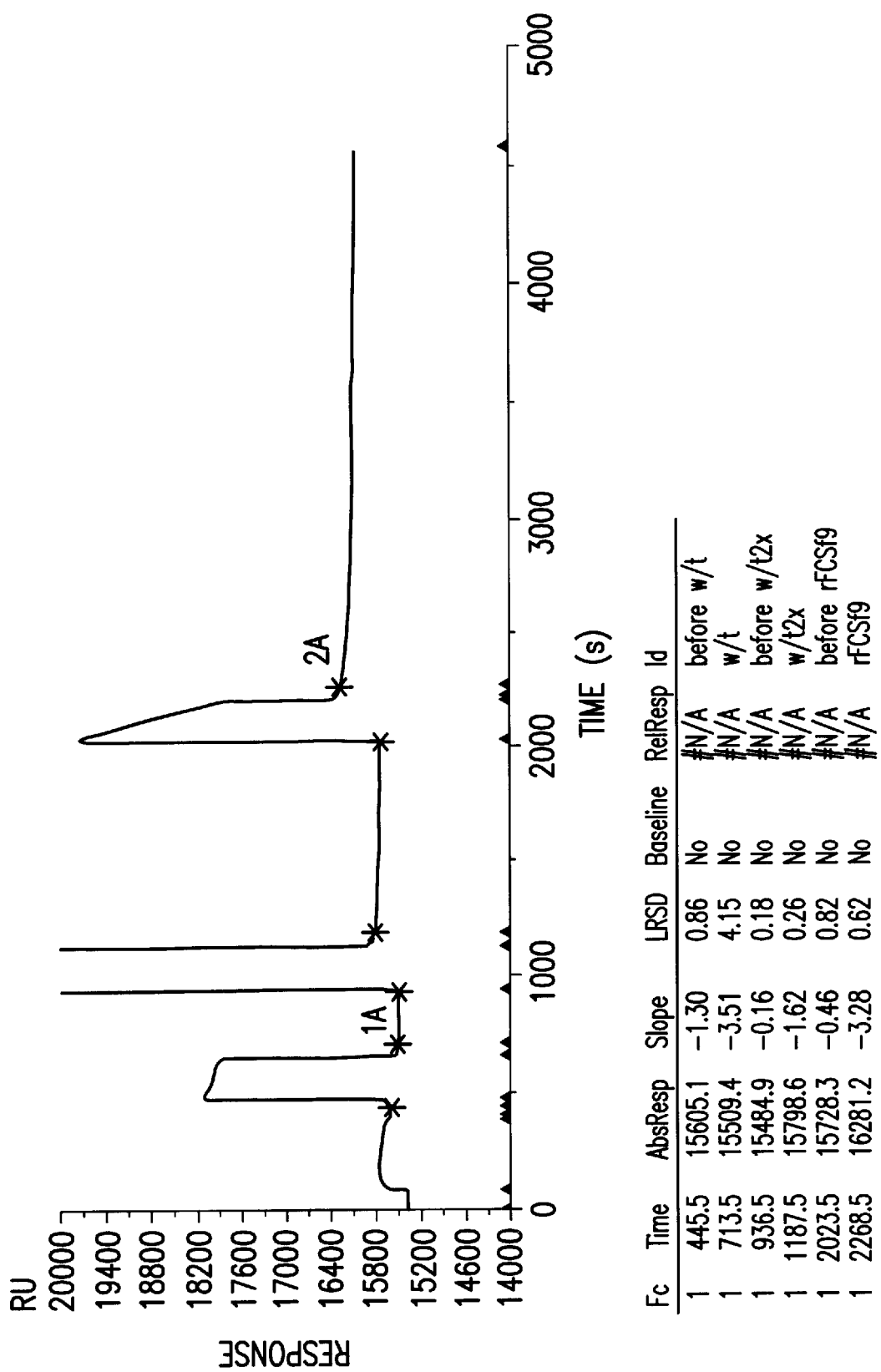

FIG. 9: Binding of rFC to lipid A assayed by BIACORE™ bioassay. Binding between rFC produced from pFastBac/CrFC21 and immobilized lipid A (*E. coli* D31m4) was assayed using the BIACORE™ X biosensor (Pharmacia Biotech). BIOMAX™ and SEPHADEX™ G-100 purified supernatants of cultures of Sf9 cells infected with wild-type baculovirus did not show any background binding to the immobilized lipid A (plateau 1A). On the other hand, the rFC from the culture supernatant of Sf9 cells infected with pFastBac/CrFC21 specifically bound the immobilized lipid A with a net activity of 553 Response Units (plateau 2A). The protein samples, each at 1 mg/ml, were injected at 10 μl/min for 3 minutes over the ligand monolayer that was previously immobilized on a HPA chip[14].

Figure 10:
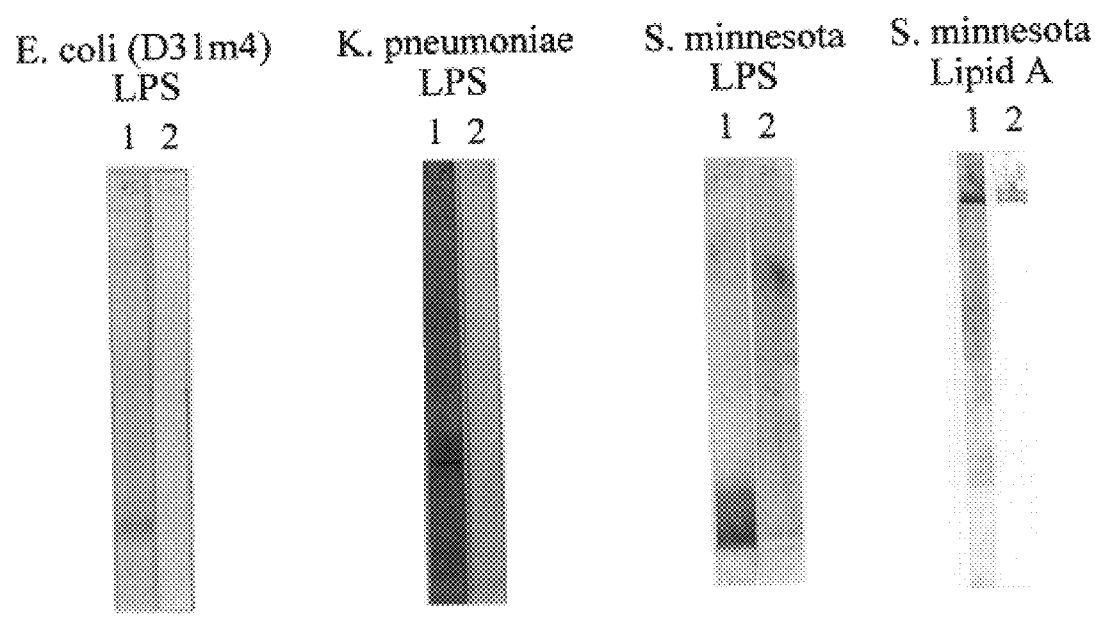

FIG. 10: rFC from Baculovirus binds LPS and lipid A from several Gram negative bacterial species. LPS from three different species of bacteria, *E coli*, *K. pneumoniae*, and *S. minnesota*, and lipid A from *S. minnesota*, were separated by electrophoresis and electroblotted onto an Immobilon™ PVDF membrane. Each LPS/lipid A strip was incubated with rFC from pFastBac/CrFC21 (lane 1) or control culture supernatant from wild-type AcMNPV-infected Sf9 cells (lane 2). The results show that rFC binds LPS/lipid A from different species of Gram negative bacteria.

Figure 11:
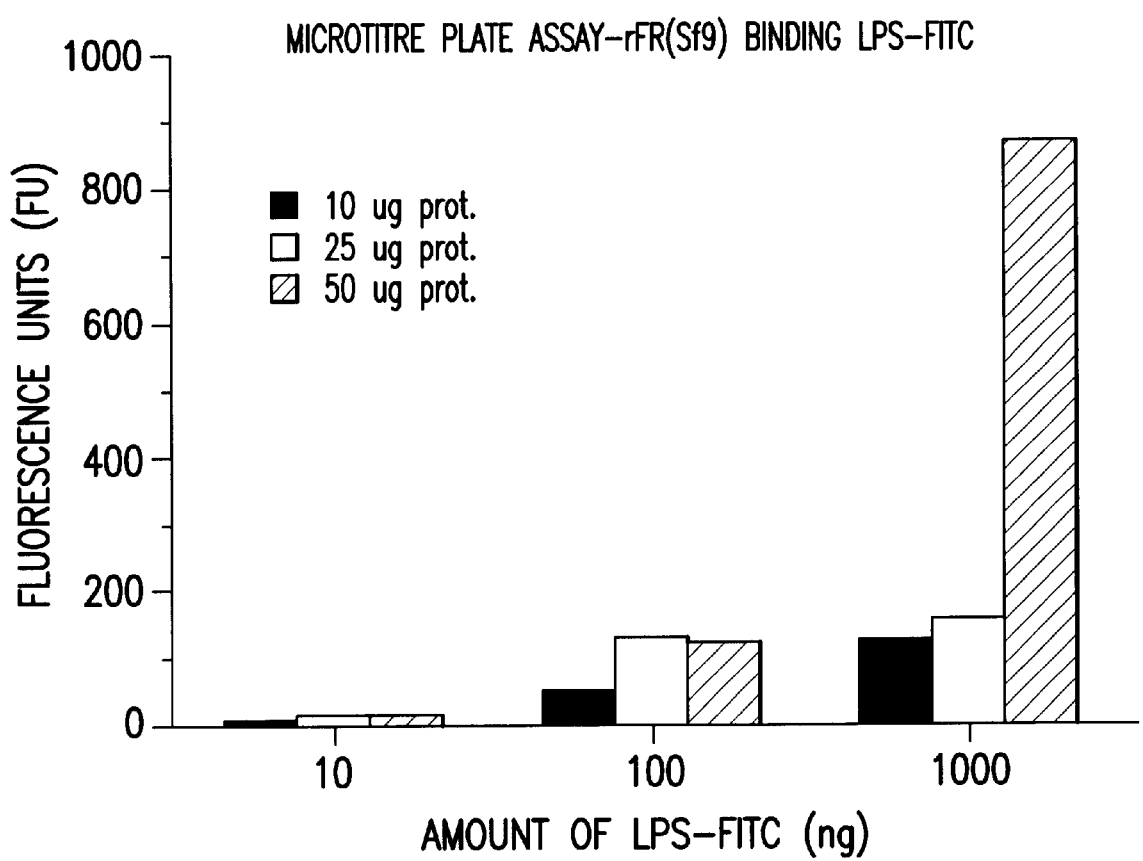

FIG. 11: Microtiter plate-immobilized rFC for detection and removal of LPS. 10, 25 or 50 μg of partially-purified protein containing rFC derived from baculoviral system (rFC Sf9) immobilized on a 96-well microtiter plate was capable of specifically recognizing and binding subpicogram levels of FITC-conjugated LPS. The efficacy of binding/detection of a range of LPS by various amounts of rFC protein immobilized onto the microtiter plate is shown.

Figure 12:
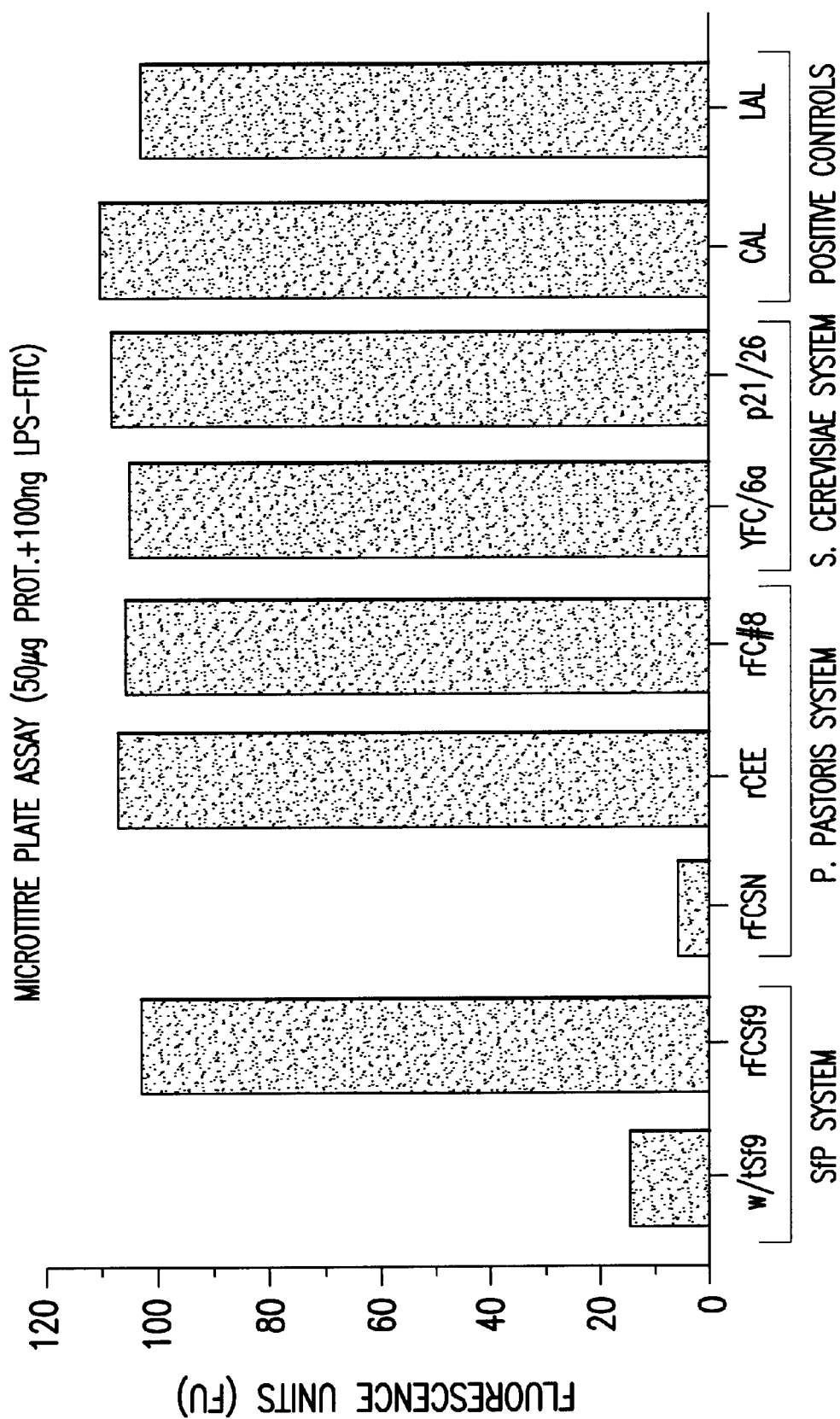

FIG. 12: Microtiter plate-immobilized rFC from various yeasts binds to LPS. Immobilized rFC derived from yeast (*P. pastoris*: rFC#8 {pHILD2/CrFC21} and rFCEE {pHILD2/CrFC21EE}; *S. cerevisiae*: YFC/6a {YepSecl/CrFC26Δ6a} and P21/26 {pEMBLyex4/CrFC21/26}). Native Factor C in Carcinoscorpius amoebocyte lysate, LAL (50 μg protein) were used as positive controls. There is consistency in the efficiency of recognition of LPS-FITC and its binding to the immobilized rFC. The negative controls were w/tSf9 (wild-type Sf9 cells infected with AcMNPV DNA alone) and rFCSN (rFC derived from a control yeast recombinant clone devoid of the LPS binding domain).

Figure 13:
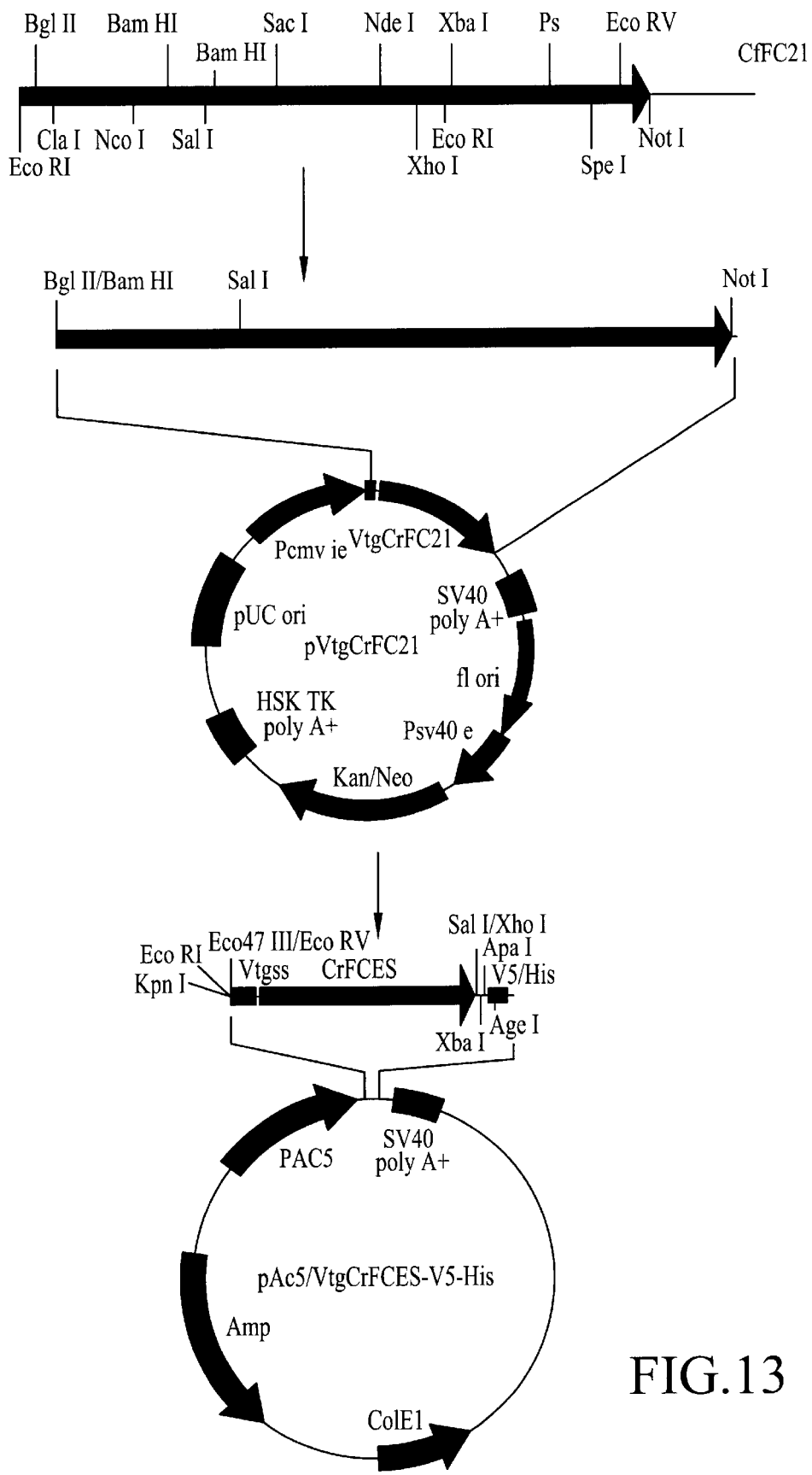

FIG. 13: Construction of pAc5/VtgCrFCES-V5-His. The full-length CrFC 21 cDNA was released by a Bgl II and Not I double digest. The released fragment was subcloned into the Bam HI and Not I sites of VtgEGFP. Consequently, the Bgl II/Bam HI site is destroyed. Then the LPS-binding domain of CrFC21 was released by digestion with Eco47 III and Sal I (cutting an internal site). The fragment was subcloned into the Eco RV and Xho I sites of pAc5/V5-HisA to give pAc5/VtgCrFCES-V5-His. Both Eco47 III/Eco RV and Sal I/Xho I sites are destroyed. FIG. 14: Map of pAc5/VtgCrFCES-V5-His. FIG. 14A shows the amino acid and nucleotide sequences at the junction of the vitellogenin signal sequence (Vtgss) and the CrFCES cDNA. FIG. 14B shows the complete map of the vector. The Vtgss portion of the construct is described in detail in co-pending application Ser. No. 60/106,426. The nucleotide junctions were determined by sequencing using the Ac5 forward primer and pcDNA3.1/BGH reverse primer. The CrFCES is cloned in-frame with respect to Vtgss (at the 5' end) and V5-His (at the 3' end). The secreted VtgCrFCES protein was also purified via affinity chromatography (Talon™, Clontech) under denaturing conditions (6M urea, 250 mM NaCl and 20 mM sodium phosphate buffer, pH7.0). The protein was transferred to a PVDF membrane in transfer buffer (10% methanol, 10 mM CAPS, pH 11.0) and its N-terminal amino acid sequence determined. Using the Vtgss secretory signal, only a single cleavage point was identified (indicated by the arrow). Thus, Vtgss allows the homogenous production of secreted eterologous recombinant protein.

Figure 15A:
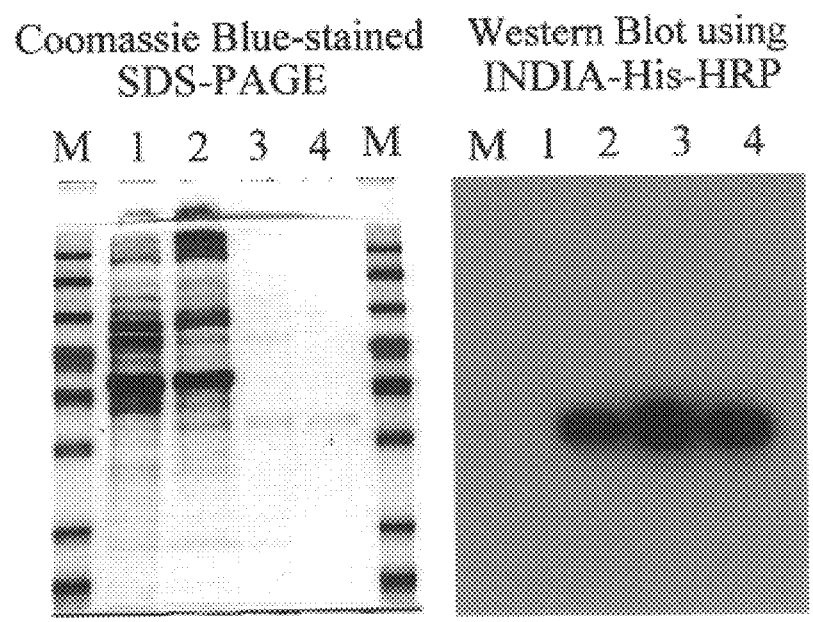
Figure 15B:
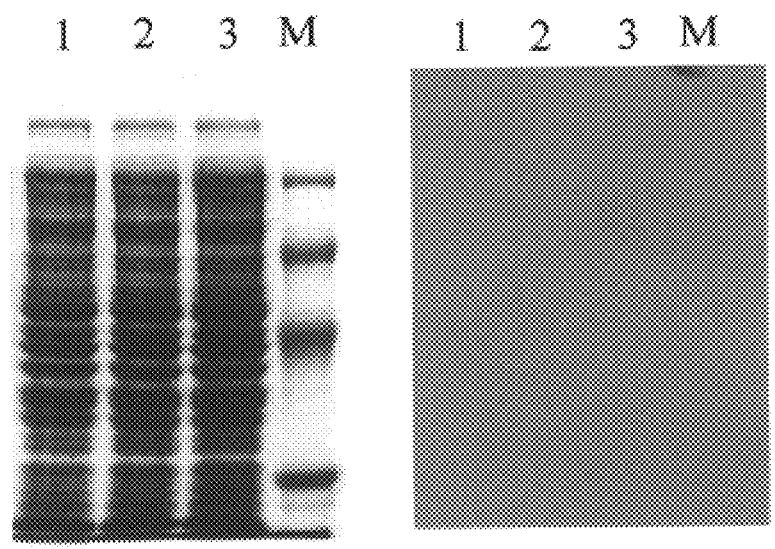

FIGS. 15A–15B: Distribution of secreted VtgCrFCES protein.
15A—culture medium
Lane M: Benchmark™ prestained marker
Lane 1: control medium (30 μg)
Lane 2: VtgCrFCES medium (not purified 30 μg)
Lane 3: VtgCrFCES (affinity purified; 1 μg)
Lane 4: VtgCrFCES (ISOprime purified; 1 μg)
Left panel, Coomassie Blue-stained gels; right panel, Western blotting using INDIA-His-HRP.
15B—cell lysate;
Lane M: Bio-rad prestain marker
Lane 1: control cell lysate (30 μg)
Lane 2: VtgCrFCES cell lysate (transient; 30 μg)
Lane 3: VtgCrFCES cell lysate (stable; 30 μg)
Left panel, Coomassie Blue-stained gels; right panel, Western blotting using INDIA-His-HRP.

The VtgCrFCES (hereinafter "VtgCrFCES") protein was effectively secreted into the culture medium, as verified by SuperSignal HisProbe™ Western Blotting Kit (Pierce). The secreted VtgCrFCES was purified to homogeneity by isoelectric focusing (ISOprime™, Hoeffer) resulting in a single protein band having a molecular weight identical to that of the protein isolated by affinity column chromatography. The ISOprime™-purified protein was not denatured even when purified in pyrogen-free water. No VtgCrFCES was detected in the cell lysate. The purification process was made easy and more effective by the presence of VtgCrFCES in the culture medium.

Figure 16:
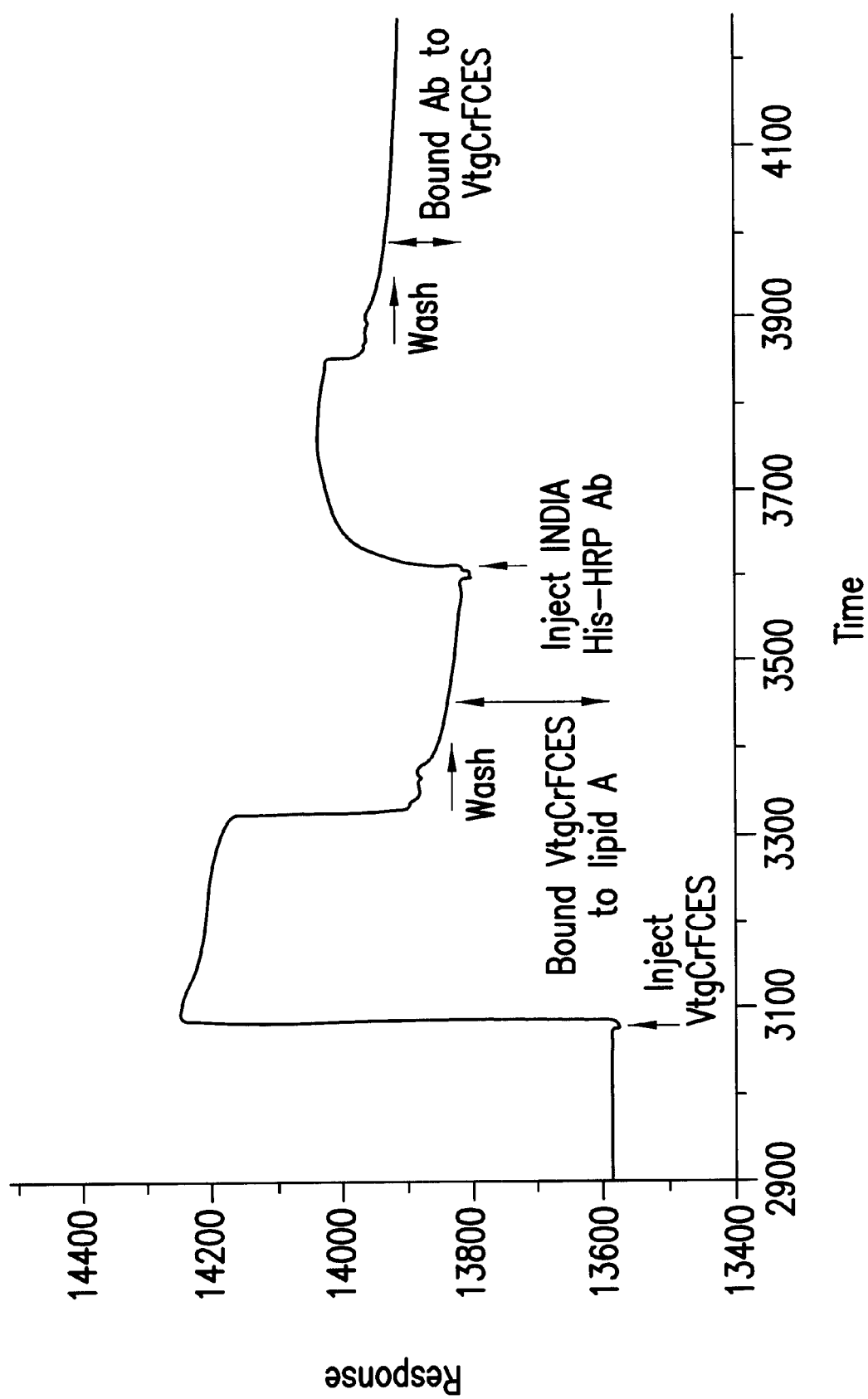

FIG. 16: Lipid A binding properties of ISOprime™-purified VtgCrFCES. Immobilization of lipid A to the HPA sensor chip has been described earlier (14).

Figure 17:
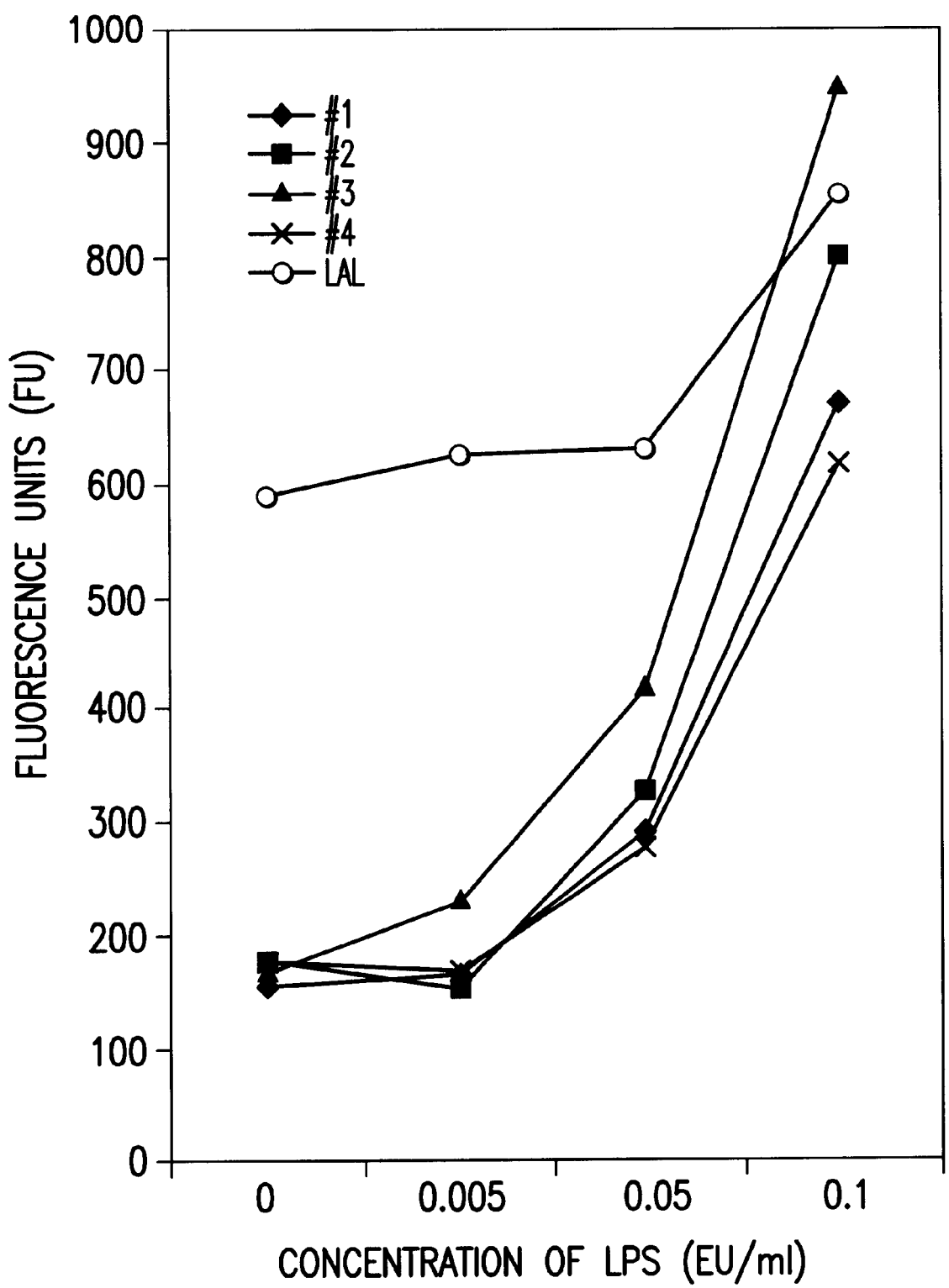

FIG. 17: FIG. 17 shows a plot of the fluorescence units (FU) of the product of the Factor C enzymatic reaction after 10 µg of LAL or rFC was pre-activated by increasing amounts of LPS. The microfluorimetric detection of a range of concentrations of LPS by LAL in comparison to rFC from different production batches (Nos. 1, 2, 3 and 4) is shown.

Figure 18A:
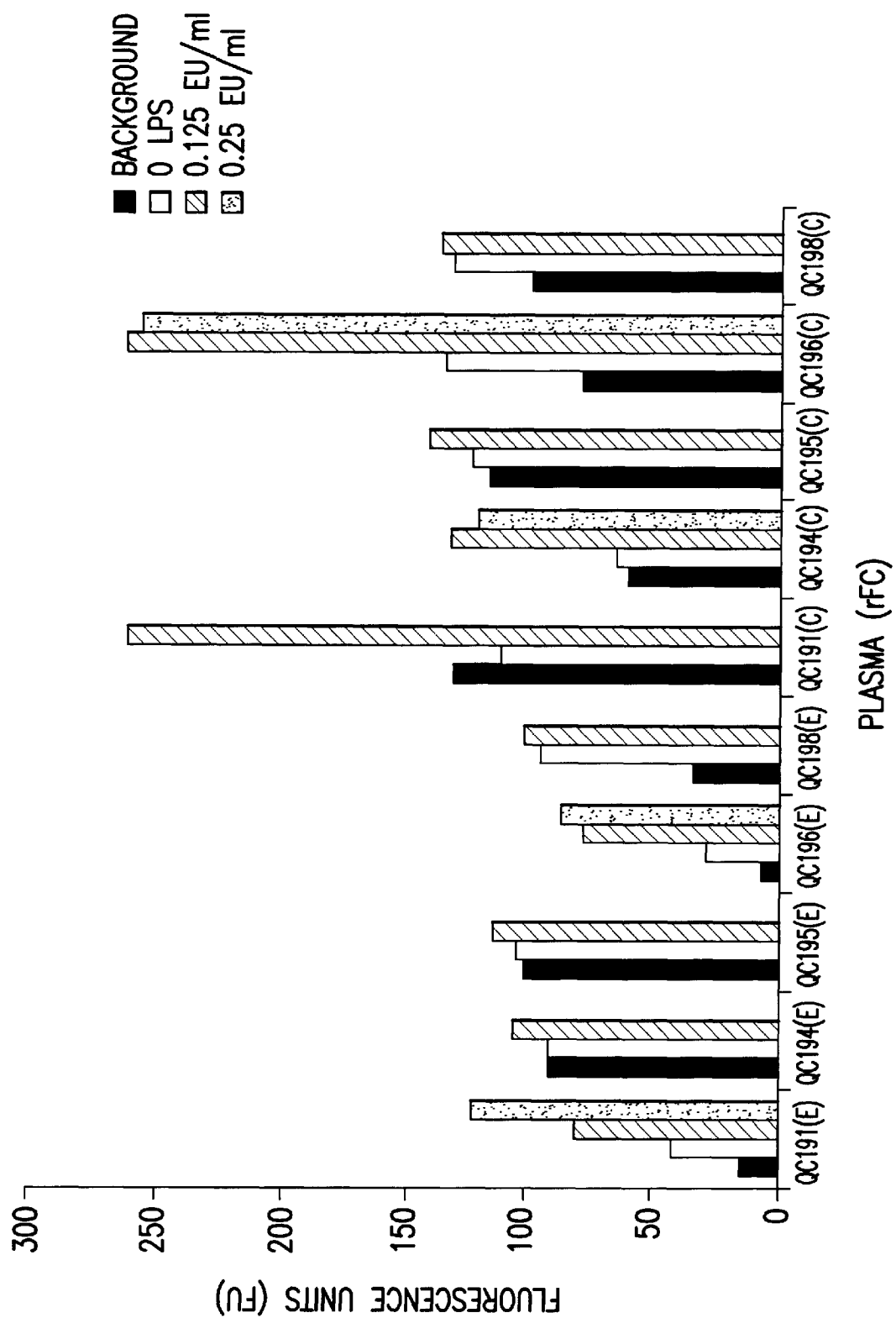
Figure 18B:
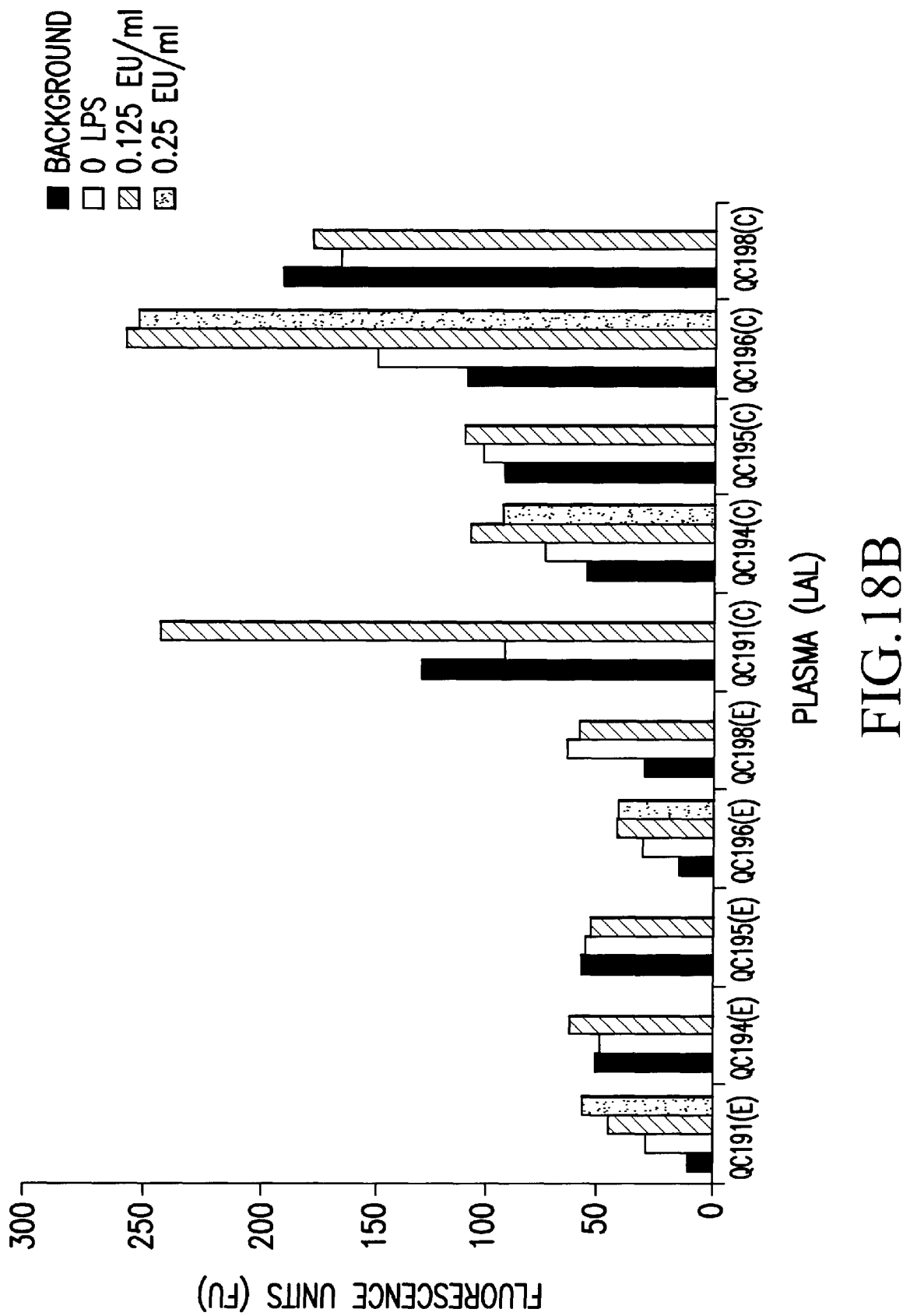

FIGS. 18A–18B: FIGS. 18A and 18B: Use of rFC (18A) and LAL (18B) in microfluorimetric detection of LPS in spiked human cord blood. Cord blood was apyrogenically obtained in either EDTA (E) or citrate (C) buffer as anticoagulants. Replicates of each plasma sample were spiked with 0.125 or 0.25 EU/ml of LPS prior to their use in the microfluorimetric assay. The background shows unspiked plasma assayed in the absence of substrate. This is to test for the background level of fluorescence that may be given off by the endogenous components of the plasma. The 0 LPS was used as a negative control to compare with the LPS-inducibility of Factor C in the rFC when tested with the other two LPS-spiked plasma.

Figure 19A:
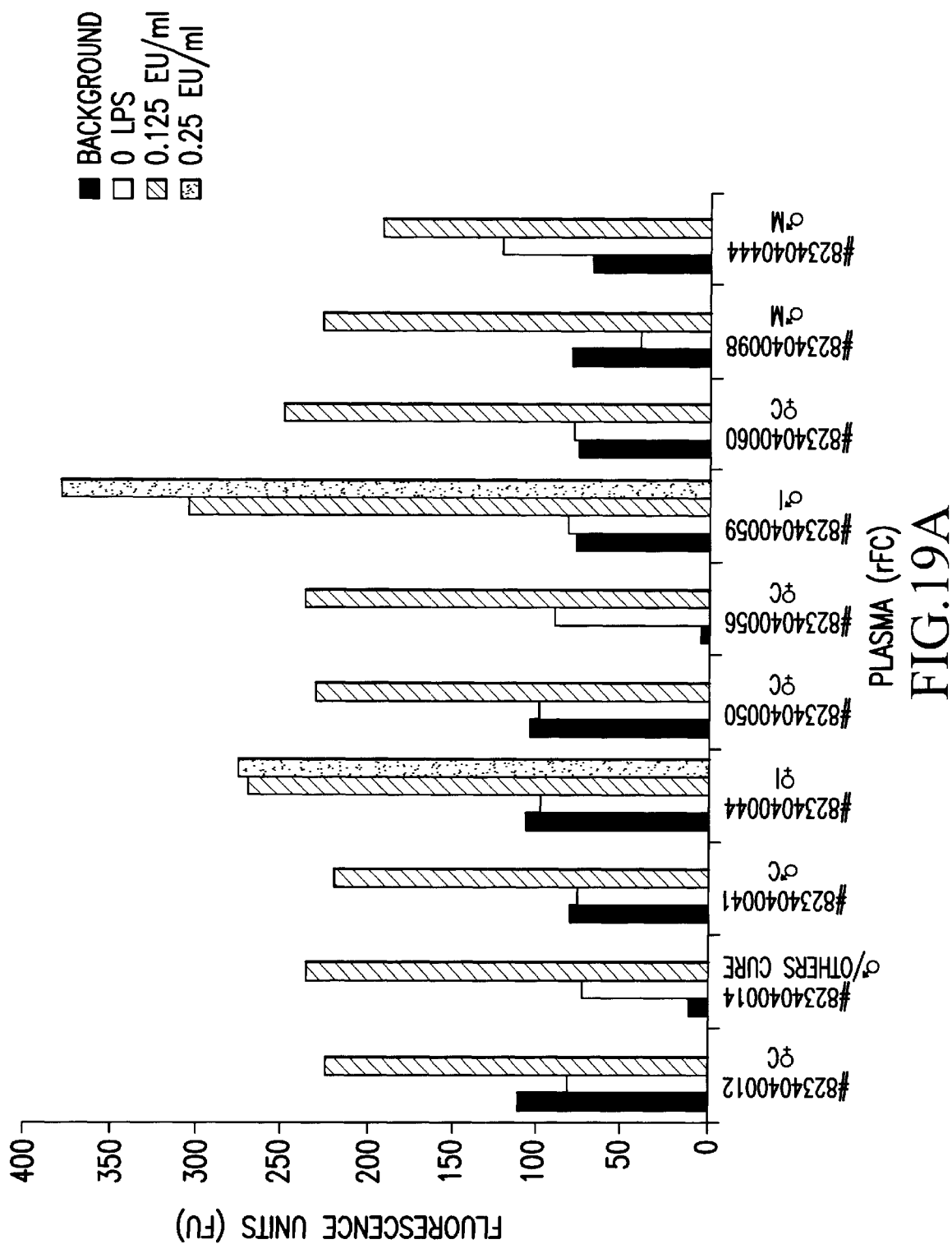

FIGS. 19A–19B: Use of rFC (19A) and LAL (19B) for detection of LPS in 2-day old citrated human plasma. A visibly good correlation can be seen in the sensitivity of detection by rFC and LAL.

Figure 20A:
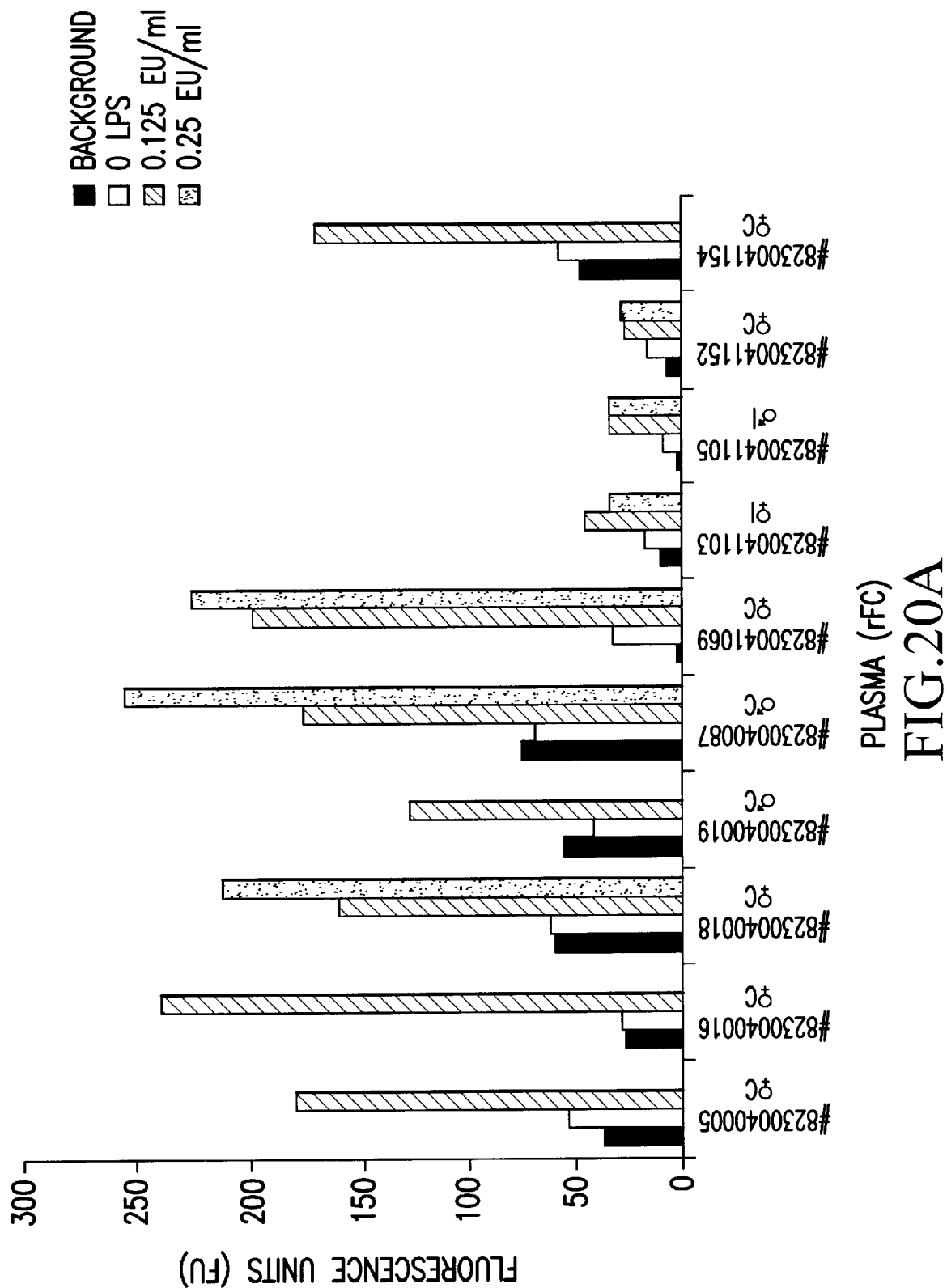
Figure 20B:
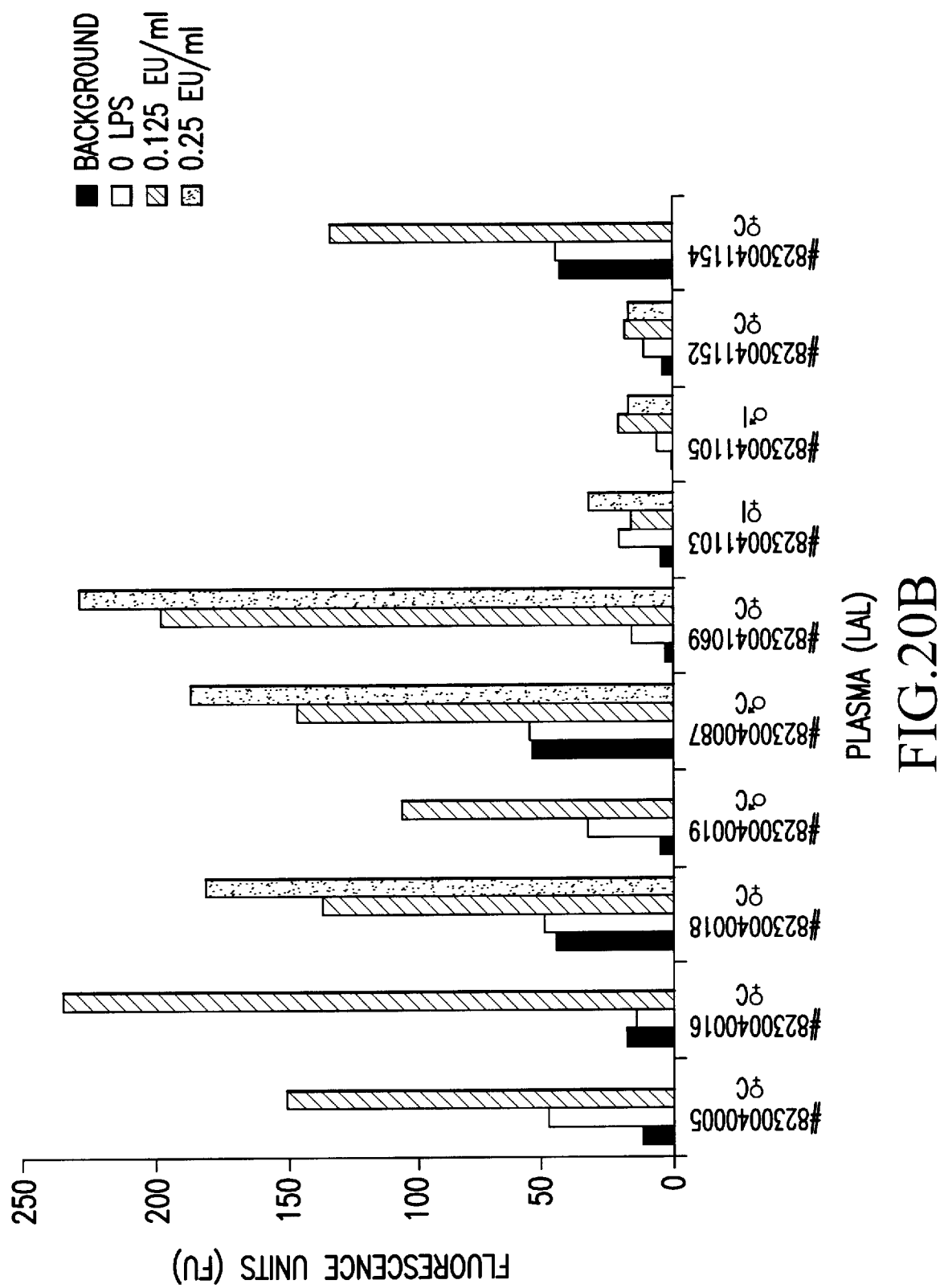

FIGS. 20A and 20B: Use of rFC (20A) and LAL (20B) for detection of LPS in 7-day old citrated human plasma. A visibly good correlation can be seen again in the sensitivity of detection by rFC and LAL. Aging of the plasma samples at 4° C. did not appear to affect the microfluorimetric assay for LPS.

DETAILED DESCRIPTION OF THE INVENTION

The present application relates to rFC of the horseshoe crab.

A preferred horseshoe crab that can serve as a source of DNA or mRNA for producing the rFC of the invention is *Carcinoscorpius rotundicauda* (CrFC). The present invention relates especially to expression of rFC by means of baculovirus host-vector systems. The present application also relates to a fluorometric assay for endotoxin that makes use of the rFC expressed by recombinant DNA methods.

cDNAs encoding Factor C proteins from *Carcinoscorpius rotundicauda* have been previously described[10,15]. rFC from *Carcinoscorpius rotundicauda* (rCrFC) has been produced in vitro by coupled transcription/translation systems[10,15]. However, the present invention resides partly in the development of in vivo systems, especially using insect cells as the host cell, for efficient production of rFC by expression of cloned DNA.

Also, the protection of rFC from activation and subsequent self-proteolysis by binding of endotoxin which may be present in solutions used in isolation of the protein is described in reference 15. Basically, dimethylsulfoxide (Me$_2$SO, DMSO) is added to solutions which are used during the purification process. Even greater protection of the rFactor C is achieved by also adding an agent effective for chelating divalent metal ions to the purification solutions.

cDNAs appropriate for expression in the presently-described system can be cDNAs encoding Factor C of any horseshoe crab. Two representative nucleotide sequences are presented as SEQ ID NO:1 and SEQ ID NO:3 (encoding the amino acid sequences of SEQ ID NOs:2 and 4). A composite DNA sequence, assembled from incomplete cDNA fragments, encoding the Factor C of *Tachypleus tridentatus* is disclosed by Muta et al.[1]

For use in the LPS binding assays and LPS removal according to the invention, the Factor C can be produced by any method typical in the art, but is preferably made in a eukaryotic host cell. Production of rFC in yeast host-vector systems is described in reference 16. As it has been the Inventors' recent experience that Factor C produced in yeast lacked serine protease activity, rFC for use in enzymatic activity-based assays is preferably produced by a baculovirus host-vector system.

"Stringent conditions" for hybridization are those that provide for hybridization of sequences having less than 15% mismatch, preferably less than 10% mismatch, most preferably 0% to 5% mismatch. Exemplary of such conditions, using probes of 50 bases or longer, are an aqueous solution of 0.9 M NaCl at 65° C.; an aqueous solution of 0.98 M NaCl, 20% formamide at 42–45° C. The conditions will vary according to the length of the probe, its G+C content and other variables as known to the skilled practitioner[11]. Exemplary wash conditions following hybridization are an aqueous solution of 0.9 M NaCl at 45–65° C., preferably 55–65° C. Lower salt, or addition of an organic solvent such as formamide, in the wash buffer will increase the stringency of the condition as known in the art.

A preferred hybridization condition is at 42° C. in 50% formamide, 5×SSC, 1×Denhardt's solution, 20 mM phosphate buffer, pH 6.5, 50 µg/ml calf thymus DNA, 0.1% SDS. Salt and temperature conditions equivalent to the hybridization conditions employed can be calculated from the following equation[18]:

$$T_m = 81.5° C. - 16.6(\log_{10}[Na^+]) + 0.41(\%G+C) - 0.63(\%formamide) - (600/l),$$

where /l=the length of the hybrid in base pairs.

A preferred washing condition is in 1×SSC, 0.1% SDS washing solution at room temperature, followed by washing at high stringency with 0.1×SSC, 0.1% SDS at 42° C. and 2× with 0.1× SSC/0.1% SDS for 15 min. each at 42° C.

EXAMPLE 1

Recombinant Constructs of CrFC cDNA in a Baculovirus Expression Vector

Plasmids and Sf9 Cell Culture

Sf9 insect cells were maintained as a monolayer culture in serum-free SF 900 II SFM medium supplemented with 50 U/ml penicillin and 50 µg/ml streptomycin (Life Technologies, Inc.) in a humidified incubator (Forma, USA) at 27° C. The plasmid pFastBac I™ and the competent DH10Bac *E. coli* were from Life Technologies, Inc., USA. Construction of pFastBac/CrFC21, Transposition Into *E. coli* and Transfection Into Sf9 Insect Cells.

Figure 1A:
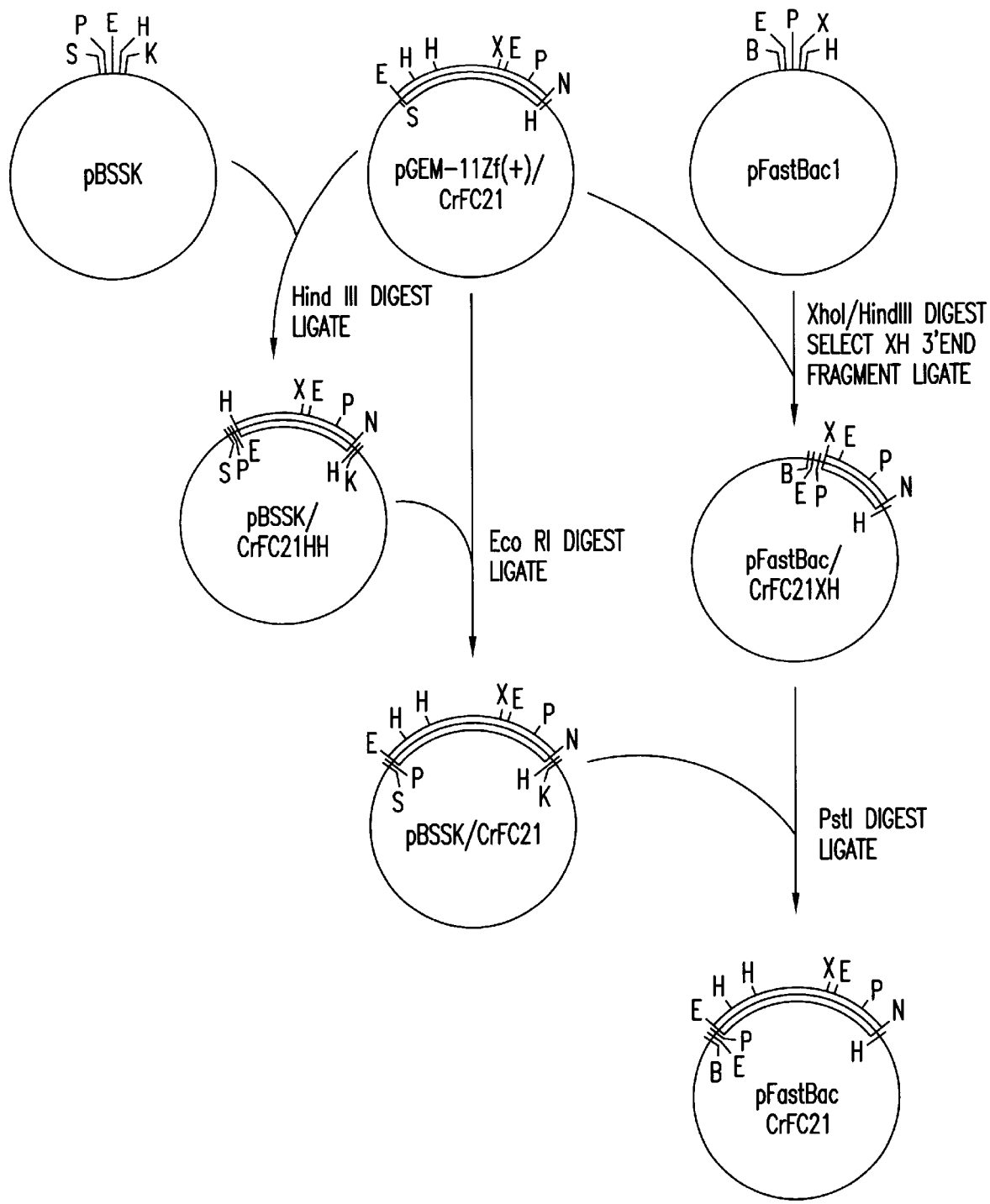
FIGS. 1A–B: Cloning of CrFC21 cDNA into the baculovirus expression vector, pFastBac I™ (SEQ ID NO:7). Two constructions of the same plasmid were done. (1A) A 2.3 kb Hind III fragment from pGEM11Zf(+)/CrFC21[15] was cloned into HindIII linearized pBluescript™ SK(+) (pBSSK) to give pBSSK/CrFC21/HH. This was then digested with Eco RI and ligated with the 2.3 kb Eco RI fragment from pGEM11Zf(+)/CrFC21 to regenerate recombinant pBSSK/CrFC21. Separately, a 1.3 kb Xho I/Hind III fragment, derived from pGEM11Zf(+)/CrFC21, was cloned into XhoI/HindIII digested pFastBac I™ to give pFastBac/CrFC21XH. The final full-length construct, pFastBac/CrFC21 was generated when the 2.9 kb Pst I CrFC fragment from pBSSK/CrFC21 was ligated to Pst I linearized pFastBac/CrFC21/XH.
Figure 1B:
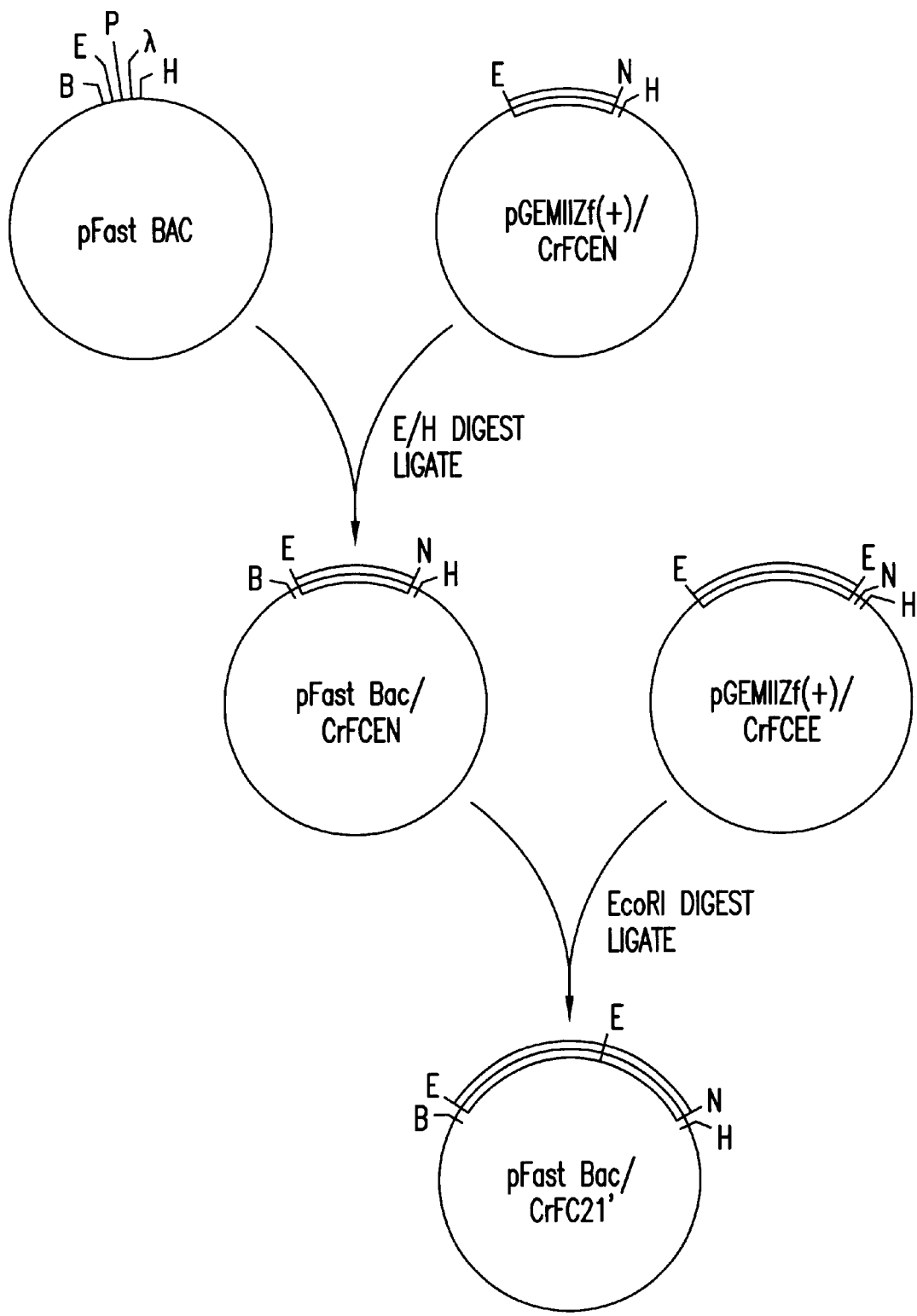

The strategy for cloning CrFC21 into the pFastBac I™ (Life Technologies, Inc.) expression shuttle vector is shown in FIG. 1. The recombinant plasmids were verified by restriction enzyme digestion. The 5' cloning sites were further confirmed by dideoxynucleotide sequencing using the forward primer designed from the −44 position of the polyhedrin promoter region, before they were used for transfection in insect cells. PCR and Southern analyses of the pFastBac/CrFC21 DNA confirmed the authenticity of recombinant baculoviruses.

The CrFC21 cDNA[10] from pGEM11Zf+/CrFC21[11] was recloned in two steps into pBluescript II SK+ (pBSSK), to yield pBSSK/CrFC 21. Further manipulations using pBBSK/CrFC21 and the baculoviral expression vector, pFastBac I™ were carried out using standard methods to clone full-length CrFC21, thus, yielding the recombinant construct, pFastBac/CrFC21 (FIG. 1). pFastBac/CrFC21 was transformed into competent E. coli, DH10Bac, and cultured in LB agar containing 50 μg/ml kanamycin, 7 μg/ml gentamycin, 10 μg/ml tetracycline, 30 μl of 2% X-gal and 40 μg/ml of IPTG. Screening[19] for positive clones involved the use of the 2.3 kb $^{32}$P-CrFC21/EE fragment as probe[10]. The recombinant bacmid DNA was isolated and transfected into Sf9 cells.

EXAMPLE 2

Expression of rFC in Insect Host Cells

Rapid Microtiter-plate Plaque Assay

Early log phase recombinant Sf9 cells were seeded at $6.5 \times 10^4$ cells per well. The culture was incubated in a sealed bag at 27° C. for 1 h. Meanwhile, the virus stock was serially diluted 10-fold with SFM containing 10% FBS to give final dilutions of $10^{-2}$ to $10^{-4}$. The BacPak™ Baculovirus Rapid Titer Kit (InVitrogen) was used for plaque assay. It is an immunoassay which uses a primary monoclonal antibody raised to an AcMNPV envelope glycoprotein (gp64). A secondary goat anti-mouse HRP-conjugated antibody enables visualization of the infected cells as blue-stained viral plaques or foci seen under the light microscope. The virus titer (pfu/ml) was calculated based on the following formula:

(Average no. of foci per well×dilution factor×40)×2 where 40 represents the inoculum volume normalization factor.

Scale-up of Infection of Sf9 Cells for Production of rFC

The culture supernatant from the 6-well plates was harvested and the viral stock was amplified by re-infection of Sf9 cells grown in 25 cm$^2$ flasks, using a multiplicity of infection (MOI) of 0.1–1.0. In such cultures, the viral stock reached a titer of $2 \times 10^7$ pfu/ml. Aliquots of this viral stock were re-inoculated at a MOI of 5–10 into Sf9 cells grown in 15 ml SFM medium in 75 cm$^2$ flasks. The volume of the viral inoculum was determined using the formula:

$$\frac{\text{(total no. of cells)} \times \text{(MOI in pfu/cell)}}{\text{(viral titer in pfu/ml)}}$$

Subsequently, Sf9 cells were passaged twice and conditioned to grow in suspension in 100 ml SFM medium, in spinner flasks (Bellco, USA). At the mid log phase of growth, the viral stock from the 75 cm$^2$ flask cells was inoculated at a MOI of 5–10. In the same manner, the cell culture volume was scaled up further in increasingly larger spinner flasks of 250, 500 and 1000 ml, infected with proportionally increasing volumes of viral stock at the same MOI.

Preparation of Protein Samples From Recombinant Baculovirus-infected Sf9 Cells.

(a) Cell lysate: Sf9 cells infected with the recombinant baculovirus at a MOI of 5–10 were harvested at 24, 48 and 72 h p.i. The cells were washed 3 times with pyrogen-free PBS and centrifuged at 3000×g for 10 min at 4° C. during each cycle of washing. The cell pellet was resuspended in 2–3 volumes of PBS and subjected to 5 cycles of freeze-thawing at −80° C. and 37° C., respectively. The cell debris was removed by centrifuging at 14000×g for 10 min at 4° C. The supernatant containing the soluble protein fraction was stored at −20° C. This supernatant represents the cell lysate.

(b) Culture supernatant: At the respective times of harvest, the cell medium was collected and centrifuged at 3000×g for 10 min at 4° C. to remove any cells or cell debris. The medium was then concentrated 10-fold by centrifugation through a BIOMAX™-50 kDa cutoff ultrafree membrane (Millipore) at 2000×g for 20 min or more. The total proteins present in the cell lysate and culture supernatant were quantified by Bradford assay[20]. Partial purification of rFC was carried out at 4° C. by gel filtration chromatography through SEPHADEX™ G-100 (e.g. 1.5×90 cm), using 0.05 M Tris-HCl (pH 7.5) containing 0.154 M NaCl. Fractions of 1 ml were collected and the void volume peak was concentrated. The protein concentration and Factor C enzyme activity were assayed for the resulting rFC. This preparation is henceforth referred to as "gel filtration-purified rFC".

Western Immunoblot Detection of rFC

Five μg of each cell lysate, or culture supernatant, harvested from 24, 48 and 72 h p.i. was analyzed on 10% SDS-PAGE gels, under denaturing conditions[21]. The electrophoretically-resolved bands were then transferred onto Immobilon™ PVDF membrane (Millipore, USA). The membrane was washed in PBS for 30 min, and blocked in 1% skimmed milk-PBS for 1 h followed by overnight incubation with rabbit anti-Factor C antibody diluted 1:500 in 0.2% Tween-20-PBS containing 1% BSA. Horseradish peroxidase-conjugated secondary goat anti-rabbit antibody, diluted 1:10000, was subsequently incubated with the membrane. For visualization of protein bands, the membrane was treated with SUPERSIGNAL™ chemiluminescent substrate (Pierce, USA) for 5–10 min, followed by 3 min exposure of the membrane to an X-ray film.

The Western analysis revealed 3 bands of immunoreactive rFC proteins of 132, 88 and 44 kDa, expressed by pFastBac/CrFC21 recombinant baculoviruses at 24, 48 and 72 h post infection, pi. At 24 h p.i., rFC was observed in the culture supernatant, but not in the cell lysate. The 48 h and 72 h p.i. culture supernatant showed increasing amounts. of rFC. The rFC in the cell lysate started to appear as a faint 132 kDa band only at 48 h p.i., and reached a substantial level at 72 h p.i. The immunoblot thus showed that the bulk of the rFC produced was released from the infected Sf9 cells into the medium. This is probably due to lysis of the infected cells, which released the recombinant protein. On ultracentrifugation at 100,000×g for 1 h at 4° C., rFC was found to be in the soluble fraction.

The results show that rFC protein was expressed correctly under the direction of the viral late promoter from the polyhedrin gene using the native translation start site from the CrFC cDNA. As there are six potential glycosylation sites in the CrFC cDNA sequence[10]; the protein band of 132 kDa represents the intact glycosylated form of Factor C. The 88 and 44 kDa proteins are likely the activated products of rFC whose molecular sizes correspond closely to the heavy and light chains, respectively, of double-chain Factor C[3]. Autoactivation could have occurred in the presence of picogram levels of ubiquitous endotoxin during the preparation of the protein sample for SDS-PAGE. In a comparison of rFC fromr 72 h p.i., electrophoresed under reducing and non-reducing conditions of SDS-PAGE, the 88 and 44 kDa bands became more prominent under reducing conditions. Under non-reducing conditions, LPS-activated rFC still retained its 132 kDa band, thus indicating the double-chain form of rFC[3]. The presence of a double chain form, of rFC was further proven when the BIOMAX™-purified rFC was pre-incubated with LPS before Western blotting. Under reducing condition, the LPS-treated rFC showed activated products of 88 and 44 kDa which were absent in the untreated rFC sample. However, under non-reducing conditions, the 132 kDa band was intact for both the LPS-treated and -untreated rFC.

EXAMPLE 3

RFC Binds Lipid A, the Biologically-potent Component of LPS

ELISA to Determine Lipid A Binding by rFC

In order to visualize and test the ability of rFC to specifically bind the biologically potent component of LPS, diphosphoryl lipid A (*E. coli* K12, D31M4, List Biologicals, Inc., USA) ranging from 0.01 to 100 ng in 100 µl volumes was immobilized onto 96-well Nunc IMMUNO-PLATES™ (PolySorp). The immobilization was carried out overnight at room temperature. Unbound lipid A was removed and the plates were washed 6 times with wash buffer containing 0.01% Tween 20 and 0.01% thimerosal in PBS. The excess sites were blocked for 1 h at room temperature with the same buffer containing 0.2% BSA, after which the wells were again washed 6 times. Aliquots of 100 µl of BIOMAX™ 50-treated rFC from culture supernatant containing 20 µg total protein was then added to the wells and incubated overnight at room temperature. Unbound rFC was removed, and the wells were washed 6 times in wash buffer. This was followed by addition of aliquots of 100 µl of 1:500 diluted rabbit anti-Factor C antibody and incubation was continued for 2 h at 37° C. Subsequently, the wells were washed 6 times in the wash buffer before addition of 100 µl aliquots of 1:2000 diluted goat anti-rabbit antibody conjugated with horseradish peroxidase. After washing the wells 6 times, 1 mg/ml of substrate ABTS, 2,2'-azino-di-[3-ethylbenzthiazoline sulfonate (6)] diammonium salt (Boehringer Mannheim) was added in 200 µl aliquots and incubated at room temperature for 15 min. The formation of a green product was quantified by reading its absorbance at 405 nm. rFC binding the immobilized lipid A results in positive color formation via the ELISA test.

The ELISA test for lipid A-binding indicates that, rFC is capable of specifically recognizing and binding to immobilized lipid A and hence, it could be used in the detection of endotoxin. With increasing amounts of lipid A in the wells, there is an increasing intensity of color development in the ABTS product (FIG. 2). Compared to the cell lysate, the 72 h p.i. culture supernatant consistently yielded more efficacious rFC for detection of lipid A (FIG. 3A). Furthermore, it was observed that blocking of excess sites in the wells with 0.2% BSA removed non-specific background binding and drastically improved the specificity of lipid A binding (FIG. 3B). This assay indicates that rFC can be used for mass screening of pharmaceutical products for LPS contamination, with the capability of quantifying LPS. This efficacy is comparable to the commercially available natural lysate derived from the Limulus or Tachypleus amoebocyte lysate.

EXAMPLE 4

Immobilized rFC Can be Used to Detect/remove LPS in a Sample

Two hundred µl samples containing either control wild-type supernatant (w/t Sf9, uninfected Sf9 cell supernatant) or partially-purified rFC samples (obtained by BIOMAX™-ultrafiltration), diluted in PBS to 10, 25 or 50 µg total protein per 200 µl were coated/immobilized onto each of the wells of a 96-well microtiter plate (NUNC, USA). The plates were left overnight at 4° C. Unbound protein was removed from the wells, and 200 µl of 0.2% BSA (depyrogenized by ultrafiltration) dissolved in PBS was added to the wells for 1 h at 37° C., to block unoccupied sites. The wells were washed 3 times with PBS. This was followed by addition of 200 µl FITC-conjugated LPS (*E. coli* O55:5B, List Biological Labs, USA) to the wells. The plate was incubated at 37° C. for 1 h, after which each well was washed 6×with PBS. The fluorescence was read at $EX_{495nm}$ and $Em_{525um}$ using LS-50B Spectrofluorimeter (Perkin Elmer).

Wells coated with 10, 25 or 50 µg of partially purified proteins containing rFC showed increasing efficiency of binding LPE-FITC. Blocking of the wells with 0.2% BSA reduced the background fluorescence reading, indicating improvement in the specificity of binding of LPS to the immobilized rFC. Immobilization of negative control proteins (w/tSf9: wild-type Sf9 cell culture supernatant of Sf9 cells infected with AcNMPV DNA alone, and rFCSN: yeast rFC derived from the truncated recombinant rFC devoid of LPS-binding domain described in ref. 16, to the wells did not capture or bind LPS, thus indicating the specificity of recognition of LPS by the immobilized rFC.

EXAMPLE 5

The Baculoviral rFC is Enzymatically Activated by LPS

Fluorimetric and Colorimetric Assays for LPS-activated rFC Enzyme Activity

As a proenzyme, Factor C becomes catalytically activated by trace levels of LPS. Thus, conversion of its enzymatic substrate to product indicates the presence of LPS. rFC samples present in the crude cell lysate and culture supernatant were used for analysis of LPS-activated Factor C enzyme activity by using two different substrates. The first, in a conventional tube assay format, is based on a modification of the fluorimetric assay of Iwanaga et al.[22] Using rFC obtained from a 72 h p.i. culture supernatant, 10 µg total protein in a volume of 0.1 ml was mixed with 1.9 ml of 50 mM Tris-HCl, pH 8.0, containing 0.1 M NaCl and 0.05 M $CaCl_2$. The mixtures were preincubated with 0.01 to 100 µg of LPS (*E. coli* O55:B5, Sigma) at 37° C. for 1 h before addition of 15 µl of 2 mM fluorimetric substrate, Boc-Val-Pro-Arg-MCA (Sigma). Incubation was continued for 30 min and the reaction was terminated with 0.1 ml glacial acetic acid. The product AMC was read in Fluorescence Units (FU) at $EX_{380nm}$ (slit 10 nm) and $Em_{460nm}$ (slit 5 nm) using a Perkin Elmer Luminescence Spectrophotometer (LS-50B). For multiple samples, this assay was routinely scaled down to 96-well microtiter plate assay. Briefly, the microassay involved 1 h pre-incubation of LPS with rFC in a volume of 100 µl, followed by addition of 1.5 µl of 2 mM fluorimetric substrate and 100 µl of 100 mM Tris-HCl, pH 8.0, containing 0.2 M NaCl and 0.05 M $CaCl_2$ and further incubation for 30 min at 37° C. before termination of the reaction with 10 µl of glacial acetic acid. The fluorescence was read in a 96-well microtiter plate reader module.

The second enzymatic assay for LPS involved a modification of the calorimetric test[23] where preincubation of culture supernatant proteins with LPS ranging from 0.01 to 10 pg was carried out at 37° C. for 1 h. The reaction volume was scaled down to 200 µl in 0.1 M Tris-HCl (pH 8.0) containing 5 mM $MgCl_2$. This was followed by addition of 50 μl of 2 mM of a calorimetric substrate, Boc-Val-Pro-Arg-p-nitroanilide (Seikagaku, Japan). Incubation at 37° C. was resumed for 1 h before termination of the reaction with 28 μl of glacial acetic acid. This substrate is hydrolyzed by rFC to produce pNA that was measured calorimetrically at $OD_{405nm}$.

From 24 to 48 to 72 h p.i., there was progressively increasing trend in the enzymatic activity of rFC in supernatants of cultures of insect cells transformed with the construct of Example 1, as indicated by the increase in fluorimetric units of the AMC product hydrolyzed from Boc-Val-Pro-Arg-MCA substrate. A comparison of the amount of total proteins present in the cell lysate (Lysate: 50 μg) and culture supernatant (Sup: 5 μg) illustrates that the culture supernatant from 72 h p.i. contained rFC that is >5–10 fold more effective in LPS detection. Twenty μg of BIOMAX™-purified rFC was able to detect 0.01 ng LPS. Using 40 to 80 μg of this protein, the detection limit could be easily extended to LPS levels below 0.01 pg or 0.001 ng/ml (FIG. 4). Purification of rFC by chromatography through SEPHADEX™ G-100 yielded enzymatic activity of even higher sensitivity to LPS (FIG. 5). It is envisaged that more elaborate purification of rFC following the methods covered in reference 24 would vastly improve the efficacy of the rFC for endotoxin detection. Furthermore, when the fluorimetric assay was modified to ~200 μl, using a 96-well microtiter plate, the sensitivity to LPS was improved by 10-fold (FIG. 6). This was directly attributable to the removal of background fluorescence by gel filtration.

Furthermore, the LPS-activated rFC enzyme assay was also conveniently quantifiable by a calorimetric assay with the Boc-Val-Pro-Arg-pNA substrate. The sensitivity to LPS was 0.1 pg (0.01 ng/ml) with 100 μg of BIOMAX™-50-treated culture supernatant when 2 mM of the pNA substrate was employed (FIG. 7). Similar to the fluorimetric assay, the calorimetric test also showed that the SEPHADEX™ G-100-purified rFC exhibited improved sensitivity to LPS, where 40 μg of purified rFC (instead of 100 μg of BIOMAX™ rFC) was sufficient to detect subpicogram levels of LPS (FIG. 8). Use of gel filtration-purified rFC resulted in a 4-fold increase in sensitivity to LPS. A direct comparison of the 2 microassays revealed that with gel filtration-purified rFC, the calorimetric assay achieved sensitivity to LPS comparable to the fluorimetric assay. Thus, using the scaled down, yet improved sensitivity assay for LPS detection, high throughput screening of samples can be conveniently achieved by either the calorimetric or fluorimetric assay using the 96-well microtiter plate assays. This enables rapid and mass screening of samples with limited volumes.

EXAMPLE 6

Fusion of Vtgss to LPS-binding Domain of CrFC Gene (CrFCES) for Expression and Secretion of Recombinant ES Protein From Drosophila Cells The O. aureus vitellogenin gene secretory signal (Vtgss) was fused upstream to the EcoRI-SalI cDNA fragment encoding the LPS-binding domain of Carcinoscorpius rotundicauda Factor C CrFCES (10). The construct was inserted into the pAc5/V5-His vector backbone (InVitrogen, see FIG. 13).

Vitellogenin is the yolk protein of the oviparous and ovoviviparous animals. It is exclusively synthesized in the liver, secreted and finally deposited in the eggs. The secretion of vitellogenin is directed by its secretory signal. The expression of the LPS-binding domain of Factor C (~333 amino acids) is challenging because it is rich in cysteine residues and requires the correct formation of 9 disulfide bonds for full biological activity. The recombinant protein (VtgssCrFCES) is synthesized using the Drosophila Expression System™ Stable recombinant Drosophila cell lines were obtained and the distribution of the protein was identified by Western-blotting using very sensitive chemiluminescent detection. The recombinant protein was also purified to homogeneity for N-terminal amino acid sequencing.

Precise cleavage between Vtgss and the adjoining mature fusion CrFCES protein was demonstrated by N-terminal amino acid sequencing of VtgCrFCES. The data show that Vtgss is cleaved at a single point (FIG. 14A). The absence of multiple cleavages suggests that Vtgss directs homogenous production of secreted heterologous protein from Drosophila cells.

Results of the Western Blot show that practically all of VtgCrFCES is secreted into the culture medium (FIGS. 15A, 15B). No intracellular VtgCrFCES was detected using the very sensitive Chemiluminescent Western Blot. The fusion of Vtgss to the LPS-binding domain resulted in its secretion whereas the native signal of Factor C targets it intracellularly. The presence of VtgCrFCES in the culture medium allows simple purification from either batch or continuous culture.

The LPS-binding properties of the secreted protein are retained as shown by plasmon resonance studies, using the BIACORE™ in vivo biosensor apparatus (FIG. 16). The protein secreted from the Drosophila cells binds LPS despite addition of 6 Vtgss-derived amino acids to the N-terminus of the CrFcES protein. Thus, Drosophila cells can be used to express and secrete correctly folded CrFCES. Functional Vtgss truncated after the aspartic acid residue that is the carboxy-terminus of the cleavage site can be used to reduce the number of extra amino terminal residues.

EXAMPLE 7

Evaluation of Microfluorimetric Detection of LPS in Aqueous Solution and Human Plasma by rFC and LAL The microfluorimetric assay for LPS-activated Factor C of Example 5 produces a 10-fold improvement in the sensitivity of detection of LPS. In the present example, the same assay was employed for LPS detection in human plasma by conventional Limulus amoebocyte lysate (LAL), and the efficacy was compared with that of rFC. Briefly, LPS was pre-incubated with LAL or rFC in a volume of 100 $\mu$l, followed by addition of 1.5 $\mu$l of 2 mM fluorimetric substrate (Boc-Val-Pro-Arg-MCA, Sigma) and 100 $\mu$l of 10,0 mM Tris-HCl, pH 8.0, containing 0.2 M NaCl and 0.05 M $CaCl_2$, then further incubated for 30 min at 37° C. before termination of the reaction with 10 $\mu$l of glacial acetic acid. The fluorescence of the released product, AMC, was read in a 96-well microtiter plate reader module using a Perkin Elmer Lumiscence Spectrophotometer (LS-50B) at $EX_{380nm}$ and $Em_{460nm}$.

The results, presented in FIGS. 17–20 and Table 1 show that the new improved protocol for microfluorimetric assay of LPS using rFC or LAL can be used as a sensitive method of detection of LPS in, for example, aqueous solutions and human plasma.

FIG. 17 shows a plot of the fluorescence units (FU) of the product of the Factor C enzymatic reaction after 10 $\mu$g of LAL or rFC was pre-activated by increasing amounts of LPS. The microfluorimetric detection of a range of concentrations of LPS by LAL in comparison to rFC from different production batches (Nos. 1, 2, 3 and 4) is shown.

FIGS. 18A and 18B show a comparison between (i) effective of EDTA-containing plasma (E) over citrated plasma (C) in LPS detection by (ii) rFC and by conventional LAL. In these tests, plasma derived from cord blood was spiked with LPS, and the resulting LPS-spiked plasma samples were, used in the microfluorimetric assay employing Factor C from either rFC or LAL. The results show that first, citrate is a recommended anticoagulant to use for deriving plasma for the purpose of LPS-detection by either rFC or LAL. Second, there is consistency in the level of sensitivity of LPS-detection by rFC and LAL.

FIGS. 19A and 19B show a comparison between detection of LPS by 10 μg of rFC (15A) and 10 μg of LAL (15B) using 2-day old plasma samples derived by citrate treatment. There is close visual correlation observed between samples measured using rFC and LAL.

FIGS. 20A and 20B show another comparison between detection of LPS by 10 μg of rFC (16A) and 10 μg of LAL (16B) using 7-day old plasma samples derived by citrate treatment. Again, close correlation can be seen between LPS detection in samples using rFC and LAL.

Table 1 shows examples of the use of the microfluorimetric assay for LPS detection by LAL over a one year period. Aging of LAL preparation shows a progressive increase in the blank (0 EU/ml LPS) values of FU, suggesting slight autoactivation of the LAL over time. There is a corresponding increase in most cases in the FU at 0.125 EU/ml LPS. With the exception of the November 13 case, there was a 33% loss of sensitivity of LPS-induced increase in FU over time.

TABLE 1

CASE EXAMPLES WHERE NEW MICROFLUORIMETRIC ASSAY WAS APPLIED TO LAL SAMPLES

| Date | LAL (amount in μg) | LPS (0 EU/ml) | LPS (0.125 EU/ml) | Fold |
|---|---|---|---|---|
| Jan. 14, 1998 | 10 | 16.3 | 208.0 | 12.8 |
| Feb. 25, 1998 | 10 | 16.1 | 299.8 | 18.6 |
| Aug. 3, 1998 | 10 | 54.9 | 562.7 | 10.2 |
| Nov. 13, 1998 | 10 | 73.1 | 261.8 | 3.6 |
| Nov. 18, 1998 | 10 | 84.2 | 748.9 | 8.9 |
| Dec. 22, 1998 | 10 | 69.7 | 591.4 | 8.5 |

The invention being thus described, modification of the invention with respect to various materials and methods will be apparent to one of ordinary skill in the art. Such modifications are to be considered as falling within the scope of the invention, which is defined by the claims hereinbelow.

References

Articles of the scientific and patent literature referred to herein are incorporated by reference in their entirety by citation thereto.

1. Muta, T., Miyata, T., Misumi, Y., Tokunagja, F., Nakamura, J., Toh, Y., Jkehara, Y., and Iwanaga, S. 1991. *J. Biol. Chem.* 266: 6554–6561.
2. Navas, M. M. A, Ding, J. L., and Ho, B. 1990. Inactivation of Factor C by dimethyl suiphoxide inhibits coagulation of the Carcinoscorpius amoebocyte lysate. *Biochem Mol Biol Int* 21:805–813.
3. Ding, J. L., Navas, M. M. A., and Ho, B. 1993. Two forms of Factor C from the amoebocytes of *Carcinoscorpius rotundicauda*: purification and characterization. *Biochim Biophys Acta* 1202:149–156.
4. Ho, B., Kim, J. C., and Ding, J. L. 1993. Electrophoretic analysis of endotoxin-activated gelation reaction of Carcinoscorpius rotundicauda amoebocyte lysate. *Biochem Mol Biol Int* 29:687–694.
5. Iwanaga, S. 1993. The limulus clotting reaction. *Current Opinion in Immunol* 5:74–82.
6. Ho, B. 1983. An improved Limulus gelation assay. *Microbios Lett* 24:81–84.
7. Cooper, J. F. 1975. Principles and applications of the limulus test for pyrogen in parenteral drugs. *Bull. Parent. Drug Ass.* 29: 122.
8: Novitsky, T. J. 1991. Discovery to commercialization: the blood of the horseshoe crab. *Oceanus* 27: 13–18.
9. Sekiguchi, K. and Nakamura, K. 1979. Ecology of the extant horseshoe crabs. In: Biomedical Applications of the Horseshoe Crabs (Limulidae), Eds., Cohen et al., Allan R. Liss, New York, pp. 37–49.
10. Ding, J. L., Navas III, M. A. A., and Ho, B. 1995. Molecular cloning and sequence analysis of Factor C cDNA from the Singapore horseshoe crab, *Carcinoscorpius rotundicauda*. *Mol Marine Biol Biotechnol* 4:90–103.
11. Roopashree, S. D., Chai, C., Ho, B, and Ding, J. L. 1995. Expression of *Carcinoscorpius rotundicauda* Factor C cDNA. *Biochem Mol Biol Intl* 4:841–849.
12. Roopashree, S. D., Ho, B, and Ding, J. L. 1996. Expression of *Carcinoscorpius rotundicauda* Factor C in Pichia pastoris. *Mol Marine Biol Biotechnol* 5: 334–343.
13. Ding, J. L., Chai, C., Pui, A. W. M. and Ho, B. 1997. Expression of full length and deletion homologues of *Carcinoscorpius rotundicauda* Factor C in *Saccharomyces cerevisiae*: immunoreactivity and endotoxin binding. *J Endotoxin Res*. 4(1): 33–43.
14 Pui, A. W. M., Ho, B. and Ding, J. L. 1998. Yeast recombinant Factor C from horseshoe crab binds endotoxin and causes bacteriostasis. *J. Endotoxin Res.* 4(6): 391–400.
15. U.S. Pat. No. 5,716,834.
16. Copending U.S. patent application Ser. No. 08/596,405.
17. Sambrook et al., Molecular Cloning: A Laboratory Manual, $2^{nd}$ ed., c. 1989 by Cold Spring Harbor Laboratory, Cold Spring Harbor, N.Y.
18. ibid. pp. 9. 50–9. 51.
19. Grunstein, M., and Hogness, D. S. 1975. Colony hybridization: A method for the isolation of cloned DNAs that contain a specific gene. *Proc Natl Acad Sci* 72:3961.
20. Bradford, M. M. 1976. A rapid and sensitive method for the quantitation of microgram quantities of protein utilizing the principle of protein dye binding. *Anal Biochem* 72:248–254.
21. Laemmli, U. K. 1970. Cleavage of structural proteins during the assembly of the head of bacteriophage T4. *Nature* 227:680–685.
22. Iwanaga, S., Morita, T., Ohki, M. 1980. Endotoxin-sensitive substance. Japan Patent Agency Official Bulletin; S57–108018.
23. Nakamura, T., Morita, T., and Iwanaga, S. 1986 Lipopolysaccharide-sensitive serine protease zymogen (Factor C) found in Limulus hemocytes: Isolation and characterization. *Eur J Biochem* 154: 511–521.
24. U.S. Pat. No. 5,712,144.
25. Novitsky, *J. Endotoxin Research*, Vol. 1, pp. 253–263 (1994)

What is claimed is:

1. An assay for endotoxin, said assay comprising:

a) contacting a sample to be assayed, wherein said sample comprises a peptide cleavable to produce a chromogenic or fluorogenic moiety, with a recombinant Factor C of a horseshoe crab, wherein said recombinant Factor C is obtained from an insect host cell culture and has protease activity; and b) measuring the amount of said chromogenic or fluorogenic moiety cleaved from said peptide, wherein cleavage of said moiety from said peptide is indicative of the presence of said endotoxin in said sample.

2. The assay of claim 1, wherein said peptide is N-t-Boc-Val-Pro-Arg-MCA, Mu-Val-Pro-Arg-AFC, or Boc-Val-Pro-Arg-pNA and wherein said assay is conducted in a volume of about 200 μl.

3. The assay of claim 2, wherein said insect host cell is a lepidopteran cell.

4. The assay of claim 2, wherein said recombinant Factor C is obtained from a dipteran host cell culture.

5. The assay of claim 2, wherein said recombinant Factor C comprises a polypeptide having 75% or greater sequence identity to an amino acid sequence selected from the group consisting of SEQ ID NO:2, SEQ ID NO:4, and the amino acid sequence of Factor C of *Tachypleus tndentatus*.

6. The assay of claim 1, wherein said insect host cell is a lepidopteran cell.

7. The assay of claim 1, wherein said recombinant Factor C is obtained from a dipteran host cell culture.

8. The assay of claim 1, wherein said recombinant Factor C comprises a polypeptide having 75% or greater sequence identity to an amino acid sequence selected from the group consisting of SEQ ID NO:2, SEQ ID NO:4, and the amino acid sequence of Factor C of *Tachypleus tndentatus*.

9. The assay of claim 1, wherein said peptide is N-t-Boc-Val-Pro-Arg-MCA or Mu-Val-Pro-Arg-AFC.

10. The assay of claim of claim 1, wherein said recombinant Factor C is obtained from a Sf9 host cell culture.

11. An assay for endotoxin, said assay comprising:
  a) contacting a sample to be assayed, said sample having a volume of about 200 µl and comprising a peptide cleavable to produce a chromogenic or fluorogenic moiety, with a recombinant Factor C of a horseshoe crab, wherein said recombinant Factor C is produced using a vector comprising a cDNA encoding Factor C, is obtained from an insect host cell culture, and has protease activity; and
  b) measuring the amount of said chromogenic or fluorogenic moiety cleaved from said peptide, wherein cleavage of said moiety from said peptide is indicative of the presence of said endotoxin in said sample.

12. The assay of claim 11, wherein said cDNA encoding Factor C comprises a nucleic acid encoding a polypeptide having 75% or greater sequence identity to an amino acid sequence selected from the group consisting of SEQ ID NO:2, SEQ ID NO:4, and the amino acid sequence of Factor C of *Tachypleus tridentatus*.

13. The assay of claim 12, wherein said nucleic acid is a cDNA encoding Factor C of Limulus.

14. The assay of claim 13, wherein said recombinant Factor C is obtained using a baculovirus-derived host-vector system.

15. The assay of claim 12, wherein said nucleic acid encodes the amino acid sequence of SEQ ID NO:2, SEQ ID NO:4, or the amino acid sequence of *Tachypleus tridentatus*.

16. The assay of claim 15, wherein said recombinant Factor C is obtained using a baculovirus-derived host-vector system.

17. The assay of claim 12, wherein said recombinant Factor C is obtained using a baculovirus-derived host-vector system.

18. The assay of claim 11, wherein said recombinant Factor C is obtained using a baculovirus-derived host-vector system.

19. The assay of claim 11, wherein said insect cell is a dipteran cell.

20. The assay of claim of claim 1, wherein said recombinant Factor C is obtained from a lepidopteran host cell culture.

21. An assay for endotoxin, said assay compnsing:
  a) mixing a sample to be assayed with a recombinant Factor C of a horseshoe crab, wherein said recombinant Factor C is obtained from an insect host cell culture and has protease activity, and incubating the mixed sample;
  b) adding to the incubated, mixed sample a peptid that is cleavable to produce a chromogenic or fluorogenic moiety and continuing incubation to allow cleavage of the peptide by Factor C activated by endotoxin in said sample; and
  c) measuring the amount of said chromogenic or fluorogenic moiety cleaved from said peptide, wherein cleavage of said moiety from said peptide is indicative of the presence of said endotoxin in said sample.

22. The assay of claim 21, performed in a volume of about 200 µl.

23. The assay of claim 21, wherein the incubation at step a) is performed for at least 1 hour and wherein the incubation at step b) is performed for at least one-half hour.

24. The assay of claim 21, wherein said recombinant Factor C is produced using a baculovirus based host vector system.

25. The assay of claim of claim 21, wherein said recombinant Factor C is obtained from a lepidopteran host cell culture.

* * * * *

SEQUENCE LISTING

<160> NUMBER OF SEQ ID NOS: 7

<210> SEQ ID NO 1
<211> LENGTH: 4182
<212> TYPE: DNA
<213> ORGANISM: Carcinoscorpius rotundicauda
<220> FEATURE:
<221> NAME/KEY: CDS
<222> LOCATION: (569)..(3817)
<220> FEATURE:
<223> OTHER INFORMATION: any n or Xaa = Unknown

<400> SEQUENCE: 1

```
gtatttaatg tctcaacggt aaaggtttca ttgtagctaa tatttaactt cctccctgtg    60
ccccaaatcg cgagtatgac gtcagttaag acttcgtatt ttaagagtta aacacgagcc   120
ttaaagagcg atattttttt tgttaaacac ttccaactta atacaattgg caaactttca   180 aaataaagt ggaaaaggag gtaaaaaaga tgaaaaaaat tcgcatacaa tagaatacaa    240
taaaatgtgt tgtctttact gtcaacactt actgttcgtt cggtcacagc tgtgaatcgg   300
ggtgacttta tgtttgtagt ggtcttaaaa acgggtactt ggttgttttg aaaattttaa   360
aacctacata tgattctcct aaatttttgt ttataaatta gcaccatttg cgacctaaat   420
cttttttgta gtcttaagtt tagttgacat aaaaacaaaa tttgtaacaa cacacggtat   480
aaactaaata gcttcagatg ggtcgtatga caaggaaact tttaaataat tatgaaagtt   540
tttttaaaat ttgactaagg tttagatt atg tgg gtg aca tgc ttc gac acg      592
                                 Met Trp Val Thr Cys Phe Asp Thr
                                  1               5 ttt ctt ttt gtt tgt gaa agt tca gtt ttc tgt ttg ttg tgt gtg tgg    640
Phe Leu Phe Val Cys Glu Ser Ser Val Phe Cys Leu Leu Cys Val Trp
 10              15                  20 agg ttt ggt ttc tgt agg tgg cgt gtt ttc tac agt ttt cca ttc gtt    688
Arg Phe Gly Phe Cys Arg Trp Arg Val Phe Tyr Ser Phe Pro Phe Val
 25              30                  35                  40 aag tca aca gtt gtt tta tta cag tgt tac cat tac tct ctc cac aat    736
Lys Ser Thr Val Val Leu Leu Gln Cys Tyr His Tyr Ser Leu His Asn
             45                  50                  55 acc tca aag ttc tac tct gtg aat cct gac aag cca gag tac att ctt    784
Thr Ser Lys Phe Tyr Ser Val Asn Pro Asp Lys Pro Glu Tyr Ile Leu
         60                  65                  70 tca ggt tta gtt cta ggg cta cta gcc caa aaa atg cgc cca gtt cag    832
Ser Gly Leu Val Leu Gly Leu Leu Ala Gln Lys Met Arg Pro Val Gln
     75                  80                  85 tcc aaa gga gta gat cta ggc ttg tgt gat gaa acg agg ttc gag tgt    880
Ser Lys Gly Val Asp Leu Gly Leu Cys Asp Glu Thr Arg Phe Glu Cys
 90                  95                 100 aag tgt ggc gat cca ggc tat gtg ttc aac att cca gtg aaa caa tgt    928
Lys Cys Gly Asp Pro Gly Tyr Val Phe Asn Ile Pro Val Lys Gln Cys
105                 110                 115                 120 aca tac ttt tat cga tgg agg ccg tat tgt aaa cca tgt gat gac ctg    976
Thr Tyr Phe Tyr Arg Trp Arg Pro Tyr Cys Lys Pro Cys Asp Asp Leu
                125                 130                 135 gag gct aag gat att tgt cca aag tac aaa cga tgt caa gag tgt aag   1024
Glu Ala Lys Asp Ile Cys Pro Lys Tyr Lys Arg Cys Gln Glu Cys Lys
            140                 145                 150 gct ggt ctt gat agt tgt gtt act tgt cca cct aac aaa tat ggt act   1072
Ala Gly Leu Asp Ser Cys Val Thr Cys Pro Pro Asn Lys Tyr Gly Thr
        155                 160                 165
```

```
tgg tgt agc ggt gaa tgt cag tgt aag aat gga ggt atc tgt gac cag    1120
Trp Cys Ser Gly Glu Cys Gln Cys Lys Asn Gly Gly Ile Cys Asp Gln
170                 175                 180 agg aca gga gct tgt gca tgt cgt gac aga tat gaa ggg gtg cac tgt    1168
Arg Thr Gly Ala Cys Ala Cys Arg Asp Arg Tyr Glu Gly Val His Cys
185                 190                 195                 200 gaa att ctc aaa ggt tgt cct ctt ctt cca tcg gat tct cag gtt cag    1216
Glu Ile Leu Lys Gly Cys Pro Leu Leu Pro Ser Asp Ser Gln Val Gln
        205                 210                 215 gaa gtc aga aat cca cca gat aat ccc caa act att gac tac agc tgt    1264
Glu Val Arg Asn Pro Pro Asp Asn Pro Gln Thr Ile Asp Tyr Ser Cys
    220                 225                 230 tca cca ggg ttc aag ctt aag ggt atg gca cga att agc tgt ctc cca    1312
Ser Pro Gly Phe Lys Leu Lys Gly Met Ala Arg Ile Ser Cys Leu Pro
235                 240                 245 aat gga cag tgg agt aac ttt cca ccc aaa tgt att cga gaa tgt gcc    1360
Asn Gly Gln Trp Ser Asn Phe Pro Pro Lys Cys Ile Arg Glu Cys Ala
        250                 255                 260 atg gtt tca tct cca gaa cat ggg aaa gtg aat gct ctt agt ggt gat    1408
Met Val Ser Ser Pro Glu His Gly Lys Val Asn Ala Leu Ser Gly Asp
265                 270                 275                 280 atg ata gaa ggg gct act tta cgg ttc tca tgt gat agt ccc tac tac    1456
Met Ile Glu Gly Ala Thr Leu Arg Phe Ser Cys Asp Ser Pro Tyr Tyr
            285                 290                 295 ttg att ggt caa gaa aca tta acc tgt cag ggt aat ggt cag tgg aat    1504
Leu Ile Gly Gln Glu Thr Leu Thr Cys Gln Gly Asn Gly Gln Trp Asn
                300                 305                 310 gga cag ata cca caa tgt aag aac tta gtc ttc tgt cct gac ctg gat    1552
Gly Gln Ile Pro Gln Cys Lys Asn Leu Val Phe Cys Pro Asp Leu Asp
            315                 320                 325 cct gta aac cat gct gaa cac aag gtt aaa att ggt gtg gaa caa aaa    1600
Pro Val Asn His Ala Glu His Lys Val Lys Ile Gly Val Glu Gln Lys
330                 335                 340 tat ggt cag ttt cct caa ggc act gaa gtg acc tat acg tgt tcg ggt    1648
Tyr Gly Gln Phe Pro Gln Gly Thr Glu Val Thr Tyr Thr Cys Ser Gly
345                 350                 355                 360 aac tac ttc ttg atg ggt ttt gac acc tta aaa tgt aac cct gat ggg    1696
Asn Tyr Phe Leu Met Gly Phe Asp Thr Leu Lys Cys Asn Pro Asp Gly
            365                 370                 375 tct tgg tca gga tca cag cca tcc tgt gtt aaa gtg gca gac aga gag    1744
Ser Trp Ser Gly Ser Gln Pro Ser Cys Val Lys Val Ala Asp Arg Glu
        380                 385                 390 gtc gac tgt gac agt aaa gct gta gac ttc ttg gat gat gtt ggt gaa    1792
Val Asp Cys Asp Ser Lys Ala Val Asp Phe Leu Asp Asp Val Gly Glu
    395                 400                 405 cct gtc agg atc cac tgt cct gct ggc tgt tct ttg aca gct ggt act    1840
Pro Val Arg Ile His Cys Pro Ala Gly Cys Ser Leu Thr Ala Gly Thr
410                 415                 420 gtg tgg ggt aca gcc ata tac cat gaa ctt tcc tca gtg tgt cgt gca    1888
Val Trp Gly Thr Ala Ile Tyr His Glu Leu Ser Ser Val Cys Arg Ala
425                 430                 435                 440 gcc atc cat gct ggc aag ctt cca aac tct gga gga gcg gtg cat gtt    1936
Ala Ile His Ala Gly Lys Leu Pro Asn Ser Gly Gly Ala Val His Val
            445                 450                 455 gtg aac aat ggc ccc tac tcg gac ttt ctg ggt agt gac ctg aat ggg    1984
Val Asn Asn Gly Pro Tyr Ser Asp Phe Leu Gly Ser Asp Leu Asn Gly
        460                 465                 470 ata aaa tcc gaa gag ttg aag tct ctt gcc cgg agt ttc cga ttc gat    2032
Ile Lys Ser Glu Glu Leu Lys Ser Leu Ala Arg Ser Phe Arg Phe Asp
    475                 480                 485
```

```
                                                                -continued tat gtc agt tcc tcc aca gca ggt aaa tca gga tgt cct gat gga tgg       2080
Tyr Val Ser Ser Ser Thr Ala Gly Lys Ser Gly Cys Pro Asp Gly Trp
    490                 495                 500 ttt gag gta gac gag aac tgt gtg tac gtt aca tca aaa cag aga gcc       2128
Phe Glu Val Asp Glu Asn Cys Val Tyr Val Thr Ser Lys Gln Arg Ala
505                 510                 515                 520 tgg gaa aga gct caa ggt gtg tgt acc aat atg gct gct cgt ctt gct       2176
Trp Glu Arg Ala Gln Gly Val Cys Thr Asn Met Ala Ala Arg Leu Ala
                525                 530                 535 gtg ctg gac aaa gat gta att cca aat tca ttg act gag act cta cga       2224
Val Leu Asp Lys Asp Val Ile Pro Asn Ser Leu Thr Glu Thr Leu Arg
            540                 545                 550 ggg aaa ggg tta aca acc acg tgg ata gga ttg cac aga cta gat gca       2272
Gly Lys Gly Leu Thr Thr Thr Trp Ile Gly Leu His Arg Leu Asp Ala
        555                 560                 565 gag aag ccc ttt att tgg gag tta atg gat cgt agt aat gtg gtt ctg       2320
Glu Lys Pro Phe Ile Trp Glu Leu Met Asp Arg Ser Asn Val Val Leu
    570                 575                 580 aat gat aac cta aca ttc tgg gcc tct ggc gaa cct gga aat gaa act       2368
Asn Asp Asn Leu Thr Phe Trp Ala Ser Gly Glu Pro Gly Asn Glu Thr
585                 590                 595                 600 aac tgt gta tat atg gac atc caa gat cag ttg cag tct gtg tgg aaa       2416
Asn Cys Val Tyr Met Asp Ile Gln Asp Gln Leu Gln Ser Val Trp Lys
                605                 610                 615 acc aag tca tgt ttt cag ccc tca agt ttt gct tgc atg atg gat ctg       2464
Thr Lys Ser Cys Phe Gln Pro Ser Ser Phe Ala Cys Met Met Asp Leu
            620                 625                 630 tca gac aga aat aaa gcc aaa tgc gat gat cct gga tca ctg gaa aat       2512
Ser Asp Arg Asn Lys Ala Lys Cys Asp Asp Pro Gly Ser Leu Glu Asn
        635                 640                 645 gga cac gcc aca ctt cat gga caa agt att gat ggg ttc tat gct ggt       2560
Gly His Ala Thr Leu His Gly Gln Ser Ile Asp Gly Phe Tyr Ala Gly
    650                 655                 660 tct tct ata agg tac agc tgt gag gtt ctc cac tac ctc agt gga act       2608
Ser Ser Ile Arg Tyr Ser Cys Glu Val Leu His Tyr Leu Ser Gly Thr
665                 670                 675                 680 gaa acc gta act tgt aca aca aat ggc aca tgg agt gct cct aaa cct       2656
Glu Thr Val Thr Cys Thr Thr Asn Gly Thr Trp Ser Ala Pro Lys Pro
                685                 690                 695 cga tgt atc aaa gtc atc acc tgc caa aac ccc cct gta cca tca tat       2704
Arg Cys Ile Lys Val Ile Thr Cys Gln Asn Pro Pro Val Pro Ser Tyr
            700                 705                 710 ggt tct gtg gaa atc aaa ccc cca agt cgg aca aac tcg ata agt cgt       2752
Gly Ser Val Glu Ile Lys Pro Pro Ser Arg Thr Asn Ser Ile Ser Arg
        715                 720                 725 gtt ggg tca cct ttc ttg agg ttg cca cgg tta ccc ctc cca tta gcc       2800
Val Gly Ser Pro Phe Leu Arg Leu Pro Arg Leu Pro Leu Pro Leu Ala
    730                 735                 740 aga gca gcc aaa cct cct cca aaa cct aga tcc tca caa ccc tct act       2848
Arg Ala Ala Lys Pro Pro Pro Lys Pro Arg Ser Ser Gln Pro Ser Thr
745                 750                 755                 760 gtg gac ttg gct tct aaa gtt aaa cta cct gaa ggt cat tac cgg gta       2896
Val Asp Leu Ala Ser Lys Val Lys Leu Pro Glu Gly His Tyr Arg Val
                765                 770                 775 ggg tct cga gcc att tac acg tgc gag tcg aga tac tac gaa cta ctt       2944
Gly Ser Arg Ala Ile Tyr Thr Cys Glu Ser Arg Tyr Tyr Glu Leu Leu
            780                 785                 790 gga tct caa ggc aga aga tgt gac tct aat gga aac tgg agt ggt cgg       2992
Gly Ser Gln Gly Arg Arg Cys Asp Ser Asn Gly Asn Trp Ser Gly Arg
```

-continued

|   | 795 |   |   |   | 800 |   |   |   | 805 |   |   |   |   |
|---|---|---|---|---|---|---|---|---|---|---|---|---|---|
| cca | gcg | agc | tgt | att | cca | gtt | tgt | gga | cgg | tca | gac | tct | cct | cgt | tct | 3040 |
| Pro | Ala | Ser | Cys | Ile | Pro | Val | Cys | Gly | Arg | Ser | Asp | Ser | Pro | Arg | Ser |   |
|   | 810 |   |   |   | 815 |   |   |   | 820 |   |   |   |   |

| cct | ttt | atc | tgg | aat | ggg | aat | tct | aca | gaa | ata | ggt | cag | tgg | ccg | tgg | 3088 |
| Pro | Phe | Ile | Trp | Asn | Gly | Asn | Ser | Thr | Glu | Ile | Gly | Gln | Trp | Pro | Trp |   |
| 825 |   |   |   |   | 830 |   |   |   | 835 |   |   |   | 840 |

| cag | gca | gga | atc | tct | aga | tgg | ctt | gca | gac | cac | aat | atg | tgg | ttt | ctc | 3136 |
| Gln | Ala | Gly | Ile | Ser | Arg | Trp | Leu | Ala | Asp | His | Asn | Met | Trp | Phe | Leu |   |
|   |   |   |   | 845 |   |   |   |   | 850 |   |   |   |   | 855 |

| cag | tgt | gga | gga | tct | cta | ttg | aat | gag | aaa | tgg | atc | gtc | act | gct | gcc | 3184 |
| Gln | Cys | Gly | Gly | Ser | Leu | Leu | Asn | Glu | Lys | Trp | Ile | Val | Thr | Ala | Ala |   |
|   |   |   |   |   | 860 |   |   |   | 865 |   |   |   | 870 |

| cac | tgt | gtc | acc | tac | tct | gct | act | gct | gag | att | att | gac | ccc | aat | cag | 3232 |
| His | Cys | Val | Thr | Tyr | Ser | Ala | Thr | Ala | Glu | Ile | Ile | Asp | Pro | Asn | Gln |   |
|   |   |   | 875 |   |   |   | 880 |   |   |   | 885 |

| ttt | aaa | atg | tat | ctg | ggc | aag | tac | tac | cgt | gat | gac | agt | aga | gac | gat | 3280 |
| Phe | Lys | Met | Tyr | Leu | Gly | Lys | Tyr | Tyr | Arg | Asp | Asp | Ser | Arg | Asp | Asp |   |
|   | 890 |   |   |   | 895 |   |   |   | 900 |

| gac | tat | gta | caa | gta | aga | gag | gct | ctt | gag | atc | cac | gtg | aat | cct | aac | 3328 |
| Asp | Tyr | Val | Gln | Val | Arg | Glu | Ala | Leu | Glu | Ile | His | Val | Asn | Pro | Asn |   |
| 905 |   |   |   | 910 |   |   |   | 915 |   |   |   | 920 |

| tac | gac | ccc | ggc | aat | ctc | aac | ttt | gac | ata | gcc | cta | att | caa | ctg | aaa | 3376 |
| Tyr | Asp | Pro | Gly | Asn | Leu | Asn | Phe | Asp | Ile | Ala | Leu | Ile | Gln | Leu | Lys |   |
|   |   |   |   | 925 |   |   |   |   | 930 |   |   |   |   | 935 |

| act | cct | gtt | act | ttg | aca | aca | cga | gtc | caa | cca | atc | tgt | ctg | cct | act | 3424 |
| Thr | Pro | Val | Thr | Leu | Thr | Thr | Arg | Val | Gln | Pro | Ile | Cys | Leu | Pro | Thr |   |
|   |   |   | 940 |   |   |   | 945 |   |   |   | 950 |

| gac | atc | aca | aca | aga | gaa | cac | ttg | aag | gag | gga | aca | tta | gca | gtg | gtg | 3472 |
| Asp | Ile | Thr | Thr | Arg | Glu | His | Leu | Lys | Glu | Gly | Thr | Leu | Ala | Val | Val |   |
|   |   | 955 |   |   |   | 960 |   |   |   | 965 |

| aca | ggt | tgg | ggt | ttg | aat | gaa | aac | aac | acc | tat | tca | gag | acg | att | caa | 3520 |
| Thr | Gly | Trp | Gly | Leu | Asn | Glu | Asn | Asn | Thr | Tyr | Ser | Glu | Thr | Ile | Gln |   |
|   | 970 |   |   |   | 975 |   |   |   | 980 |

| caa | gct | gtg | cta | cct | gtt | gtt | gca | gcc | agc | acc | tgt | gaa | gag | ggg | tac | 3568 |
| Gln | Ala | Val | Leu | Pro | Val | Val | Ala | Ala | Ser | Thr | Cys | Glu | Glu | Gly | Tyr |   |
| 985 |   |   |   | 990 |   |   |   | 995 |   |   |   | 1000 |

| aag | gaa | gca | gac | tta | cca | ctg | aca | gta | aca | gag | aac | atg | ttc | tgt | gca | 3616 |
| Lys | Glu | Ala | Asp | Leu | Pro | Leu | Thr | Val | Thr | Glu | Asn | Met | Phe | Cys | Ala |   |
|   |   |   |   | 1005 |   |   |   | 1010 |   |   |   | 1015 |

| ggt | tac | aag | aag | gga | cgt | tat | gat | gcc | tgc | agt | ggg | gac | agt | gga | gga | 3664 |
| Gly | Tyr | Lys | Lys | Gly | Arg | Tyr | Asp | Ala | Cys | Ser | Gly | Asp | Ser | Gly | Gly |   |
|   |   | 1020 |   |   |   | 1025 |   |   |   | 1030 |

| cct | tta | gtg | ttt | gct | gat | gat | tcc | cgt | acc | gaa | agg | cgg | tgg | gtc | ttg | 3712 |
| Pro | Leu | Val | Phe | Ala | Asp | Asp | Ser | Arg | Thr | Glu | Arg | Arg | Trp | Val | Leu |   |
|   |   | 1035 |   |   |   | 1040 |   |   |   | 1045 |

| gaa | ggg | att | gtc | agc | tgg | ggc | agt | ccc | agt | gga | tgt | ggc | aag | gcg | aac | 3760 |
| Glu | Gly | Ile | Val | Ser | Trp | Gly | Ser | Pro | Ser | Gly | Cys | Gly | Lys | Ala | Asn |   |
|   | 1050 |   |   |   | 1055 |   |   |   | 1060 |

| cag | tac | ggg | ggc | ttc | act | aaa | gtt | aac | gtt | ttc | ctg | tca | tgg | att | agg | 3808 |
| Gln | Tyr | Gly | Gly | Phe | Thr | Lys | Val | Asn | Val | Phe | Leu | Ser | Trp | Ile | Arg |   |
| 1065 |   |   |   | 1070 |   |   |   | 1075 |   |   |   | 1080 |

| cag | ttc | att | tgaaactgat | ctaaatattt | taagcatggt | tataaacgtc |   |   |   |   |   |   |   | 3857 |
| Gln | Phe | Ile | ttgttcctat tattgcttta ctggtttaac ccataagaag gttaacgggg taaggcacaa    3917 ggatcattgt ttctgtttgt ttttacaaat ggttctttta gtcagtgaat gagaatagta    3977 tccattggag actgttacct tttattctac cttttttatat tactatgcaa gtatttggga    4037

```
tatcttctac acatgaaaat tctgtcattt taccataaat ttggtttctg gtgtgtgtgt    4097
taagtccacc actagagaac gatgtaattt tcaatagtac atgaaataaa tatagaacaa    4157
atctattata aaaaaaaaaa aaaaa                                          4182
```

<210> SEQ ID NO 2
<211> LENGTH: 1083
<212> TYPE: PRT
<213> ORGANISM: Carcinoscorpius rotundicauda
<220> FEATURE:
<223> OTHER INFORMATION: any n or Xaa = Unknown

<400> SEQUENCE: 2

```
Met Trp Val Thr Cys Phe Asp Thr Phe Leu Phe Val Cys Glu Ser Ser
 1               5                  10                  15

Val Phe Cys Leu Leu Cys Val Trp Arg Phe Gly Phe Cys Arg Trp Arg
            20                  25                  30

Val Phe Tyr Ser Phe Pro Phe Val Lys Ser Thr Val Val Leu Leu Gln
        35                  40                  45

Cys Tyr His Tyr Ser Leu His Asn Thr Ser Lys Phe Tyr Ser Val Asn
    50                  55                  60

Pro Asp Lys Pro Glu Tyr Ile Leu Ser Gly Leu Val Leu Gly Leu Leu
65                  70                  75                  80

Ala Gln Lys Met Arg Pro Val Gln Ser Lys Gly Val Asp Leu Gly Leu
                85                  90                  95

Cys Asp Glu Thr Arg Phe Glu Cys Lys Cys Gly Asp Pro Gly Tyr Val
            100                 105                 110

Phe Asn Ile Pro Val Lys Gln Cys Thr Tyr Phe Tyr Arg Trp Arg Pro
        115                 120                 125

Tyr Cys Lys Pro Cys Asp Asp Leu Glu Ala Lys Asp Ile Cys Pro Lys
    130                 135                 140

Tyr Lys Arg Cys Gln Glu Cys Lys Ala Gly Leu Asp Ser Cys Val Thr
145                 150                 155                 160

Cys Pro Pro Asn Lys Tyr Gly Thr Trp Cys Ser Gly Glu Cys Gln Cys
                165                 170                 175

Lys Asn Gly Gly Ile Cys Asp Gln Arg Thr Gly Ala Cys Ala Cys Arg
            180                 185                 190

Asp Arg Tyr Glu Gly Val His Cys Glu Ile Leu Lys Gly Cys Pro Leu
        195                 200                 205

Leu Pro Ser Asp Ser Gln Val Gln Glu Val Arg Asn Pro Pro Asp Asn
    210                 215                 220

Pro Gln Thr Ile Asp Tyr Ser Cys Ser Pro Gly Phe Lys Leu Lys Gly
225                 230                 235                 240

Met Ala Arg Ile Ser Cys Leu Pro Asn Gly Gln Trp Ser Asn Phe Pro
                245                 250                 255

Pro Lys Cys Ile Arg Glu Cys Ala Met Val Ser Ser Pro Glu His Gly
            260                 265                 270

Lys Val Asn Ala Leu Ser Gly Asp Met Ile Glu Gly Ala Thr Leu Arg
        275                 280                 285

Phe Ser Cys Asp Ser Pro Tyr Tyr Leu Ile Gly Gln Glu Thr Leu Thr
    290                 295                 300

Cys Gln Gly Asn Gly Gln Trp Asn Gly Gln Ile Pro Gln Cys Lys Asn
305                 310                 315                 320

Leu Val Phe Cys Pro Asp Leu Asp Pro Val Asn His Ala Glu His Lys
                325                 330                 335
```

-continued

```
Val Lys Ile Gly Val Glu Gln Lys Tyr Gly Gln Phe Pro Gln Gly Thr
            340                 345                 350
Glu Val Thr Tyr Thr Cys Ser Gly Asn Tyr Phe Leu Met Gly Phe Asp
            355                 360                 365
Thr Leu Lys Cys Asn Pro Asp Gly Ser Trp Ser Gly Ser Gln Pro Ser
            370                 375                 380
Cys Val Lys Val Ala Asp Arg Glu Val Asp Cys Asp Ser Lys Ala Val
385                 390                 395                 400
Asp Phe Leu Asp Asp Val Gly Glu Pro Val Arg Ile His Cys Pro Ala
                405                 410                 415
Gly Cys Ser Leu Thr Ala Gly Thr Val Trp Gly Thr Ala Ile Tyr His
                420                 425                 430
Glu Leu Ser Ser Val Cys Arg Ala Ala Ile His Ala Gly Lys Leu Pro
            435                 440                 445
Asn Ser Gly Gly Ala Val His Val Val Asn Asn Gly Pro Tyr Ser Asp
            450                 455                 460
Phe Leu Gly Ser Asp Leu Asn Gly Ile Lys Ser Glu Glu Leu Lys Ser
465                 470                 475                 480
Leu Ala Arg Ser Phe Arg Phe Asp Tyr Val Ser Ser Ser Thr Ala Gly
                485                 490                 495
Lys Ser Gly Cys Pro Asp Gly Trp Phe Glu Val Asp Glu Asn Cys Val
                500                 505                 510
Tyr Val Thr Ser Lys Gln Arg Ala Trp Glu Arg Ala Gln Gly Val Cys
            515                 520                 525
Thr Asn Met Ala Ala Arg Leu Ala Val Leu Asp Lys Asp Val Ile Pro
            530                 535                 540
Asn Ser Leu Thr Glu Thr Leu Arg Gly Lys Gly Leu Thr Thr Thr Trp
545                 550                 555                 560
Ile Gly Leu His Arg Leu Asp Ala Glu Lys Pro Phe Ile Trp Glu Leu
                565                 570                 575
Met Asp Arg Ser Asn Val Val Leu Asn Asp Asn Leu Thr Phe Trp Ala
                580                 585                 590
Ser Gly Glu Pro Gly Asn Glu Thr Asn Cys Val Tyr Met Asp Ile Gln
            595                 600                 605
Asp Gln Leu Gln Ser Val Trp Lys Thr Lys Ser Cys Phe Gln Pro Ser
            610                 615                 620
Ser Phe Ala Cys Met Met Asp Leu Ser Asp Arg Asn Lys Ala Lys Cys
625                 630                 635                 640
Asp Asp Pro Gly Ser Leu Glu Asn Gly His Ala Thr Leu His Gly Gln
                645                 650                 655
Ser Ile Asp Gly Phe Tyr Ala Gly Ser Ser Ile Arg Tyr Ser Cys Glu
                660                 665                 670
Val Leu His Tyr Leu Ser Gly Thr Glu Thr Val Thr Cys Thr Thr Asn
            675                 680                 685
Gly Thr Trp Ser Ala Pro Lys Pro Arg Cys Ile Lys Val Ile Thr Cys
            690                 695                 700
Gln Asn Pro Pro Val Pro Ser Tyr Gly Ser Val Glu Ile Lys Pro Pro
705                 710                 715                 720
Ser Arg Thr Asn Ser Ile Ser Arg Val Gly Ser Pro Phe Leu Arg Leu
                725                 730                 735
Pro Arg Leu Pro Leu Pro Leu Ala Arg Ala Lys Pro Pro Pro Pro Lys
                740                 745                 750
Pro Arg Ser Ser Gln Pro Ser Thr Val Asp Leu Ala Ser Lys Val Lys
```

```
                755                 760                 765
Leu Pro Glu Gly His Tyr Arg Val Gly Ser Arg Ala Ile Tyr Thr Cys
    770                 775                 780

Glu Ser Arg Tyr Tyr Glu Leu Leu Gly Ser Gln Gly Arg Arg Cys Asp
785                 790                 795                 800

Ser Asn Gly Asn Trp Ser Gly Arg Pro Ala Ser Cys Ile Pro Val Cys
                805                 810                 815

Gly Arg Ser Asp Ser Pro Arg Ser Pro Phe Ile Trp Asn Gly Asn Ser
            820                 825                 830

Thr Glu Ile Gly Gln Trp Pro Trp Gln Ala Gly Ile Ser Arg Trp Leu
        835                 840                 845

Ala Asp His Asn Met Trp Phe Leu Gln Cys Gly Gly Ser Leu Leu Asn
    850                 855                 860

Glu Lys Trp Ile Val Thr Ala Ala His Cys Val Thr Tyr Ser Ala Thr
865                 870                 875                 880

Ala Glu Ile Ile Asp Pro Asn Gln Phe Lys Met Tyr Leu Gly Lys Tyr
                885                 890                 895

Tyr Arg Asp Asp Ser Arg Asp Asp Tyr Val Gln Val Arg Glu Ala
            900                 905                 910

Leu Glu Ile His Val Asn Pro Asn Tyr Asp Pro Gly Asn Leu Asn Phe
        915                 920                 925

Asp Ile Ala Leu Ile Gln Leu Lys Thr Pro Val Thr Leu Thr Thr Arg
    930                 935                 940

Val Gln Pro Ile Cys Leu Pro Thr Asp Ile Thr Arg Glu His Leu
945                 950                 955                 960

Lys Glu Gly Thr Leu Ala Val Val Thr Gly Trp Gly Leu Asn Glu Asn
                965                 970                 975

Asn Thr Tyr Ser Glu Thr Ile Gln Gln Ala Val Leu Pro Val Val Ala
            980                 985                 990

Ala Ser Thr Cys Glu Glu Gly Tyr Lys Glu Ala Asp Leu Pro Leu Thr
        995                 1000                1005

Val Thr Glu Asn Met Phe Cys Ala Gly Tyr Lys Lys Gly Arg Tyr Asp
    1010                1015                1020

Ala Cys Ser Gly Asp Ser Gly Gly Pro Leu Val Phe Ala Asp Asp Ser
025                 1030                1035                1040

Arg Thr Glu Arg Arg Trp Val Leu Glu Gly Ile Val Ser Trp Gly Ser
                1045                1050                1055

Pro Ser Gly Cys Gly Lys Ala Asn Gln Tyr Gly Gly Phe Thr Lys Val
            1060                1065                1070

Asn Val Phe Leu Ser Trp Ile Arg Gln Phe Ile
        1075                1080

<210> SEQ ID NO 3
<211> LENGTH: 3448
<212> TYPE: DNA
<213> ORGANISM: Carcinoscorpius rotundicauda
<220> FEATURE:
<221> NAME/KEY: CDS
<222> LOCATION: (18)..(3074)
<220> FEATURE:
<223> OTHER INFORMATION: any n or Xaa = Unknown

<400> SEQUENCE: 3
gtgaaggtaa cttaagt atg gtc tta gcg tcg ttt ttg gtg tct ggt tta      50
                   Met Val Leu Ala Ser Phe Leu Val Ser Gly Leu
                    1               5                  10
```

-continued

| | |
|---|---|
| gtt cta ggg cta cta gcc caa aaa atg cgc cca gtt cag tcc aaa gga<br>Val Leu Gly Leu Leu Ala Gln Lys Met Arg Pro Val Gln Ser Lys Gly<br>                15                      20                      25 | 98 |
| gta gat cta ggc ttg tgt gat gaa acg agg ttc gag tgt aag tgt ggc<br>Val Asp Leu Gly Leu Cys Asp Glu Thr Arg Phe Glu Cys Lys Cys Gly<br>          30                      35                      40 | 146 |
| gat cca ggc tat gtg ttc aac att cca gtg aaa caa tgt aca tac ttt<br>Asp Pro Gly Tyr Val Phe Asn Ile Pro Val Lys Gln Cys Thr Tyr Phe<br>45                      50                      55 | 194 |
| tat cga tgg agg ccg tat tgt aaa cca tgt gat gac ctg gag gct aag<br>Tyr Arg Trp Arg Pro Tyr Cys Lys Pro Cys Asp Asp Leu Glu Ala Lys<br>60                      65                      70                      75 | 242 |
| gat att tgt cca aag tac aaa cga tgt caa gag tgt aag gct ggt ctt<br>Asp Ile Cys Pro Lys Tyr Lys Arg Cys Gln Glu Cys Lys Ala Gly Leu<br>                    80                      85                      90 | 290 |
| gat agt tgt gtt act tgt cca cct aac aaa tat ggt act tgg tgt agc<br>Asp Ser Cys Val Thr Cys Pro Pro Asn Lys Tyr Gly Thr Trp Cys Ser<br>          95                      100                      105 | 338 |
| ggt gaa tgt cag tgt aag aat gga ggt atc tgt gac cag agg aca gga<br>Gly Glu Cys Gln Cys Lys Asn Gly Gly Ile Cys Asp Gln Arg Thr Gly<br>                110                      115                      120 | 386 |
| gct tgt gca tgt cgt gac aga tat gaa ggg gtg cac tgt gaa att ctc<br>Ala Cys Ala Cys Arg Asp Arg Tyr Glu Gly Val His Cys Glu Ile Leu<br>125                      130                      135 | 434 |
| aaa ggt tgt cct ctt ctt cca tcg gat tct cag gtt cag gaa gtc aga<br>Lys Gly Cys Pro Leu Leu Pro Ser Asp Ser Gln Val Gln Glu Val Arg<br>140                      145                      150                      155 | 482 |
| aat cca cca gat aat ccc caa act att gac tac agc tgt tca cca ggg<br>Asn Pro Pro Asp Asn Pro Gln Thr Ile Asp Tyr Ser Cys Ser Pro Gly<br>                160                      165                      170 | 530 |
| ttc aag ctt aag ggt atg gca cga att agc tgt ctc cca aat gga cag<br>Phe Lys Leu Lys Gly Met Ala Arg Ile Ser Cys Leu Pro Asn Gly Gln<br>                175                      180                      185 | 578 |
| tgg agt aac ttt cca ccc aaa tgt att cga gaa tgt gcc atg gtt tca<br>Trp Ser Asn Phe Pro Pro Lys Cys Ile Arg Glu Cys Ala Met Val Ser<br>          190                      195                      200 | 626 |
| tct cca gaa cat ggg aaa gtg aat gct ctt agt ggt gat atg ata gaa<br>Ser Pro Glu His Gly Lys Val Asn Ala Leu Ser Gly Asp Met Ile Glu<br>205                      210                      215 | 674 |
| ggg gct act tta cgg ttc tca tgt gat agt ccc tac tac ttg att ggt<br>Gly Ala Thr Leu Arg Phe Ser Cys Asp Ser Pro Tyr Tyr Leu Ile Gly<br>220                      225                      230                      235 | 722 |
| caa gaa aca tta acc tgt cag ggt aat ggt cag tgg aat gga cag ata<br>Gln Glu Thr Leu Thr Cys Gln Gly Asn Gly Gln Trp Asn Gly Gln Ile<br>                240                      245                      250 | 770 |
| cca caa tgt aag aac ttg gtc ttc tgt cct gac ctg gat cct gta aac<br>Pro Gln Cys Lys Asn Leu Val Phe Cys Pro Asp Leu Asp Pro Val Asn<br>255                      260                      265 | 818 |
| cat gct gaa cac aag gtt aaa att ggt gtg gaa caa aaa tat ggt cag<br>His Ala Glu His Lys Val Lys Ile Gly Val Glu Gln Lys Tyr Gly Gln<br>270                      275                      280 | 866 |
| ttt cct caa ggc act gaa gtg acc tat acg tgt tcg ggt aac tac ttc<br>Phe Pro Gln Gly Thr Glu Val Thr Tyr Thr Cys Ser Gly Asn Tyr Phe<br>285                      290                      295 | 914 |
| ttg atg ggt ttt gac acc tta aaa tgt aac cct gat ggg tct tgg tca<br>Leu Met Gly Phe Asp Thr Leu Lys Cys Asn Pro Asp Gly Ser Trp Ser<br>300                      305                      310                      315 | 962 |
| gga tca cag cca tcc tgt gtt aaa gtg gca gac aga gag gtc gac tgt<br>Gly Ser Gln Pro Ser Cys Val Lys Val Ala Asp Arg Glu Val Asp Cys<br>                320                      325                      330 | 1010 |

```
gac agt aaa gct gta gac ttc ttg gat gat gtt ggt gaa cct gtc agg      1058
Asp Ser Lys Ala Val Asp Phe Leu Asp Asp Val Gly Glu Pro Val Arg
            335                 340                 345 atc cac tgt cct gct ggc tgt tct ttg aca gct ggt act gtg tgg ggt      1106
Ile His Cys Pro Ala Gly Cys Ser Leu Thr Ala Gly Thr Val Trp Gly
            350                 355                 360 aca gcc ata tac cat gaa ctt tcc tca gtg tgt cgt gca gcc atc cat      1154
Thr Ala Ile Tyr His Glu Leu Ser Ser Val Cys Arg Ala Ala Ile His
365                 370                 375 gct ggc aag ctt cca aac tct gga gga gcg gtg cat gtt gtg aac aat      1202
Ala Gly Lys Leu Pro Asn Ser Gly Gly Ala Val His Val Val Asn Asn
380                 385                 390                 395 ggc ccc tac tcg gac ttt ctg ggt agt gac ctg aat ggg ata aaa tcg      1250
Gly Pro Tyr Ser Asp Phe Leu Gly Ser Asp Leu Asn Gly Ile Lys Ser
                400                 405                 410 gaa gag ttg aag tct ctt gcc cgg agt ttc cga ttc gat tat gtc cgt      1298
Glu Glu Leu Lys Ser Leu Ala Arg Ser Phe Arg Phe Asp Tyr Val Arg
            415                 420                 425 tcc tcc aca gca ggt aaa tca gga tgt cct gat gga tgg ttt gag gta      1346
Ser Ser Thr Ala Gly Lys Ser Gly Cys Pro Asp Gly Trp Phe Glu Val
            430                 435                 440 gac gag aac tgt gtg tac gtt aca tca aaa cag aga gcc tgg gaa aga      1394
Asp Glu Asn Cys Val Tyr Val Thr Ser Lys Gln Arg Ala Trp Glu Arg
            445                 450                 455 gct caa ggt gtg tgt acc aat atg gct gct cgt ctt gct gtg ctg gac      1442
Ala Gln Gly Val Cys Thr Asn Met Ala Ala Arg Leu Ala Val Leu Asp
460                 465                 470                 475 aaa gat gta att cca aat tcg ttg act gag act cta cga ggg aaa ggg      1490
Lys Asp Val Ile Pro Asn Ser Leu Thr Glu Thr Leu Arg Gly Lys Gly
                480                 485                 490 tta aca acc acg tgg ata gga ttg cac aga cta gat gct gag aag ccc      1538
Leu Thr Thr Thr Trp Ile Gly Leu His Arg Leu Asp Ala Glu Lys Pro
            495                 500                 505 ttt att tgg gag tta atg gat cgt agt aat gtg gtt ctg aat gat aac      1586
Phe Ile Trp Glu Leu Met Asp Arg Ser Asn Val Val Leu Asn Asp Asn
            510                 515                 520 cta aca ttc tgg gcc tct ggc gaa cct gga aat gaa act aac tgt gta      1634
Leu Thr Phe Trp Ala Ser Gly Glu Pro Gly Asn Glu Thr Asn Cys Val
            525                 530                 535 tat atg gac atc caa gat cag ttg cag tct gtg tgg aaa acc aag tca      1682
Tyr Met Asp Ile Gln Asp Gln Leu Gln Ser Val Trp Lys Thr Lys Ser
540                 545                 550                 555 tgt ttt cag ccc tca agt ttt gct tgc atg atg gat ctg tca gac aga      1730
Cys Phe Gln Pro Ser Ser Phe Ala Cys Met Met Asp Leu Ser Asp Arg
                560                 565                 570 aat aaa gcc aaa tgc gat gat cct gga tca ctg gaa aat gga cac gcc      1778
Asn Lys Ala Lys Cys Asp Asp Pro Gly Ser Leu Glu Asn Gly His Ala
            575                 580                 585 aca ctt cat gga caa agt att gat ggg ttc tat gct ggt tct tct ata      1826
Thr Leu His Gly Gln Ser Ile Asp Gly Phe Tyr Ala Gly Ser Ser Ile
            590                 595                 600 agg tac agc tgt gag gtt ctc cac tac ctc agt gga act gaa acc gta      1874
Arg Tyr Ser Cys Glu Val Leu His Tyr Leu Ser Gly Thr Glu Thr Val
            605                 610                 615 act tgt aca aca aat ggc aca tgg agt gct cct aaa cct cga tgt atc      1922
Thr Cys Thr Thr Asn Gly Thr Trp Ser Ala Pro Lys Pro Arg Cys Ile
620                 625                 630                 635 aaa gtc atc acc tgc caa aac ccc cct gta cca tca tat ggt tct gtg      1970
Lys Val Ile Thr Cys Gln Asn Pro Pro Val Pro Ser Tyr Gly Ser Val
```

-continued

```
                640                 645                 650
gaa atc aaa ccc cca agt cgg aca aac tcg ata agt cgt gtt ggg tca    2018
Glu Ile Lys Pro Pro Ser Arg Thr Asn Ser Ile Ser Arg Val Gly Ser
            655                 660                 665 cct ttc ttg agg ttg cca cgg tta ccc ctc cca tta gct aga gca gcc    2066
Pro Phe Leu Arg Leu Pro Arg Leu Pro Leu Pro Leu Ala Arg Ala Ala
        670                 675                 680 aaa cct cct cca aaa cct aga tcc tca caa ccc tct act gtg gac ttg    2114
Lys Pro Pro Pro Lys Pro Arg Ser Ser Gln Pro Ser Thr Val Asp Leu
    685                 690                 695 gct tct aaa gtt aaa cta cct gaa ggt cat tac cgg gta ggg tct cga    2162
Ala Ser Lys Val Lys Leu Pro Glu Gly His Tyr Arg Val Gly Ser Arg
700                 705                 710                 715 gcc atc tac acg tgc gag tcg aga tac tac gaa cta ctt gga tct caa    2210
Ala Ile Tyr Thr Cys Glu Ser Arg Tyr Tyr Glu Leu Leu Gly Ser Gln
                720                 725                 730 ggc aga aga tgt gac tct aat gga aac tgg agt ggt cgg cca gcg agc    2258
Gly Arg Arg Cys Asp Ser Asn Gly Asn Trp Ser Gly Arg Pro Ala Ser
            735                 740                 745 tgt att cca gtt tgt gga cgg tca gac tct cct cgt tct cct ttt atc    2306
Cys Ile Pro Val Cys Gly Arg Ser Asp Ser Pro Arg Ser Pro Phe Ile
        750                 755                 760 tgg aat ggg aat tct aca gaa ata ggt cag tgg ccg tgg cag gca gga    2354
Trp Asn Gly Asn Ser Thr Glu Ile Gly Gln Trp Pro Trp Gln Ala Gly
    765                 770                 775 atc tct aga tgg ctt gca gac cac aat atg tgg ttt ctc cag tgt gga    2402
Ile Ser Arg Trp Leu Ala Asp His Asn Met Trp Phe Leu Gln Cys Gly
780                 785                 790                 795 gga tct cta ttg aat gag aaa tgg atc gtc act gct gcc cac tgt gtc    2450
Gly Ser Leu Leu Asn Glu Lys Trp Ile Val Thr Ala Ala His Cys Val
                800                 805                 810 acc tac tct gct act gct gag att att gac ccc aat cag ttt aaa atg    2498
Thr Tyr Ser Ala Thr Ala Glu Ile Ile Asp Pro Asn Gln Phe Lys Met
            815                 820                 825 tat ctg ggc aag tac tac cgt gat gac agt aga gac gat gac tat gta    2546
Tyr Leu Gly Lys Tyr Tyr Arg Asp Asp Ser Arg Asp Asp Asp Tyr Val
        830                 835                 840 caa gta aga gag gct ctt gag atc cac gtg aat cct aac tac gac ccc    2594
Gln Val Arg Glu Ala Leu Glu Ile His Val Asn Pro Asn Tyr Asp Pro
    845                 850                 855 ggc aat ctc aac ttt gac ata gcc cta att caa ctg aaa act cct gtt    2642
Gly Asn Leu Asn Phe Asp Ile Ala Leu Ile Gln Leu Lys Thr Pro Val
860                 865                 870                 875 act ttg aca aca cga gtc caa cca atc tgt ctg cct act gac atc aca    2690
Thr Leu Thr Thr Arg Val Gln Pro Ile Cys Leu Pro Thr Asp Ile Thr
                880                 885                 890 aca aga gaa cac ttg aag gag gga aca tta gca gtg gtg aca ggt tgg    2738
Thr Arg Glu His Leu Lys Glu Gly Thr Leu Ala Val Val Thr Gly Trp
            895                 900                 905 ggt ttg aat gaa aac aac acc tat tca gag acg att caa caa gct gtg    2786
Gly Leu Asn Glu Asn Asn Thr Tyr Ser Glu Thr Ile Gln Gln Ala Val
        910                 915                 920 cta cct gtt gtt gca gcc agc acc tgt gaa gag ggg tac aag gaa gca    2834
Leu Pro Val Val Ala Ala Ser Thr Cys Glu Glu Gly Tyr Lys Glu Ala
    925                 930                 935 gac tta cca ctg aca gta aca gag aac atg ttc tgt gca ggt tac aag    2882
Asp Leu Pro Leu Thr Val Thr Glu Asn Met Phe Cys Ala Gly Tyr Lys
940                 945                 950                 955 aag gga cgt tat gat gcc tgc agt ggg gac agt gga gga cct tta gtg    2930
```

-continued

| | | |
|---|---|---|
| Lys Gly Arg Tyr Asp Ala Cys Ser Gly Asp Ser Gly Gly Pro Leu Val<br>                          960                        965                    970 | |
| ttt gct gat gat tcc cgt acc gaa agg cgg tgg gtc ttg gaa ggg att<br>Phe Ala Asp Asp Ser Arg Thr Glu Arg Arg Trp Val Leu Glu Gly Ile<br>                975                        980                    985 | 2978 |
| gtc agc tgg ggc agt ccc agt gga tgt ggc aag gcg aac cag tac ggg<br>Val Ser Trp Gly Ser Pro Ser Gly Cys Gly Lys Ala Asn Gln Tyr Gly<br>                990                        995                  1000 | 3026 |
| ggc ttc act aaa gtt aac gtt ttc ctg tca tgg att agg cag ttc att<br>Gly Phe Thr Lys Val Asn Val Phe Leu Ser Trp Ile Arg Gln Phe Ile<br>    1005                        1010                    1015 | 3074 |
| tgaaactgat ctaaatattt taagcatggt tataaacgtc ttgtttccta ttattgcttt | 3134 |
| actagtttaa cccataagaa ggttaactgg gtaaggcaca aggatcattg tttctgtttg | 3194 |
| tttttacaaa tggttatttt agtcagtgaa tgagaatagt atccattgaa gactgttacc | 3254 |
| ttttattcta ccttttata ttactatgta agtatttggg atatcttcta cacatgaaaa | 3314 |
| ttctgtcatt ttaccataaa tttggtttct ggtgtgtgct aagtccacca gtagagaacg | 3374 |
| atgtaatttt cactagcaca tgaaataaat atagaacaaa tctattataa actaccttaa | 3434 |
| aaaaaaaaaa aaaa | 3448 |

<210> SEQ ID NO 4
<211> LENGTH: 1019
<212> TYPE: PRT
<213> ORGANISM: Carcinoscorpius rotundicauda
<220> FEATURE:
<223> OTHER INFORMATION: any n or Xaa = Unknown

<400> SEQUENCE: 4

Met Val Leu Ala Ser Phe Leu Val Ser Gly Leu Val Leu Gly Leu Leu
 1               5                  10                  15

Ala Gln Lys Met Arg Pro Val Gln Ser Lys Gly Val Asp Leu Gly Leu
            20                  25                  30

Cys Asp Glu Thr Arg Phe Glu Cys Lys Cys Gly Asp Pro Gly Tyr Val
        35                  40                  45

Phe Asn Ile Pro Val Lys Gln Cys Thr Tyr Phe Tyr Arg Trp Arg Pro
    50                  55                  60

Tyr Cys Lys Pro Cys Asp Asp Leu Glu Ala Lys Asp Ile Cys Pro Lys
65                  70                  75                  80

Tyr Lys Arg Cys Gln Glu Cys Lys Ala Gly Leu Asp Ser Cys Val Thr
                85                  90                  95

Cys Pro Pro Asn Lys Tyr Gly Thr Trp Cys Ser Gly Glu Cys Gln Cys
            100                 105                 110

Lys Asn Gly Gly Ile Cys Asp Gln Arg Thr Gly Ala Cys Ala Cys Arg
        115                 120                 125

Asp Arg Tyr Glu Gly Val His Cys Glu Ile Leu Lys Gly Cys Pro Leu
    130                 135                 140

Leu Pro Ser Asp Ser Gln Val Gln Glu Val Arg Asn Pro Pro Asp Asn
145                 150                 155                 160

Pro Gln Thr Ile Asp Tyr Ser Cys Ser Pro Gly Phe Lys Leu Lys Gly
                165                 170                 175

Met Ala Arg Ile Ser Cys Leu Pro Asn Gly Gln Trp Ser Asn Phe Pro
            180                 185                 190

Pro Lys Cys Ile Arg Glu Cys Ala Met Val Ser Ser Pro Glu His Gly
        195                 200                 205

Lys Val Asn Ala Leu Ser Gly Asp Met Ile Glu Gly Ala Thr Leu Arg

```
                210                 215                 220
Phe Ser Cys Asp Ser Pro Tyr Tyr Leu Ile Gly Gln Glu Thr Leu Thr
225                 230                 235                 240

Cys Gln Gly Asn Gly Gln Trp Asn Gly Gln Ile Pro Gln Cys Lys Asn
                245                 250                 255

Leu Val Phe Cys Pro Asp Leu Asp Pro Val Asn His Ala Glu His Lys
            260                 265                 270

Val Lys Ile Gly Val Glu Gln Lys Tyr Gly Gln Phe Pro Gln Gly Thr
        275                 280                 285

Glu Val Thr Tyr Thr Cys Ser Gly Asn Tyr Phe Leu Met Gly Phe Asp
    290                 295                 300

Thr Leu Lys Cys Asn Pro Asp Gly Ser Trp Ser Gly Ser Gln Pro Ser
305                 310                 315                 320

Cys Val Lys Val Ala Asp Arg Glu Val Asp Cys Asp Ser Lys Ala Val
                325                 330                 335

Asp Phe Leu Asp Asp Val Gly Glu Pro Val Arg Ile His Cys Pro Ala
            340                 345                 350

Gly Cys Ser Leu Thr Ala Gly Thr Val Trp Gly Thr Ala Ile Tyr His
        355                 360                 365

Glu Leu Ser Ser Val Cys Arg Ala Ala Ile His Ala Gly Lys Leu Pro
    370                 375                 380

Asn Ser Gly Gly Ala Val His Val Val Asn Asn Gly Pro Tyr Ser Asp
385                 390                 395                 400

Phe Leu Gly Ser Asp Leu Asn Gly Ile Lys Ser Glu Glu Leu Lys Ser
                405                 410                 415

Leu Ala Arg Ser Phe Arg Phe Asp Tyr Val Arg Ser Ser Thr Ala Gly
            420                 425                 430

Lys Ser Gly Cys Pro Asp Gly Trp Phe Glu Val Asp Glu Asn Cys Val
        435                 440                 445

Tyr Val Thr Ser Lys Gln Arg Ala Trp Glu Arg Ala Gln Gly Val Cys
    450                 455                 460

Thr Asn Met Ala Ala Arg Leu Ala Val Leu Asp Lys Asp Val Ile Pro
465                 470                 475                 480

Asn Ser Leu Thr Glu Thr Leu Arg Gly Lys Gly Leu Thr Thr Thr Trp
                485                 490                 495

Ile Gly Leu His Arg Leu Asp Ala Glu Lys Pro Phe Ile Trp Glu Leu
            500                 505                 510

Met Asp Arg Ser Asn Val Val Leu Asn Asp Asn Leu Thr Phe Trp Ala
        515                 520                 525

Ser Gly Glu Pro Gly Asn Glu Thr Asn Cys Val Tyr Met Asp Ile Gln
    530                 535                 540

Asp Gln Leu Gln Ser Val Trp Lys Thr Lys Ser Cys Phe Gln Pro Ser
545                 550                 555                 560

Ser Phe Ala Cys Met Met Asp Leu Ser Asp Arg Asn Lys Ala Lys Cys
                565                 570                 575

Asp Asp Pro Gly Ser Leu Glu Asn Gly His Ala Thr Leu His Gly Gln
            580                 585                 590

Ser Ile Asp Gly Phe Tyr Ala Gly Ser Ser Ile Arg Tyr Ser Cys Glu
        595                 600                 605

Val Leu His Tyr Leu Ser Gly Thr Glu Thr Val Thr Cys Thr Thr Asn
    610                 615                 620

Gly Thr Trp Ser Ala Pro Lys Pro Arg Cys Ile Lys Val Ile Thr Cys
625                 630                 635                 640
```

-continued

```
Gln Asn Pro Pro Val Pro Ser Tyr Gly Ser Val Glu Ile Lys Pro Pro
                645                 650                 655
Ser Arg Thr Asn Ser Ile Ser Arg Val Gly Ser Pro Phe Leu Arg Leu
        660                 665                 670
Pro Arg Leu Pro Leu Pro Leu Ala Arg Ala Ala Lys Pro Pro Pro Lys
    675                 680                 685
Pro Arg Ser Ser Gln Pro Ser Thr Val Asp Leu Ala Ser Lys Val Lys
690                 695                 700
Leu Pro Glu Gly His Tyr Arg Val Gly Ser Arg Ala Ile Tyr Thr Cys
705                 710                 715                 720
Glu Ser Arg Tyr Tyr Glu Leu Leu Gly Ser Gln Gly Arg Arg Cys Asp
                725                 730                 735
Ser Asn Gly Asn Trp Ser Gly Arg Pro Ala Ser Cys Ile Pro Val Cys
        740                 745                 750
Gly Arg Ser Asp Ser Pro Arg Ser Pro Phe Ile Trp Asn Gly Asn Ser
    755                 760                 765
Thr Glu Ile Gly Gln Trp Pro Trp Gln Ala Gly Ile Ser Arg Trp Leu
770                 775                 780
Ala Asp His Asn Met Trp Phe Leu Gln Cys Gly Gly Ser Leu Leu Asn
785                 790                 795                 800
Glu Lys Trp Ile Val Thr Ala Ala His Cys Val Thr Tyr Ser Ala Thr
                805                 810                 815
Ala Glu Ile Ile Asp Pro Asn Gln Phe Lys Met Tyr Leu Gly Lys Tyr
        820                 825                 830
Tyr Arg Asp Asp Ser Arg Asp Asp Asp Tyr Val Gln Val Arg Glu Ala
    835                 840                 845
Leu Glu Ile His Val Asn Pro Asn Tyr Asp Pro Gly Asn Leu Asn Phe
850                 855                 860
Asp Ile Ala Leu Ile Gln Leu Lys Thr Pro Val Thr Leu Thr Thr Arg
865                 870                 875                 880
Val Gln Pro Ile Cys Leu Pro Thr Asp Ile Thr Thr Arg Glu His Leu
                885                 890                 895
Lys Glu Gly Thr Leu Ala Val Val Thr Gly Trp Gly Leu Asn Glu Asn
        900                 905                 910
Asn Thr Tyr Ser Glu Thr Ile Gln Gln Ala Val Leu Pro Val Val Ala
    915                 920                 925
Ala Ser Thr Cys Glu Glu Gly Tyr Lys Glu Ala Asp Leu Pro Leu Thr
930                 935                 940
Val Thr Glu Asn Met Phe Cys Ala Gly Tyr Lys Lys Gly Arg Tyr Asp
945                 950                 955                 960
Ala Cys Ser Gly Asp Ser Gly Gly Pro Leu Val Phe Ala Asp Asp Ser
                965                 970                 975
Arg Thr Glu Arg Arg Trp Val Leu Glu Gly Ile Val Ser Trp Gly Ser
        980                 985                 990
Pro Ser Gly Cys Gly Lys Ala Asn Gln Tyr Gly Gly Phe Thr Lys Val
    995                 1000                1005
Asn Val Phe Leu Ser Trp Ile Arg Gln Phe Ile
    1010                1015

<210> SEQ ID NO 5
<211> LENGTH: 204
<212> TYPE: DNA
<213> ORGANISM: Artificial Sequence
<220> FEATURE:
```

-continued

<223> OTHER INFORMATION: Description of Artificial Sequence: fusion
     joint between Vtgss and Factor C genes, see Figure 14A
<220> FEATURE:
<223> OTHER INFORMATION: any n or Xaa = Unknown
<220> FEATURE:
<221> NAME/KEY: CDS
<222> LOCATION: (52)..(204)

<400> SEQUENCE: 5

```
gtggaattct gcagatgcta ccggactcag atcaattcac atccaccagc c atg agg      57
                                                           Met Arg
                                                             1 gtg ctt gta cta gct ctt gct gtg gct ctc gca gtg ggg gac cag tcc     105
Val Leu Val Leu Ala Leu Ala Val Ala Leu Ala Val Gly Asp Gln Ser
      5                  10                  15 aac ttg ggg gat cta ggc ttg tgt gat gaa acg agg ttc gag tgt aag     153
Asn Leu Gly Asp Leu Gly Leu Cys Asp Glu Thr Arg Phe Glu Cys Lys
 20                  25                  30 tgt ggc gat cca ggc tat gtg ttc aac att cca gtg aaa caa tgt aca     201
Cys Gly Asp Pro Gly Tyr Val Phe Asn Ile Pro Val Lys Gln Cys Thr
 35                  40                  45                  50 tac                                                                 204
Tyr
```

<210> SEQ ID NO 6
<211> LENGTH: 51
<212> TYPE: PRT
<213> ORGANISM: Artificial Sequence
<220> FEATURE:
<223> OTHER INFORMATION: any n or Xaa = Unknown

<400> SEQUENCE: 6

```
Met Arg Val Leu Val Leu Ala Leu Ala Val Ala Leu Ala Val Gly Asp
  1               5                  10                  15

Gln Ser Asn Leu Gly Asp Leu Gly Leu Cys Asp Glu Thr Arg Phe Glu
             20                  25                  30

Cys Lys Cys Gly Asp Pro Gly Tyr Val Phe Asn Ile Pro Val Lys Gln
         35                  40                  45

Cys Thr Tyr
         50
```

<210> SEQ ID NO 7
<211> LENGTH: 4776
<212> TYPE: DNA
<213> ORGANISM: Artificial Sequence
<220> FEATURE:
<223> OTHER INFORMATION: Description of Artificial Sequence:pFastBacI
<220> FEATURE:
<223> OTHER INFORMATION: any n or Xaa = Unknown

<400> SEQUENCE: 7

```
gacgcgccct gtagcggcgc attaagcgcg gcgggtgtgg tggttacgcg cagcgtgacc      60
gctacacttg ccagcgccct agcgcccgct cctttcgctt tcttcccttc ctttctcgcc     120
acgttcgccg gctttccccg tcaagctcta aatcgggggc tccctttagg gttccgattt     180
agtgctttac ggcacctcga ccccaaaaaa cttgattagg gtgatggttc acgtagtggg     240
ccatcgccct gatagacggt ttttcgccct ttgacgttgg agtccacgtt ctttaatagt     300
ggactcttgt tccaaactgg aacaacactc aaccctatct cggtctattc ttttgattta     360
taagggattt tgccgatttc ggcctattgg ttaaaaaatg agctgattta acaaaaattt     420
aacgcgaatt ttaacaaaat attaacgttt acaatttcag gtggcacttt tcggggaaat     480
```

-continued

| | |
|---|---|
| gtgcgcggaa cccctatttg tttattttc taaatacatt caaatatgta tccgctcatg | 540 |
| agacaataac cctgataaat gcttcaataa tattgaaaaa ggaagagtat gagtattcaa | 600 |
| catttccgtg tcgcccttat tccctttttt gcggcatttt gccttcctgt ttttgctcac | 660 |
| ccagaaacgc tggtgaaagt aaaagatgct gaagatcagt tgggtgcacg agtgggttac | 720 |
| atcgaactgg atctcaacag cggtaagatc cttgagagtt tcgccccga gaacgttttt | 780 |
| ccaatgatga gcacttttaa agttctgcta tgtggcgcgg tattatcccg tattgacgcc | 840 |
| gggcaagagc aactcggtcg ccgcatacac tattctcaga atgacttggt tgagtactca | 900 |
| ccagtcacag aaaagcatct tacggatggc atgacagtaa gagaattatg cagtgctgcc | 960 |
| ataaccatga gtgataacac tgcggccaac ttacttctga caacgatcgg aggaccgaag | 1020 |
| gagctaaccg ctttttttgca acatgggg gatcatgtaa ctcgccttga tcgttgggaa | 1080 |
| ccggagctga atgaagccat accaaacgac gagcgtgaca ccacgatgcc tgtagcaatg | 1140 |
| gcaacaacgt tgcgcaaact attaactggc gaactactta ctctagcttc ccggcaacaa | 1200 |
| ttaatagact ggatggaggc ggataaagtt gcaggaccac ttctgcgctc ggcccttccg | 1260 |
| gctggctggt ttattgctga taaatctgga gccggtgagc gtgggtctcg cggtatcatt | 1320 |
| gcagcactgg ggccagatgg taagccctcc cgtatcgtag ttatctacac gacggggagt | 1380 |
| caggcaacta tggatgaacg aaatagacag atcgctgaga taggtgcctc actgattaag | 1440 |
| cattggtaac tgtcagacca gtttactca tatatacttt agattgattt aaaacttcat | 1500 |
| ttttaattta aaaggatcta ggtgaagatc ctttttgata atctcatgac caaaatccct | 1560 |
| taacgtgagt tttcgttcca ctgagcgtca gaccccgtag aaaagatcaa aggatcttct | 1620 |
| tgagatcctt ttttctgcg cgtaatctgc tgcttgcaaa caaaaaaacc accgctacca | 1680 |
| gcggtggttt gtttgccgga tcaagagcta ccaactcttt ttccgaaggt aactggcttc | 1740 |
| agcagagcgc agataccaaa tactgtcctt ctagtgtagc cgtagttagg ccaccacttc | 1800 |
| aagaactctg tagcaccgcc tacatacctc gctctgctaa tcctgttacc agtggctgct | 1860 |
| gccagtggcg ataagtcgtg tcttaccggg ttggactcaa gacgatagtt accggataag | 1920 |
| gcgcagcggt cgggctgaac ggggggttcg tgcacacagc ccagcttgga gcgaacgacc | 1980 |
| tacaccgaac tgagatacct acagcgtgag cattgagaaa gcgccacgct tcccgaaggg | 2040 |
| agaaaggcgg acaggtatcc ggtaagcggc agggtcggaa caggagagcg cacgagggag | 2100 |
| cttccagggg gaaacgcctg gtatctttat agtcctgtcg ggtttcgcca cctctgactt | 2160 |
| gagcgtcgat ttttgtgatg ctcgtcaggg gggcggagcc tatggaaaaa cgccagcaac | 2220 |
| gcggcctttt tacggttcct ggccttttgc tggccttttg ctcacatgtt ctttcctgcg | 2280 |
| ttatcccctg attctgtgga taaccgtatt accgcctttg agtgagctga taccgctcgc | 2340 |
| cgcagccgaa cgaccgagcg cagcgagtca gtgagcgagg aagcggaaga gcgcctgatg | 2400 |
| cggtattttc tccttacgca tctgtgcggt atttcacacc gcagaccagc cgcgtaacct | 2460 |
| ggcaaaatcg gttacggttg agtaataaat ggatgccctg cgtaagcggg tgtgggcgga | 2520 |
| caataaagtc ttaaactgaa caaaatagat ctaaactatg acaataaagt cttaaactag | 2580 |
| acagaatagt tgtaaactga atcagtccag ttatgctgt gaaaaagcat actggacttt | 2640 |
| tgttatggct aaagcaaact cttcattttc tgaagtgcaa attgcccgtc gtattaaaga | 2700 |
| ggggcgtggc caaggcatg gtaaagacta tattcgcggc gttgtgacaa tttaccgaac | 2760 |
| aactccgcgg ccgggaagcc gatctcggct tgaacgaatt gttaggtggc ggtacttggg | 2820 |
| tcgatatcaa agtgcatcac ttcttcccgt atgcccaact ttgtatagag agccactgcg | 2880 |

-continued

```
ggatcgtcac cgtaatctgc ttgcacgtag atcacataag caccaagcgc gttggcctca    2940
tgcttgagga gattgatgag cgcggtggca atgccctgcc tccggtgctc gccggagact    3000
gcgagatcat agatatagat ctcactacgc ggctgctcaa acctgggcag aacgtaagcc    3060
gcgagagcgc caacaaccgc ttcttggtcg aaggcagcaa gcgcgatgaa tgtcttacta    3120
cggagcaagt tcccgaggta atcggagtcc ggctgatgtt gggagtaggt ggctacgtct    3180
ccgaactcac gaccgaaaag atcaagagca gcccgcatgg atttgacttg gtcagggccg    3240
agcctacatg tgcgaatgat gcccatactt gagccaccta actttgtttt agggcgactg    3300
ccctgctgcg taacatcgtt gctgctgcgt aacatcgttg ctgctccata acatcaaaca    3360
tcgacccacg gcgtaacgcg cttgctgctt ggatgcccga ggcatagact gtacaaaaaa    3420
acagtcataa caagccatga aaaccgccac tgcgccgtta ccaccgctgc gttcggtcaa    3480
ggttctggac cagttgcgtg agcgcatacg ctacttgcat tacagtttac gaaccgaaca    3540
ggcttatgtc aactgggttc gtgccttcat ccgtttccac ggtgtgcgtc acccggcaac    3600
cttgggcagc agcgaagtcg aggcatttct gtcctggctg gcgaacgagc gcaaggtttc    3660
ggtctccacg catcgtcagg cattggcggc cttgctgttc ttctacggca aggtgctgtg    3720
cacggatctg ccctggcttc aggagatcgg aagacctcgg ccgtcgcggc gcttgccggt    3780
ggtgctgacc ccggatgaag tggttcgcat cctcggtttt ctggaaggcg agcatcgttt    3840
gttcgcccag gactctagct atagttctag tggttggcta cgtatactcc ggaatattaa    3900
tagatcatgg agataattaa aatgataacc atctcgcaaa taaataagta ttttactgtt    3960
ttcgtaacag ttttgtaata aaaaaaccta taaatattcc ggattattca taccgtccca    4020
ccatcgggcg cggatcccgg tccgaagcgc gcggaattca aaggcctacg tcgacgagct    4080
cactagtcgc ggccgctttc gaatctagag cctgcagtct cgaggcatgc ggtaccaagc    4140
ttgtcgagaa gtactagagg atcataatca gccataccac atttgtagag gttttacttg    4200
ctttaaaaaa cctcccacac ctccccctga acctgaaaca taaatgaat gcaattgttg    4260 ttgttaactt gtttattgca gcttataatg gttacaaata aagcaatagc atcacaaatt    4320
tcacaaataa agcattttt tcactgcatt ctagttgtgg tttgtccaaa ctcatcaatg    4380
tatcttatca tgtctggatc tgatcactgc ttgagcctag gagatccgaa ccagataagt    4440
gaaatctagt tccaaactat tttgtcattt ttaattttcg tattagctta cgacgctaca    4500
cccagttccc atctattttg tcactcttcc ctaaataatc cttaaaaact ccatttccac    4560
ccctcccagt tcccaactat tttgtccgcc cacagcgggg cattttttctt cctgttatgt    4620 ttttaatcaa acatcctgcc aactccatgt gacaaaccgt catcttcggc tacttttct    4680 ctgtcacaga atgaaaattt ttctgtcatc tcttcgttat taatgtttgt aattgactga    4740
atatcaacgc ttatttgcag cctgaatggc gaatgg                              4776
```